US006177423B1

(12) United States Patent
Amegadzie et al.

(10) Patent No.: US 6,177,423 B1
(45) Date of Patent: Jan. 23, 2001

(54) ISOQUINOLONES

(75) Inventors: Albert Kudzoi Amegadzie, Carrboro, NC (US); Maureen Elizabeth Carey; John Michael Domagala, both of Canton, MI (US); Liren Huang, Edmonton; Ronald George Micetich, Sherwood Park, both of (CA); Joseph Peter Sanchez, Novi, MI (US); Rajeshwar Singh, Edmonton (CA); Michael Andrew Stier, Ypsilanti, MI (US); Arkadii Vaisburg, Edmonton (CA)

(73) Assignee: Warner-Lambert Company, Morris Plains, NJ (US)

( * ) Notice: Under 35 U.S.C. 154(b), the term of this patent shall be extended for 0 days.

(21) Appl. No.: 09/254,645

(22) PCT Filed: Oct. 31, 1997

(86) PCT No.: PCT/US97/19872

§ 371 Date: Mar. 12, 1999

§ 102(e) Date: Mar. 12, 1999

(87) PCT Pub. No.: WO98/19648

PCT Pub. Date: May 14, 1998

Related U.S. Application Data

(60) Provisional application No. 60/029,909, filed on Nov. 1, 1996.

(51) Int. Cl.[7] .................... A61K 31/535; A61K 31/50; A61K 31/44; C07D 401/00
(52) U.S. Cl. .................. 514/232.8; 514/253.03; 514/290; 544/361; 544/126; 546/99
(58) Field of Search ............... 546/98, 100, 99, 546/101; 514/296, 290, 232.8, 253.03; 544/361, 126

(56) References Cited

U.S. PATENT DOCUMENTS

| 3,808,215 | 4/1974 | Christmann et al. ............ 260/281 |
| 3,880,859 | 4/1975 | Scheuermann et al. .......... 260/281 |
| 3,941,791 | 3/1976 | Hell et al. ................. 260/281 Q |
| 4,007,192 | 2/1977 | Fuchs et al. ................ 260/281 F |
| 5,076,831 | 12/1991 | Saupe et al. ..................... 71/90 |

FOREIGN PATENT DOCUMENTS

| 1494381 | 7/1977 | (GB) . |
| 50-34327 | * 4/1975 | (JP) . |
| 52-130822 | * 2/1977 | (JP) . |
| 52-100522 | * 8/1977 | (JP) . |
| 52-91029 | * 8/1977 | (JP) . |
| WO 9736041 | * 2/1997 | (WO) . |

OTHER PUBLICATIONS

Edafiogho, et al., Synthesis and Anticonvulsant Activity of Imidooxy Derivatives, J. Med. Chem., vol. 34, pp. 387–392, 1991.*

Chemical Abstracts, citation 38964c Fluorescent whiteners, vol. 81, 1974, p. 91.*

Pladikin, et al., Napthalic acid Derivatives. V. Reducation and hydrazinolysis of N–Hydroxynaphthalimide Derivatives, vol. 9(1), pp. 167–170, 1973.*

Chemical Abstract, citation 86:89476f, "Alpha–6–Deoxyoxytetracycline", vol. 86, p. 511, 1977.*

Chemical Abstract, citation 85:32866h, 3–Nitro– or 3,6–dinitro–4,5–dichloronaphthalimides, vol. 85, p. 32871, 1976.*

Varney et al., "Crystal–Structure–Based Design and Synthesis of Benz[cd]indole–Containing Inhibitors of Thymidylate Synthase", J. Med. Chem., vol. 35, No. 4, 1992, 663–676.

Birch et al., "The Synthesis of (±)–Xanthorrhoein", J. Chem. Soc. Org., vol. 5, 1966, 523–527.

Plakidin et al., "Naphthalic acid derivatives. XI. General preparative method for preparing 1H–benzo[cd] indol–2–one derivatives by the reaction of N–(2,4–dinitrophenoxy)naphthalimide with alkalies", Zh. Org. Khim., 13(10), 1977, 2194–2202.

(List continued on next page.)

Primary Examiner—Zinna Northington Davis
Assistant Examiner—Binta Robinson
(74) Attorney, Agent, or Firm—Elizabeth M. Anderson

(57) ABSTRACT

Benzo[de]isoquinoline-1,3-dione of Formula or a pharmaceutically acceptable salt thereof wherein R is hydrogen or a protecting group typically used in the art for protecting alcohols and $R_1$–$R_5$ are each independently chosen from H, Cl, Br, F, straight or branched alkyl $C_1$–$C_8$ alkyl, $C_3$–$C_8$ cycloalkyl, heterocycle or bridged heterocycle of 4–9 atoms containing 1–3 heteroatoms, —$(CR'_2)_n OR_6$, —$(CR'_2)_n N(R_6)_2$, —$(CR'_2)_n NR_6 COR_7$, —$(CR'_2)_n NR_6 SO_2 OR_7$, —$(CR'_2)_n NR_6 SO_2 N(R_6)_2$, —$(CR'_2)_n OSO_2 N(R_6)_2$, —$(CR'_2)_n CN$, —$(CR'_2)_n (NOR_6) R_7$, $NO_2$, $CF_3$, —$(CR'_2)_n SO_m R_7$, —$(CR'_2)_n SO_m R_7$, —$(CR'_2)_n CO_2 R_6$, —$(CR'_2)_n CON(R_6)_2$, Ph, and any two of $R_1$–$R_5$ may form a substituted or unsubstituted ring of 5–7 total atoms having 0–2 heteroatoms are claimed which are selective inhibitors of bacterial DNA gyrase and DNA topoisomerase useful in antibacterial agents. Methods for their preparation and formulation as well as novel intermediates useful in the preparation of the final products are also claimed.

11 Claims, No Drawings

OTHER PUBLICATIONS

Werbel and Thompson, "Organophosphorus Compounds as Schistosomicides", *J. Med. Chem.*, vol. 10, 1967, 32–36.

Plakidin et al., "Naphthalic acid derivatives. I. Some properties of nitro derivatives of N–acyloxynaphthalimide", *Zh. Org. Khim.*, 6(7), 1970, 1480–1485.

Plakidin et al., "Naphthalic acid derivatives. VI. Reaction of 4–bromo– and 4–methoxy–N–acyloxynaphthaloimides with alkaline solutions", *Zh. Org. Khim.*, 9(1), 1973, 171–175.

CA record for JP 52100522, 1978.

CA record for JP 49014326, 1975.

CA record for JP 48037323, 1974.

CA record for Kristallografiya, 1971, 16(5), 923–8.

CA record for JP 50034327, 1975.

*Chem. Ber.*, vol. 32, 1899, 3292 (will send copy when available).

*J. Chem. Soc.*, 1942, 562–564 (will send copy when available).

*Chem. Ber.*, vol. 22, 1895, 365 (will send copy when available).

CA record for Zh. Strukt. Khim., 1970, 11(5), 939–40.

Beilstein record for Bull. Int. Acad. Pol. Sci. Ser. Sci. Chim., 1931, 531.

Beilstein record for Bull. Acad. Pol. Sci. Lett. Cl. Sci. Math. Nat. Ser. A, 1926, 228.

Beilstein record for Sov. Phys. Crystallog., 1972, 16, 801.

* cited by examiner

ISOQUINOLONES

This application is based on application number PCT/US97/19872 filed on Oct. 31, 1997, under 35 U.S.C. § 371 and U.S. Provisional Application No. 60/029,909 filed Nov. 1, 1996.

BACKGROUND OF THE INVENTION

The chemical and biological literature abounds with reports on the benzo[de]isoquinoline-1,3-diones (I) due in great part to their cytotoxic and antitumor activities (*Proc. 10th. Int. Congress of Chemother.,* 1977;2:1216; *Cancer Chemother. Pharmac.,* 1980;4:61; *Eur. J. Med. Chem.,* 1981;16:207). Paul, et al. (*Arzneim Forsch/Drug Res.,* 1984;34:1243) performed a retrospective analysis of hundreds of compounds within the benzo[de]isoquinolone-1,3-dione class, and showed that all of their cytotoxic/antitumor biological activity was associated with the presence of an extended amino containing alkyl group at the diimide nitrogen ($R_2$).

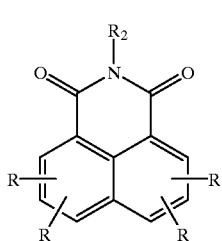

$R_2$ is $X(CH_2)_nN(R)_2$
X is O, NH, $CH_2$, or CHR, wherein
R = alkyl.

Longer chains or substituted chains were also tolerated. The cytotoxic/antitumor activities of these agents are mediated by their binding to DNA (*Biochem.,* 1982;21:2070; *J. Med. Chem.,* 1996;39:1609). A number of clinical candidates have been studied for the treatment of tumors and leukemia such as mitonafide (II), amonafide (III), and DMP840 (IV) (*Cancer Res.,* 1994;54:159; *Proc. Nat. Acad. Sci.,* 1995;92:8950).

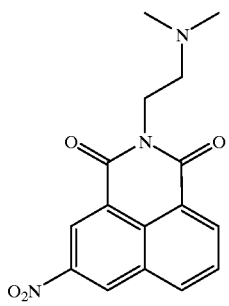

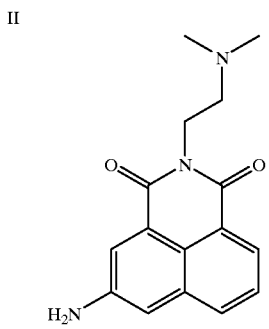

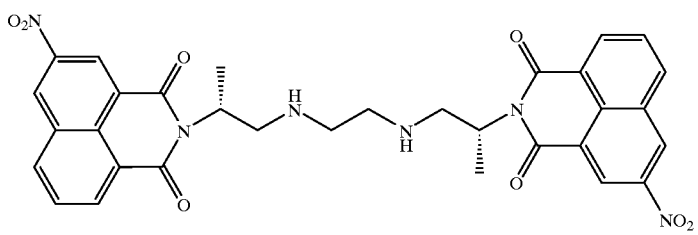

As cytotoxic and antitumor agents, compounds such as II–IV also display antibacterial activity (Chatterjee, et al., *Proc. Nat. Acad. Sci.,* 1995;92:8950) and antiparasitic activity (*Antimicrob. Agents Chemother.,* 1996;40:706). Because they bind DNA, they are able to inhibit mammalian and bacterial topoisomerases mediating the ultimate death of the cells (*Antimicrob. Agents Chemother.,* 1996;40:706). As antibacterial agents, these compounds lack specificity and are overly toxic to mammalian cells.

Due to the ever increasing incidence of antibiotic resistance appearing around the world, new antibacterials of novel structure have become very important for the treatment of bacterial infections (*J. Med. Chem.,* 1996;39:3853).

The subject of this invention is the discovery that the antibacterial activity of the benzo[de]isoquinoline-1,3-diones can be effectively separated from the cytotoxic and antitumor activities by the replacement of the alkyl amino group in compounds I–IV with a hydroxyl group (I, $R_2$=OH). These 2-hydroxy benzo[de]isoquinoline-1,3-diones (V) do not strongly intercalate or bind DNA, and in fact, are selective inhibitors of bacterial DNA gyrase and DNA topoisomerase IV. Compounds that inhibit two bacterial targets are expected to offer significant advantages in treatment of bacterial infection by lowering the frequency of bacterial resistance (Cozzarelli, et al., *Proc. Natl. Acad. Sci. USA,* 1995;92:11801; Hosino, et al., *Antimicrobial Agents Chemother.,* 1994;38:2623).

wherein R is a general substituent halo, nitro amino and the like.

Certain compounds of the type V have been described in U.S. Pat. No. 5,076,831 as intermediates to Va and as additives in the preparation of herbicidal formulations.

Compounds of type V were reported as synthetic intermediates leading to ring contracted product (*J. Med. Chem.*, 1992;35:663;*Zh. Org. Chim.*, 1977;13:2194). Studies of the base hydrolysis of compounds of type V have also been described (*Zh. Org. Chim.*, 1973;9:171 and 1970;6:1480) X-ray studies of compounds V were reported (*Zh. Strukt. Khim.*, 1970;11:939) as well as acylations of the hydroxy group (Zh. Org. Chim., 1972;8:165).

German patent DE2417789 and U.S. Pat. No. 3,941,791 describes compounds of the Type V as dyes and brighteners. U.S. Pat. No. 4,007,192 refers to a process of preparing the 6,7-dicarboxylic acids of compound V. U.S. Pat. No. 3,880,859 reports a wide variety of O-alkyl analog (Va) as fiber whiteners. There were no claims or disclosures of any antibacterial activity in any of the references cited above.

SUMMARY OF THE INVENTION

The instant invention is a compound of formula

I or a pharmaceutically acceptable salt thereof
wherein:

R is hydrogen or a protecting group typically used in the art for protecting alcohols: benzyl, 4-methoxybenzyl, ethyl, acetyl, benzoyl, 2,2,2-trichloroethyl, t-butyldimethylsilyl, t-butyl, and allyl;

$R_1$–$R_5$ are each independently chosen from H, Cl, Br, F, a straight or branched alkyl of 1–8 carbons, a cycloalkyl of 3–8 carbons, a heterocycle or bridged heterocycle of 4–9 atoms containing 1–3 heteroatoms, —$(CR'_2)_nOR_6$, —$(CR'_2)_nN(R_6)_2$, —$(CR'_2)_nNR_6COR_7$, —$(CR'_2)_nNR_6SO_2OR_7$, —$(CR'_2)_nNR_6SO_2N(R_6)_2$, —$(CR'_2)_nOSO_2N(R_6)_2$, —$(CR'_2)_nCN$, -$(CR'_2)_nC(NOR_6)R_7$, $NO_2$, $CR_3$, —$(CR'_2)_nSO_mR_7$, —$(CR'_2)_nCO_2R_6$, —$(CR'_2)_nCON(R_6)_2$, Ph and any two of $R_1$–$R_5$ may form a substituted or unsubstituted ring of 5–7 total atoms having 0–2 heteroatoms;

n is an integer of from 0 to 5;

m is an integer of from 0 to 3;

$R_6$ and $R_7$ are independently hydrogen, a straight or branched alkyl of 1–6 carbons, a cycloalkyl of 3–6 carbons, a heterocycle of 5–6 atoms with 1–3 heteroatoms, or Ph, all of which may be optionally substituted;

$R_8$ is a cycloalkyl of 3–7 carbons or a heterocycle of 4–9 atoms with 1–4 heteroatoms;

R' is $R_6$,F, Br, Cl, $OR_6$, $N(R_6)_2$, and any two R's may form a ring of 3–6 total atoms with 0–2 heteroatoms;

wherein the alkyls, cycloalkyls, heterocycles, and Ph recited above may be optionally substituted; and wherein the substituents are selected from a straight or branched alkyl of 1–4 carbons, Br, F, Cl, —$(CR'_2)_nOR_6$, —$(CR'_2)_nN(R_6)_2$, —$(CR'_2)_nNR_6COR_7$, —$(CR'_2)_nNR_6SO_2OR_7$, —$(CR'_2)_nNR_6SO_2N(R_6)_2$, —$(CR'_2)_nOSO_2N(R_6)_2$, —$(CR'_2)_nCN$, —$(CR'_2)_nC(NOR_6)R_7$, $NO_2$, $CF_3$, —$(CR'_2)_nSO_mR_7$,—$(CR'_2)_nCO_2R_6$,—$(CR'_2)_nR_8$,—$(CR'_2)_nCON(R_6)_2$, and Ph.

Preferred compounds of the invention are those of Formula I above wherein

R is selected from hydrogen, benzyl, 4-methoxybenzyl, methyl, acetyl, benzoyl, 2,2,2-trichloroethyl, t-butyldimethylsilyl, t-butyl, allyl, and trimethylsilyl;

$R_1$, $R_2$, $R_3$, $R_4$, and $R_5$ are each independently selected from hydrogen, chlorine, bromine, fluorine, straight or branched alkyl of from 1–8 carbons, cycloalkyl of from 3–8 carbons, heterocycle of from 4–8 atoms having from 1–3 heteroatoms, —$(CR'_2)_nOR_6$, —$(CR'_2)_nN(R_6)_2$, —$(CR'_3)_nNR_6COR_7$, —$(CR'_2)_nNR_6SO_2OR_7$, —$(CR'_2)_nNR_6SO_2N(R_6)_2$, —$(CR'_2)_nOSO_2N(R_6)_2$, —$(CR'_2)_nCN$, —$(CR'_2)_nC(NOR_6)R_7$,

—$NO_2$,

—$(CR'_2)_nSO_mR_7$,

—$CF_3$,

—$(CR'_2)_nCO_2R_6$,

—(CR'$_2$)$_n$CON(R$_6$)$_2$,
—phenyl;
wherein n is an integer from 0 to 5;
m is an integer of from 0 to 3; and
R$_6$ and R$_7$ are each independently selected from hydrogen,
straight or branched alkyl of from 1–6 carbons,
cycloalkyl of from 3–6 carbons,
heterocycle of from 5–6 atoms having from 1–3 heteroatoms, or
phenyl;
R$_8$ is a heterocycle of 5 or 6 atoms with 1 or 2 heteroatoms;
R' is hydrogen,
fluorine,
chlorine,
bromine,
OR$_6$, or
N(R$_6$)$_2$ wherein R$_6$ is alkyl; and
each of alkyl, cycloalkyl, heterocycle, and phenyl above is each independently unsubstituted or substituted with from 1–3 substituents selected from:
methyl, ethyl, propyl, isopropyl, butyl, sec-butyl, t-butyl, F, Cl, Br, CF$_3$, CN, COCH$_3$, CO$_2$H, CONH$_2$, C(R'$_2$)$_n$N(R$_6$)$_2$, C(R'$_2$)$_n$OR$_6$, NO$_2$, NR$_6$COR$_6$, CO$_2$R$_6$, or OCOR$_6$.

More preferred compounds of the invention are those of Formula I above wherein any two of R$_1$–R$_5$ may form a substituted or unsubstituted ring of from 5–7 atoms having from 0–2 heteroatoms selected from oxygen, sulfur, and nitrogen. Still more preferred compounds of the invention are those of Formula I above wherein R is H, benzyl, 4-methoxybenzyl, ethyl, acetyl, alkyl benzoyl, 2,2,2-trichloroethyl, or t-butyldimethylsilyl and any R$_1$–R$_5$ may be chosen from F, Cl, Br, OMe, and a substituted or unsubstituted piperidine, morpholine, piperazine, pyrrolidine, or thiomorpholine.

Most preferred compounds of the invention are those of Formula I above wherein
R is H;
R$_1$–R$_5$ is H, Cl, Br, F, OCH$_3$, NO$_2$, or CH$_3$ and at least one R$_1$–R$_5$ is a heterocycle.

Still other most preferred compounds of the invention are those of Formula I above wherein
R is H;
R$_1$–R$_5$ is H, Cl, Br, F, OCH$_3$, NO$_2$, or CH$_2$ and at least one R$_1$–R$_5$ is 3- or 4-amino-piperidin-1-yl, 3- or 4-aminomethyl-piperidin-1-yl, 3-amino or 3-aminomethyl-pyrrolidin-1-yl, 3-amino or 3-aminomethyl-azetidin-1-yl, [S-(R*,S*)]-3-(1-aminoethyl)-pyrrolidin-1-yl, trans-3-amino-4-methyl-pyrrolidin-1-yl, 6-amino-3-azo-bicyclo[3.1.0]hex-3-yl, or octahydro-1H-pyrrolo[3,4-b]pyridin-6-yl.

Still other most preferred compounds of the invention are those of Formula I above wherein
R is H;
R$_2$ is halogen at the five position;
R$_3$ is heterocycle at the six position which heterocycle is selected from an unsubstituted or substituted piperazinyl, morpholinyl, pyrrolidinyl, azetidinyl, bicyclo[3.1.0]hex-1-yl, 2-azabicyclo[4.3.0]nonane-2-yl, and piperidinyl;
which substituents are one or more selected from
—(CR'$_2$)$_n$OR$_6$, —(CR'$_2$)$_n$N(R$_6$)2, —(CR'$_2$)$_n$NR$_6$COR$_7$, —(CR'$_2$)$_n$NR$_6$SO$_2$OR$_7$, —(CR'$_2$)$_n$NR$_6$SO$_2$N(R$_6$)2, —(CR'$_2$)$_n$OSO$_2$N(R$_6$)$_2$, —(CR'$_2$)$_n$CN, —(CR'$_2$)$_n$C(NOR$_6$)R$_7$, NO$_2$, —(CR'$_2$)$_n$SO$_m$R$_7$, —(CR'$_2$)$_n$CO$_2$R$_6$, —(CR'$_2$)$_n$CON(R$_6$)$_n$, Ph, and F, Cl, and Br; and R$_4$ and R$_5$ are each hydrogen.

Other most preferred compounds of the invention are those according to Formula I and selected from:
2-Hydroxy-5-nitro-benzo[de]isoquinoline-1,3-dione;
2-Hydroxy-6-nitro-benzo[de]isoquinoline-1,3-dione;
2,5-Dihydroxy-benzo[de]isoquinoline-1,3-dione;
6-Bromo-2-hydroxy-benzo[de]isoquinoline-1,3-dione;
6-Chloro-2-hydroxy-benzo[de]isoquinoline-1,3-dione;
6-Chloro-2-hydroxy-benzo[de]isoquinoline-1,3-dione;
6-Amino-2-hydroxy-benzo[de]isoquinoline-1,3-dione;
5-Amino-2-hydroxy-benzo[de]isoquinoline-1,3-dione;
5-Acetamido-N-2-hydroxy-benzo[de]isoquinoline-1,3-dione;
5-Trifluoromethanesulfonyloxy-2-hydroxy-benzo[de]isoquinoline-1,3-dione;
5-Fluoro-2-hydroxy-benzo[de]isoquinoline-1,3-dione;
6-Fluoro-2-hydroxy-benzo[de]isoquinoline-1,3-dione;
2-Hydroxy-5-methoxy-benzo[de]isoquinoline-1,3-dione;
5-Ethoxy-2-hydroxy-benzo[de]isoquinoline-1,3-dione;
2-Hydroxy-6-methylthio-benzo[de]isoquinoline-1,3-dione;
2-Hydroxy-6-methoxy-benzo[de]isoquinoline-1,3-dione;
2-Hydroxy-5-methyl-benzo[de]isoquinoline-1,3-dione;
5-(2-Dimethylamino-ethoxy)-2-hydroxy-benzo[de]isoquinoline-1,3-dione;
2-Hydroxy-5-(2-acetoxy-ethoxy)-benzo[de]isoquinoline-1,3-dione;
2-Hydroxy-5-(2-hydroxy-ethoxy)-benzo[de]isoquinoline-1,3-dione;
2-Hydroxy-5-(2-carboxy-ethoxy)-benzo[de]isoquinoline-1,3-dione;
6-Amino-5-bromo-2-hydroxy-benzo[de]isoquinoline-1,3-dione;
6-Amino-5-chloro-2-hydroxy-benzo[de]isoquinoline-1,3-dione;
5-Amino-6-chloro-2-hydroxy-benzo[de]isoquinoline-1,3-dione;
2,5-Dihydroxy-6-nitro-benzo[de]iosquinoline-1,3-dione;
6-Amino-2-hydroxy-5-methoxy-benzo[de]isoquinoline-1,3-dione;
5-Bromo-2-hydroxy-6-methoxy-benzo[de]isoquinoline-1,3-dione;
6-Bromo-2-hydroxy-5-methoxy-benzo[de]isoquinoline-1,3-dione;
6-(2-Chloroacetamido)-methyl-2,5-dihydroxy-benzo[de]isoquinoline-1,3-dione;
6-Aminomethyl-2,5-dihydroxy-benzo[de]isoquinoline-1,3-dione, hydrochloride;
6-Acetamidomethyl-2,5-dihydroxy-benzo[de]isoquinoline-1,3-dione;
6-Acetamidomethyl-2-hydroxy-5-methoxy-benzo[de]isoquinoline-1,3-dione;
6-Aminomethyl-2-hydroxy-5-methoxy-benzo[de]isoquinoline-1,3-dione;
2-Hydroxy-5,8-dinitro-benzo[de]isoquinoline-1,3-dione;
5,8-Diamino-2-hydroxy-benzo[de]isoquinoline-1,3-dione;
5,8-Diacetamido-2-hydroxy-benzo[de]isoquinoline-1,3-dione;
2-Hydroxy-5-methoxy-6-nitro-benzo[de]isoquinoline-1,3-dione; and
2-Hydroxy-6,7-dinitro-benzo[de]isoquinoline-1,3-dione.

Other most preferred compounds of the invention are selected from:
2-Hydroxy-6-(4-methyl-piperazin-1-yl)-benzo[de]isoquinoline-1,3-dione;
2-Hydroxy-6-(pyrrolidin-1-yl)-benzo[de]isoquinoline-1,3-dione;

2-Hydroxy-6-(morpholin-4-yl)-benzo[de]isoquinoline-1,3-dione;
2-Hydroxy-6-(piperidin-1-yl)-benzo[de]isoquinoline-1,3-dione;
2-Hydroxy-5-methoxy-6-(4-methyl-piperazin-1-yl)-benzo[de]isoquinoline-1,3-dione, hydrochloride;
2-Hydroxy-5-methoxy-6-(pyrrolidin-1-yl)-benzo[de]isoquinoline-1,3-dione;
2-Hydroxy-5-methoxy-6-(piperidin-1-yl)-benzo[de]isoquinoline-1,3-dione;
2-Hydroxy-5-methoxy-6-(morpholin-4-yl)-benzo[de]isoquinoline-1,3-dione;
5-Hydroxy-11H-8,10-dioxa-5-aza-benzo[de]anthracene-4,6-dione;
5-Hydroxy-11H,11-methoxy-8,10-dioxa-5-aza-benzo[de]anthracene-4,6-dione;
5-Bromo-2-hydroxy-6-(piperidine-1-yl)-benzo[de]isoquinoline-1,3-dione;
5-Bromo-2-hydroxy-6-(4-methylpiperazin-1-yl)-benzo[de]isoquinoline-1,3-dione;
5-Bromo-2-hydroxy-6-(3-methylpiperidin-1-yl)-benzo[de]isoquinoline-1,3-dione;
5-Bromo-2-hydroxy-6-(pyrrolidin-1-yl)-benzo[de]isoquinoline-1,3-dione;
5-Bromo-6-dimethylamino-2-hydroxy-benzo[de]isoquinoline-1,3-dione;
(S)-6-(3-Amino-pyrrolidin-1-yl)-5-bromo-2-hydroxy-benzo[de]isoquinoline-1,3-dione, hydrochloride;
5-Cyano-2-hydroxy-6-(piperidin-1-yl)-benzo[de]isoquinoline-1,3-dione;
5-Cyano-2-hydroxy-6-(morpholin-1-yl)-benzo[de]isoquinoline-1,3-dione;
5-Cyano-2-hydroxy-6-(pyrrolidin-1-yl)-benzo[de]isoquinoline-1,3-dione;
(S)-6-(3-Amino-pyrrolidin-1-yl)-5-cyano-2-hydroxy-benzo[de]isoquinoline-1,3-dione, hydrochloride;
5-Bromo-2-hydroxy-7-(pyrrolidin-1-yl)-benzo[de]isoquinoline-1,3-dione;
2-Hydroxy-5-methyl-7-(pyrrolidin-1-yl)-benzo[de]isoquinoline-1,3-dione;
5-Bromo-2-hydroxy-7-(piperidin-1-yl)-benzo[de]isoquinoline-1,3-dione;
6-(3-Amino-pyrrolidin-1-yl)-2-hydroxy-benzo[de]isoquinoline-1,3-dione;
6-(3-Amino-pyrrolidin-1-yl)-2-hydroxy-5-methoxy-benzo[de]isoquinoline-1,3-dione;
5-Acetamido-2-hydroxy-6-(pyrrolidin-1-yl)-benzo[de]isoquinoline-1,3-dione;
5-Amino-2-hydroxy-6-(pyrrolidin-1-yl)-benzo[de]isoquinoline-1,3-dione;
2-Hydroxy-5-nitro-6-(pyrrolidin-1-yl)-benzo[de]isoquinoline-1,3-dione;
5-Chloro-2-hydroxy-6-[3-methoxypyrrolidin-1-yl]-benzo[de]isoquinoline-1,3-dione;
6-(3-Amino-azetidin-1-yl)-5-chloro-2-hydroxy-benzo[d,e]isoquinoline-1,3-dione;
4-Amino-6-(3-amino-azetidin-1-yl)-7,8-dibromo-5-chloro-2-hydroxy-benzo[d,e]isoquinolone-1,3-dione;
5,6-Dichloro-2-hydroxy-benzo[de]isoquinoline-1,3-dione;
6-Bromo-5-methyl-2-hydroxy-benzo[de]isoquinoline-1,3-dione;
6,8-Dibromo-2-hydroxy-5-methyl-benzo[de]isoquinoline-1,3-dione;
2-Hydroxy-6,7-dinitro-5-methoxy-benzo[de]isoquinoline-1,3-dione;
6,7-Diamino-2-hydroxy-5-methoxy-benzo[de]isoquinoline-1,3-dione;
5-Bromo-2-hydroxy-6-nitro-benzo[de]isoquinoline-1,3-dione;
5-Bromo-6,7-dinitro-2-hydroxy-benzo[de]isoquinoline-1,3-dione;
2-Hydroxy-8-nitro-6-(pyrrolidin-1-yl)-benzo[de]isoquinoline-1,3-dione;
2-Hydroxy-5,8-dinitro-6-(pyrrolidin-1-yl)-benzo[de]isoquinoline-1,3-dione;
5-Hydroxy-9-methyl-10H, 5,8,10-triaza-cyclopenta[a]phenalene-4,6-dione;
5-Chloro-2-hydroxy-8-nitro-6-(pyrrolidin-1-yl)-benzo[de]isoquinoline-1,3-dione;
5,6-Dichloro-2-hydroxy-7-(pyrrolidin-1-yl)-benzo[de]isoquinoline-1,3-dione;
2,5-Dihydroxy-2,3-dihydro-1,3-dioxo-1H-benzo[de]isoquinoline-6-carboxaldehyde;
6-Hydroxyiminomethyl-2,5-dihydroxy-benzo[de]isoquinoline-1,3-dione;
2-Hydroxy-5,6-dimethoxy-benzo[de]isoquinoline-1,3-dione;
2-Hydroxy-5,6-methylenedioxy-benzo[de]isoquinoline-1,3-dione;
5-Hydroxy-9H,10H-8,11-dioxa-5-aza-benzo[de]anthracene-4,6-dione;
5-Hydroxy-8H-9,11-dioxa-5-aza-benzo[de]anthracene-4,6-dione;
6-Bromo-2,5-dihydroxy-benzo[de]isoquinoline-1,3-dione;
5-Hydroxy-10-methyl-9,10-dihydro-8-oxa-5,10-diaza-cyclopenta[a]phenalene-4,6-dione;
5,10-Diaza-8-oxa-benzo[de]anthracene-4,6-dione;
2,5-Dihydroxy-6-(piperidin-1-yl)-methyl-benzo[de]isoquinoline-1,3-dione;
5-Fluoro-2-hydroxy-6-(pyrrolidin-1-yl)-benzo[de]isoquinoline-1,3-dione;
2-Hydroxy-4-methoxy-benzo[de]isoquinoline-1,3-dione;
8-Amino-2-hydroxy-4-methoxy-benzo[de]isoquinoline-1,3-dione;
8-Bromo-5-chloro-6-(pyrrolidin-1-yl)-benzo[de]isoquinoline-1,3-dione;
4-Amino-7-(3-amino-pyrrolidin-1-yl)-2-hydroxy-5,6,8-trichlorobenzo[d,e]isoquinoline-1,3-dione.

The instant invention is also a pharmaceutical composition which comprises an antibacterially effective amount of a compound for Formula I or a pharmaceutically acceptable salt thereof with a pharmaceutically acceptable carrier.

The invention further includes a method for treating bacterial infection in a mammal which comprises administering to said mammal an antibacterially effective amount of a compound of Formula I or a pharmaceutical composition of the same of a mammal in need thereof.

The invention further includes a method of selectively inhibiting bacterial DNA gyrase and DNA topoisomerase in a mammal in need of said inhibition which comprises administering to said mammal a compound of Formula I.

The invention further includes novel intermediates of formula

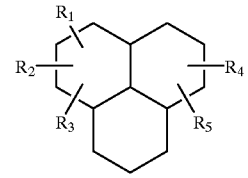

wherein $R_1$–$R_5$ are as defined above, and one of $R_1$–$R_5$ is a leaving group selected from halogen, OMe, $NO_2$, and triflate which leaving group is suitable for displacement by a nitrogen heterocycle.

DETAILED DESCRIPTION OF THE INVENTION

The terms describing the compounds of the instant invention are as follows:

Alcohol protecting groups are benzyl, 4-methoxybenzyl, ethyl, acetyl, benzoyl, 2,2,2-trichloroethyl, t-butyldimethylsilyl, trimethylsilyl, t-butyl, allyl, or as described in Greene, Theodora W., *Protective Groups in Organic Synthesis,* 1991:1–9.

The alkyl groups of the invention are both straight and branched carbon chains of from 1–8 carbon atoms. Representative of such groups are methyl, ethyl, propyl, isopropyl, and the like.

The cycloalkyl groups of the invention are those having 3–8 carbon atoms such as cyclopropyl, cyclobutyl, cyclopentyl, and cyclohexyl.

Heterocycle is a cyclic, bicyclic ring or bridged system having from 4–10 atoms, from one to four of which are selected from O, S, and N. Heterocycle includes non-aromatic groups such as morpholino and pyrrolidino. Preferred heterocycles are 5- or 6-membered mono-cyclic aromatic rings having 1 or 2 heteroatoms. Heterocycle also includes bicyclic rings such as benzofuran, isothiazolone, indole, and the like. Heterocycle also includes bridged ring systems. Typical groups represented by the term include:

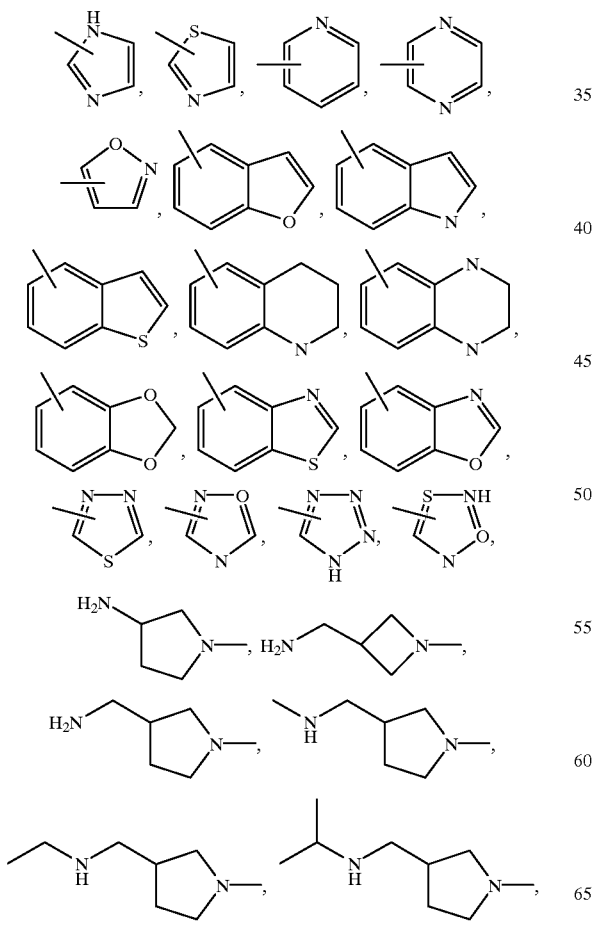

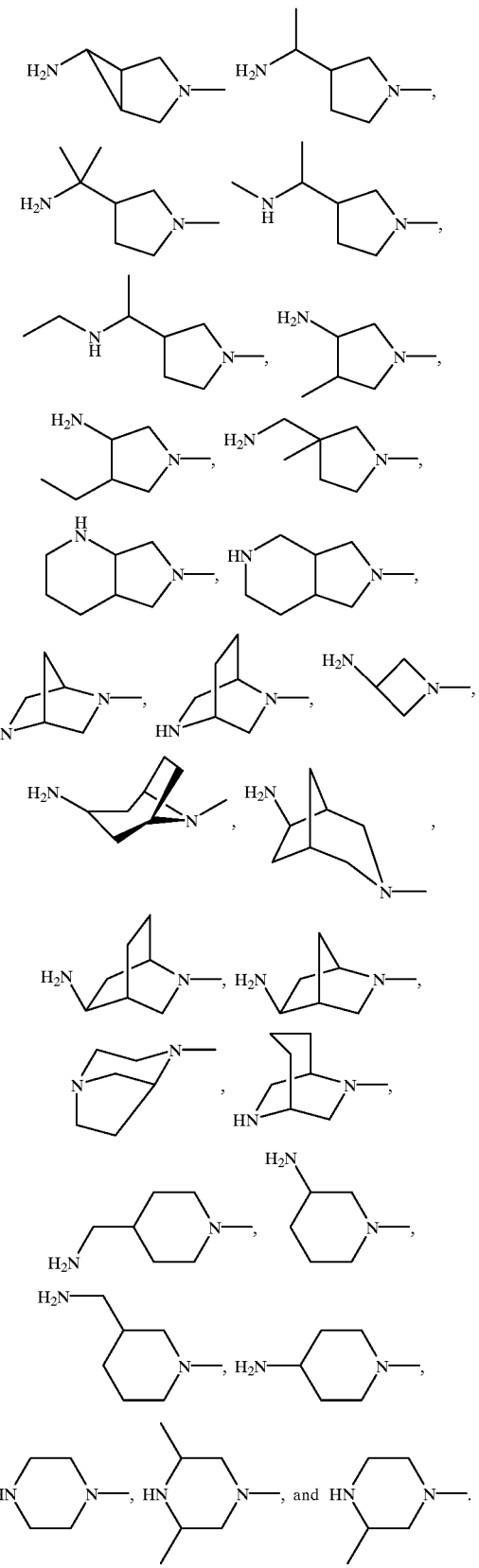

wherein the hyphen indicates the point of attachment. The groups above and below are optionally substituted on the peripheral nitrogens by alkyl groups as defined above or by nitrogen protecting groups as described by Green (referenced above). Other typically preferred groups include pyrimidine, pyridazine, pyrazine, oxazole, pyrazole, thiazole, and the like. Most preferred are: piperazine, pyrrolidine, morpholine, thiomorpholine, thiazole, oxazole, isoxazole, piperidine, and azetidine.

Any two of the $R_1$–$R_5$ groups can form a ring of from 5–7 atoms (this ring includes the carbons to which the $R_1$–$R_5$ group is attached). Such rings are: dioxalane, benzoxazine, indane, 1,3-benzodioxole, 2,3-dihydrobenzoxazole, 2,3-dihydrobenzofuran, 2,3-dihydro-1H-isoindole, 1,3-dihydroisofuran, 1,3-benzoxathiazole, 2,3-dihydro-1H-indole, 2,3-dihydro-1,4-benzodioxin, 3,4-dihydro-2H-1,4-benzoxazine, 3,4-dihydro-2H-1,3-benzoxazine, 4H-1,3-benzodioxin, 3,4-dihydro-2H-1-benzopyran, 3,4-dihydro-1H-2-benzopyran, 1,2,3,4-tetrahydroquinoxaline, 1,2,3,4-tetrahydroisoquinoline, 2,3-dihydro-1,4-benzoxathinindane, 1,2,3,4-tetrahydronaphthalene, and the like.

The R' group is $R_6$, hydrogen, a straight or branched alkyl of 1–6 carbons, a cycloalkyl of 3–6 carbons, a heterocycle of 5–6 atoms with 1–3 heteroatoms, phenyl, all of which may be unsubstituted or substituted as discussed below. R' is also F, Br, Cl, $OR_6$, or $N(R_6)_2$. Any two R' groups can form a ring having from 3–6 atoms having from 0–2 heteroatoms including a spirocycle which is a carbocyclic or heterocyclic ring whose ends meet at a single carbon in a chain or another ring.

Each of the terms above (alkyl, cycloalkyl, heterocycle, and the phenyl group) can be unsubstituted or substituted with from 1–3 substituents. The substituents are selected from: a straight or branched alkyl of 1–4 atoms such as methyl, ethyl, isopropyl, sec-butyl, t-butyl, F, Cl, Br, —$(CR'_2)_nOR_6$, —$(CR'_2)_nN(R_6)_2$, —$(CR'_2)_nNR_6COR_7$, —$(CR'_2)_nNR_6SO_2OR_7$, —$(CR'_2)_nNR_6SO_2N(R_6)_2$, —$(CR'_2)_n OSO_2N(R_6)_2$, —$(CR'_2)_nCN$, —$(CR'_2)_nC(NOR_6)R_7$, $NO_2$, —$(CR'_2)_nSO_mR_7$, —$(CR'_2)_nCO_2R_6$, —$(CR'_2)_nCON(R_6)_2$, and Ph.

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicyclic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compound of the invention can exist in unsolvated as well as solvated forms, including hydrated forms. In general, the solvated forms, including hydrated forms and the like are equivalent to the unsolved forms for purposes of the invention.

Certain compounds of the invention may exist in optically active forms. The pure D isomer, pure L isomer, as well as mixtures thereof, including the racemic mixtures, are contemplated by the invention. Additional asymmetric carbon atoms may be present in a substituent such as an alkyl group. All such isomers as well as mixtures thereof are intended to be included in the invention.

The compounds of the invention can be prepared and administered in a wide variety of oral and parenteral dosage forms. If will be obvious to those skilled in the art that the following dosage forms may comprise as the active component, either a compound of Formula I or a corresponding pharmaceutically acceptable salt of a compound of Formula I.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting was, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Such solutions are prepared so as to acceptable to biological systems (isotonicity, pH, etc.). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Topical treatment includes formulations with a vehicle, a base or carrier, carefully selected for the active ingredient. Ointments, creams, lotions, and solutions are included.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit does of preparation may be varied or adjusted from 1 mg to 100 mg according to the particular application and the potency of the active ingredient.

In therapeutic use as agents for treating bacterial infections, the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired. Antibacterial agents can also be used as injectables as in injections for open wounds.

The compounds of the present invention may be prepared through a combination of electrophilic/nucleophilic reactions typically associated with benzene and naphthalene chemistry. This chemistry may be performed on a suitably substituted 1,8-napthalic anhydride 1, which is subsequently converted to the desired 2-hydroxy-benzo[de]isoquinoline-1,3-dione compound 3. Alternatively, the chemical manipulations may be performed directly on the 2-hydroxy-benzo[de]isoquinoline-1,3-dione itself or an a suitable protected derivative 2. The conversion of the anhydrides 1 to the isoquinoline diones is shown in Scheme 1 below.

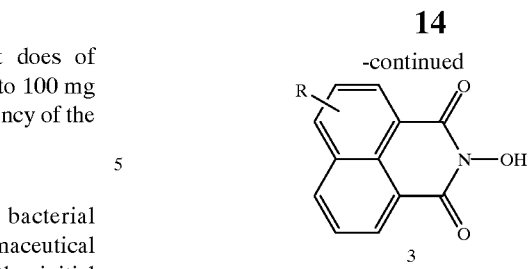

wherein

R is one or more from $R_1$–$R_5$ in Schemes 1–4 and 6–9.

An O-protected hydroxylamine is reacted with the anhydride at 20–100° C. in an alcoholic solvent such as methanol or ethanol with the addition of an inert base such as triethylamine (TEA) or 1,8-diazabicyclo[5.4.0]undec-7-ene (DBU). Aqueous alcohol may also be employed in mixtures varying in the percent alcohol based on solubility of the anhydride. Inert bases may be added or a suitable metal hydroxide such as sodium hydroxide may be used. Still other solvents such as pyridine or dimethylformamide may be employed. The protecting groups employed for the hydroxylamine are generally those typically used for alcohol protection and include benzyl, 4-methoxy benzyl, 3,3,3-trichloroethyl, t-butyl, acetyl, allyl and the like. The protecting groups are generally removed to give 3 with acid, base, or with hydrogenation with palladium on carbon (Pd/C) support. Protecting groups and their removal are chosen to be compatible with the substituents R. Typical acids are hydrochloric acid and trifluoroacetic acid and a typical base is sodium hydroxide. Alternatively, hydroxylamine hydrochloride may be used directly to convert 1 to 3. Typical solvents are alcohols, acetic acid, or pyridine and reaction temperatures are generally 20–120° C.

The 2-hydroxy-benzo[de]isoquinoline-1,3-diones may themselves be protected to enable certain chemical reactions or to enhance solubility (Scheme 2).

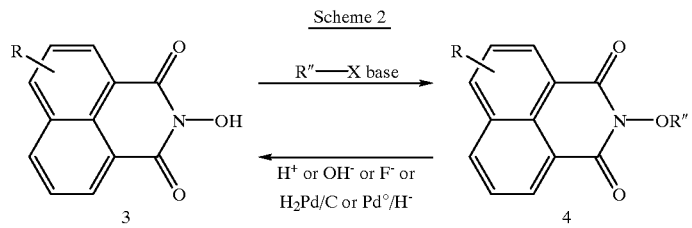

Again, the type of protecting group and its synthesis and removal are generally typical of alcohol chemistry. The protecting groups are represented by R"X where X is a leaving group such as chlorine, bromine, or acetate. R" may be an alkyl based group such as benzyl or 4-methoxy benzyl; an acyl group such as acetyl or benzoyl; or one of several silicon based protecting groups such as trimethyl silyl or t-butyl-dimethylsilyl. The benzyl groups are generally reacted with 3 at 0–100° C. in alcoholic solvent or acetone in the presence of base such as TEA, DBU, sodium carbonate, cesium carbonate or the like. The acyl groups are added to 3 at 0–100° C. using acetyl chloride or acetic anhydride, neat or in inert solvent like benzene, toluene, or methylene chloride. Excess reagent is generally employed and inert bases may be used. The trimethyl silyl or t-butyl-dimethyl silyl are generally added to 3 as their chlorides at 0–50° C. in chlorocarbon solvents such as chloroform or

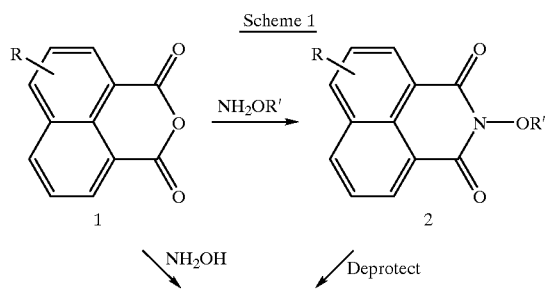

dichloromethane using an inert base such as TEA or the like. The benzyl groups may be removed with hydrogenation using Pd/C or by strong acids such as HBr, HI and the like. Boron tristrifluoroacetate may be used to also cleave benzyl and allyl groups. Allyl groups may also be removed by PhSiH$_3$ with Pd° catalyst. The acetyl groups are removed preferably by aqueous bases such as sodium hydroxide, with alcohol added as needed for solubility at temperatures 25–100° C. The silyl protecting groups may be removed by acids such as HCl, bases such as sodium hydroxide, or by fluoride ion using CsF and the like.

The electrophilic chemistry used to prepare the targeted compounds follows the electrophilic chemistry known for benzene and naphthalene. Each electrophile, once on the ring, helps direct the next electrophile to a specific position. The nitrations are typically conducted on the anhydride 1 and are shown in Scheme 3. These are typically performed at 0–150° C. using sulfuric acid and nitric acid in ratios of 2.5:1, or in glacial acetic acid and nitric acid in a ratio approximately of 10:1. The products 5 or 6 are determined by the R substituent. If the R substituent is a donating group product 6 generally predominates; if R is a withdrawing group, product 5 generally predominates. A specific example is the conversion of 7 to 8 which occurs using sulfuric acid/nitric acid. When fuming nitric acid (stronger conditions) is employed with sulfuric acid and heat, the nitration occurs at the 7- position to give a mixture of 8 and 9. Other examples of regioselective nitrations are the conversion of 10 to 11 and the conversion of 12 to 13.

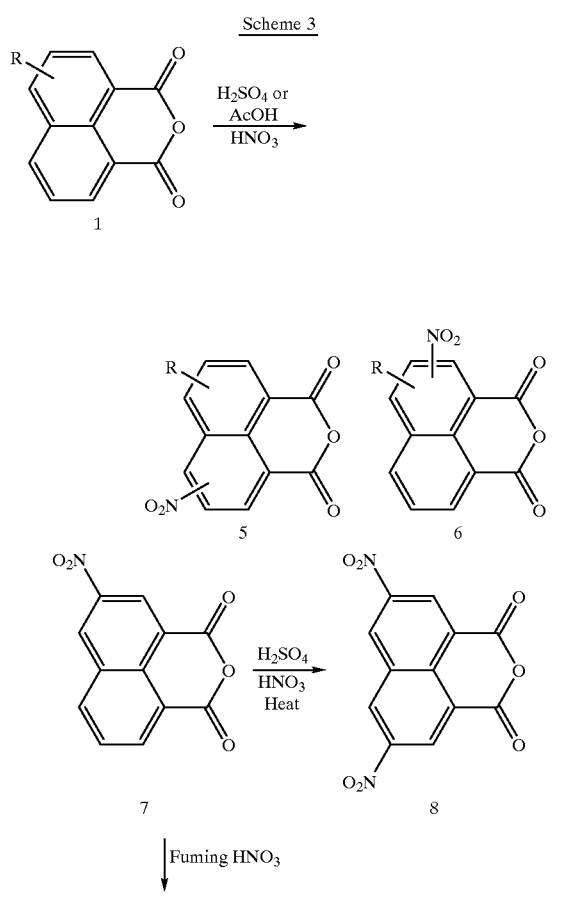

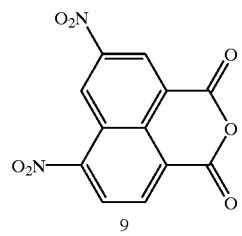

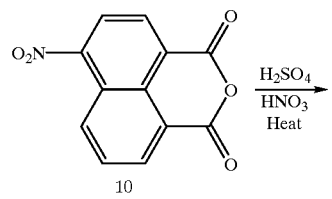

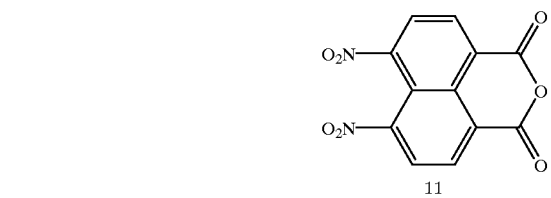

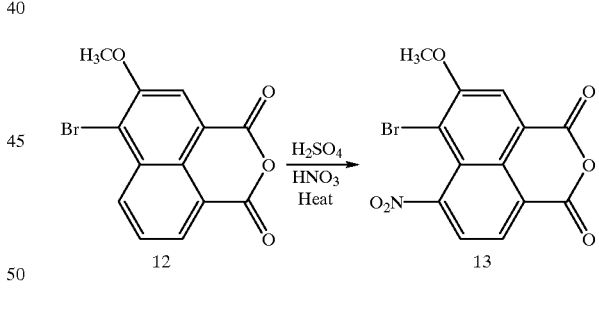

In Scheme 4 typical halogenations are shown. Brominations may be accomplished at 10–100° C. with Br$_2$ or N-bromosuccinimide in halocarbon solvents such as chloroform or dichloromethane, dioxane, or in acetic acid solvent. If more rigorous conditions are required, catalysts such as iron or AlBr$_3$ may be added and the reactions performed in aqueous alcohol (for iron) or carbon disulfide or halocarbon (for AlBr$_3$). Chlorinations are performed using sulfuryl chloride (SO$_2$Cl$_2$) at 30–100° C., neat or in inert solvent such as nitrobenzene or chlorocarbon solvents or with N-chlorosuccinimide in halocarbon solvents. Halogenations may be performed on the anhydride 1 or with the 2-hydroxy derivatives 2 or 3.

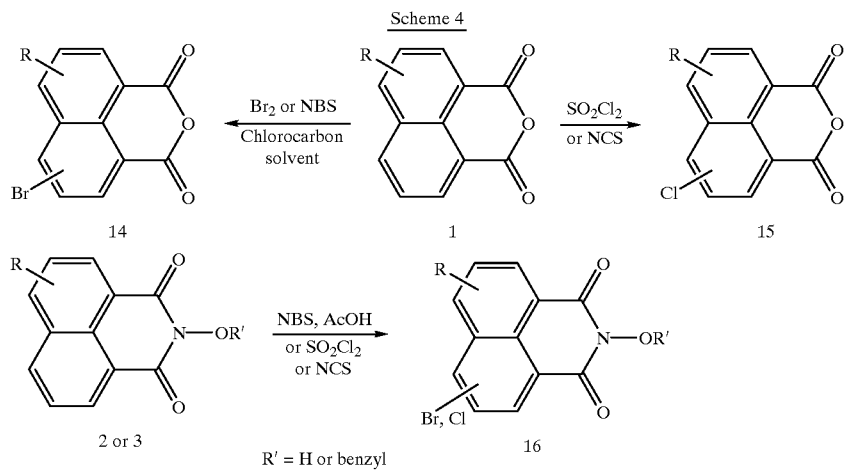

Formylations and aminoformylations are performed when R is a donating substituent as when R is OH in Scheme 5. Formylations are carried out on the anhydrides such as 17a at 25–100° C. using aqueous formaldehyde and acid or paraformaldehyde suspended in acid. Alcohol, dioxane, or tetrahydrofuran may be added as required for solubility. The hydroxymethyl compounds such as 18 may be isolated or permitted to react further to give 19a. Alternatively, the formylations may be performed with an added nucleophile. Thus, 17b can be treated with formaldehyde and an amine at 25–100° C. over several hours (4–96 hours) to give compounds such as 19b.

In a similar manner, N-hydroxymethylacetamide will react with activated rings such as 20 at 10–80° C. to add N-acetyl methylene to the aromatic ring. Amino formylations are also performed using the amine and formaldehyde under conditions described for the formylation above.

Nucleophilic reactions may be performed on halide, triflate, nitro and alkoxy substituents (represented by L) which are para or ortho to electron withdrawing groups. Such displacements (Scheme 6) are generally carried out on the isoquinoline diones 22 where R and R″ are defined as substituents chosen from the $R_1$–$R_5$ specifications at temperatures of 25–180° C. using a nucleophile neat or in an inert solvent.

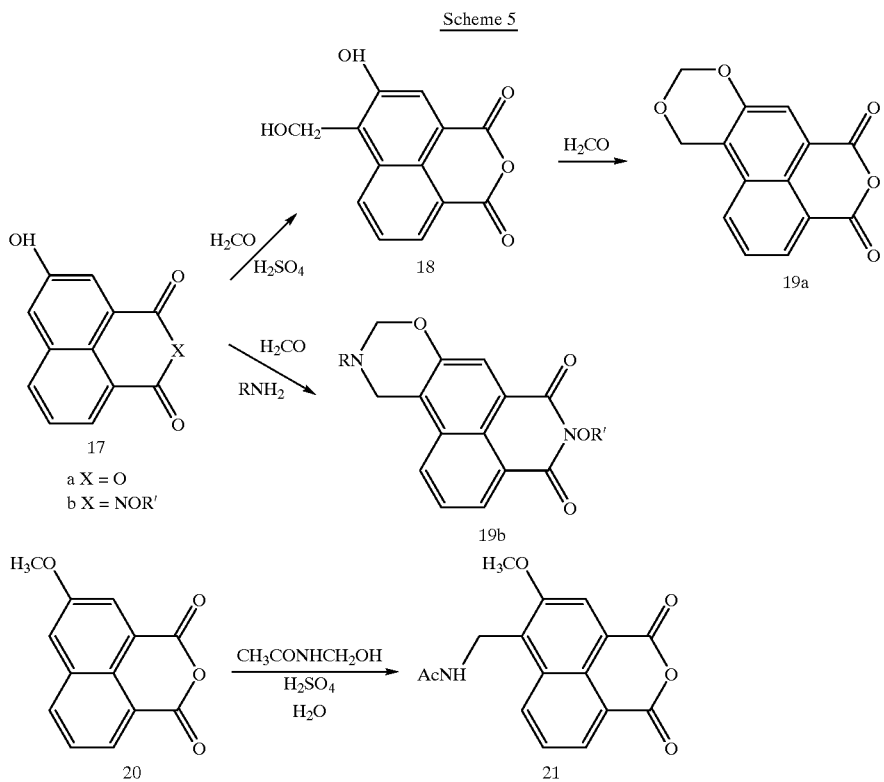

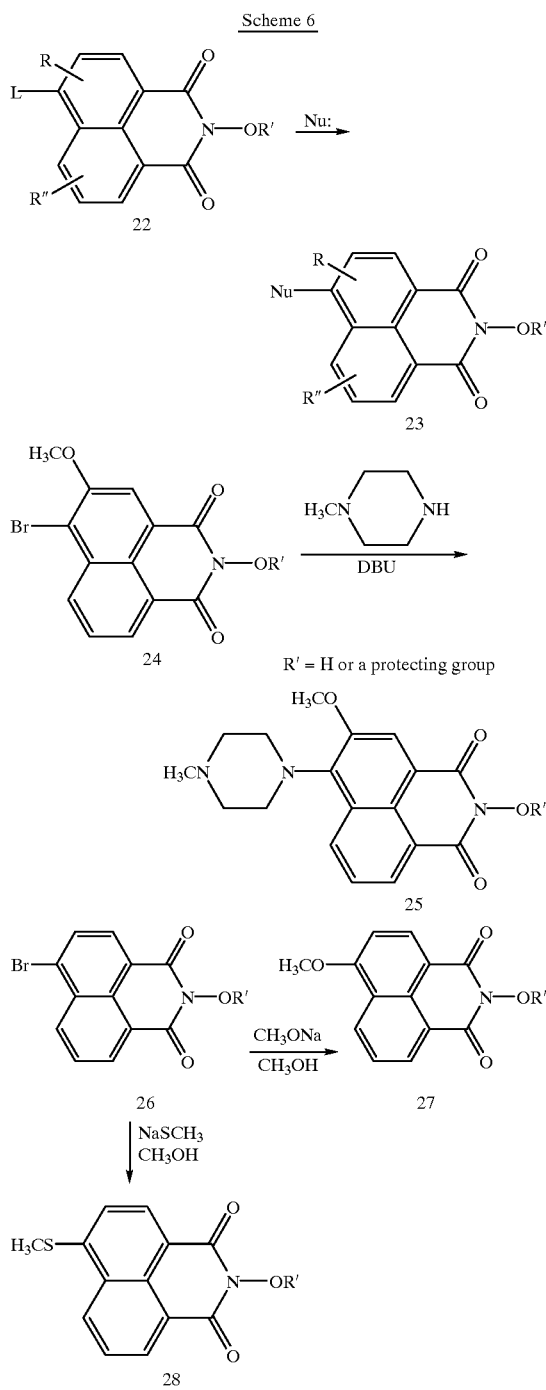

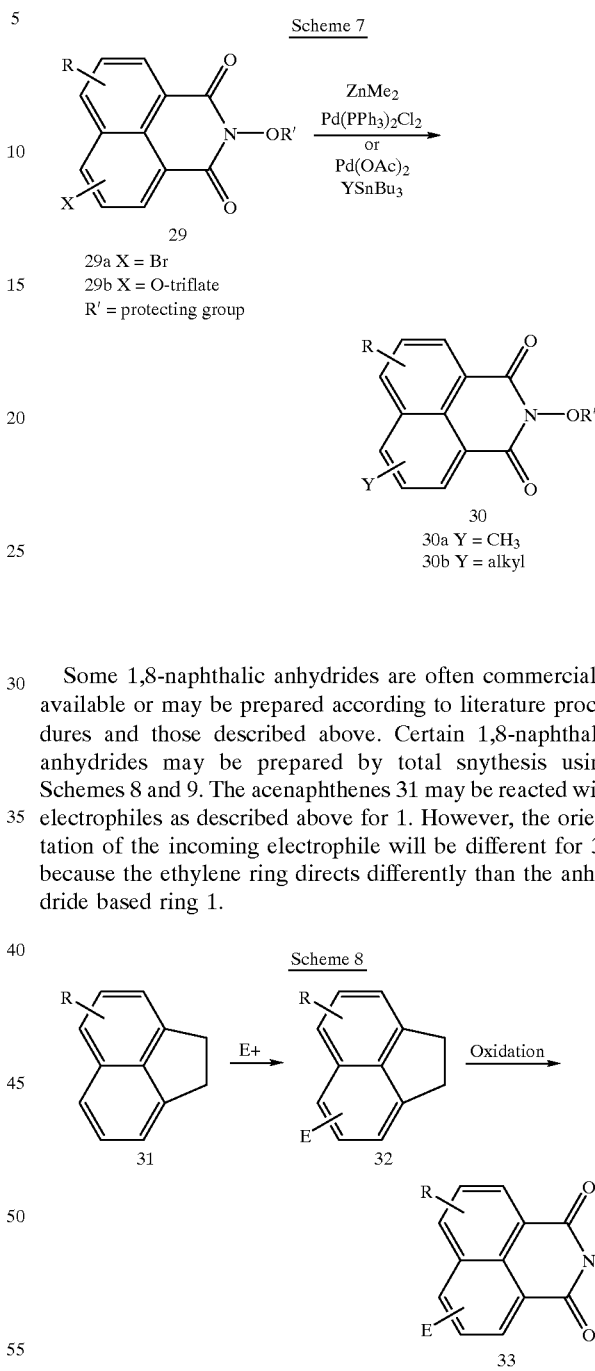

30a or palladium tin couplings may be performed following chemistry well-known in the art to produce 30b where Y is an alkyl group.

Some 1,8-naphthalic anhydrides are often commercially available or may be prepared according to literature procedures and those described above. Certain 1,8-naphthalic anhydrides may be prepared by total snythesis using Schemes 8 and 9. The acenaphthenes 31 may be reacted with electrophiles as described above for 1. However, the orientation of the incoming electrophile will be different for 31 because the ethylene ring directs differently than the anhydride based ring 1.

The product 23 may be deprotected as necessary by the methods described above. The typical nucleophile would be an amine as shown in the conversion of 24 to 25 or an alkoxide (26 to 27) or thiol anion (26 to 28). When amines are employed, a co-base such as DBU, aids the reaction. The alkoxide reactions of 26 to 27 or the thiol anion reactions of 26 to 28 are performed in alcoholic solvents. The alkoxides and thioates are prepared by normal methods in the art.

Halides 29a or triflates 29b may also be replaced by alkyl groups to give 30a, b as shown in Scheme 7. Dimethyl zinc is employed with Pd catalyst at 25° C. using inert etheral solvents such as tetrahydrofuran and diethyl ether to give Once the electrophile has been added ad transformed if desired to give 32, 32 is oxidized to the anhydride 33. The oxidations employ $KMnO_4$, $Na_2Cr_2O_7$, $CrO_3$ and the like and are performed at 0–100° C. in AcOH, aqueous sulfuric acid, and as suspensions in organic solvents such as benzene/water. One advantage of this route is it enables the introduction of "E" to the 2 and 7 positions of the anhydride 33 (positions adjacent to the anhydride grouping).

Scheme 9

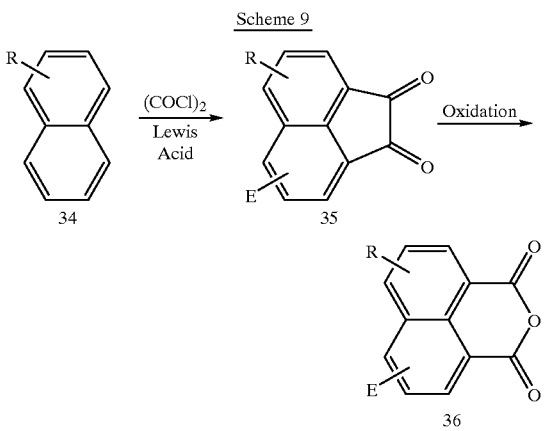

Alternatively, naphthalenes such as 34 (Scheme 9) may be reacted with oxalyl chloride or oxalyl bromide and a catalyst according to "Friedel Crafts" conditions which are well-known in the art to prepare the diketones 35. Typical catalysts would be $AlCl_3$, $TiCl_4$, $BF_3$ and the like. The reactions are carried out in a carbon disulfide, nitrobenzene or halocarbon solvents at −20° C. to 100° C. The product 35 is then oxidized similar to the conditions described for 32 to give 36. In addition, periodate oxidations and peracid oxidations which are well-known in the art may be used to convert 35 to 36.

The compounds prepared by the electrophilic or nucleophilic reactions described above may all be further modified by alkylation, acylation, oxidation and reductions that are all typical of organic chemistry functional group modification. For example, nitro compounds may be reduced to amines with $H_2$ with Pd/C or with $SnCl_2$ or iron filings and acid at 25–100° C. in inert alcoholic or aqueous alcoholic solvents. The amines may be diazotized with sodium nitrite at low temperatures and may be converted to fluoride, bromide, chloride, phenol, and CN, all by chemistry well-known in the art.

The following examples are for illustrative purposes only.

EXAMPLE A-1

2-tert-Butyldimethylsilyoxy-5-nitro-benzo[de]isoquinoline-1,3-dione

Triethyl amine (0.4 g, 4.0 mmol) and tert-butyldimethylsilyl chloride (0.6 g, 4.0 mmol) were added to a solution of 2-hydroxy-5-nitro-benzo[de]isoquinoline-1,3-dione (1.0 g, 3.9 mmol, from Example 1) in chloroform (10 mL). The mixture was stirred at room temperature for 3 hours and concentrated in vacuo to give a dark residue. Column chromatography (silica gel 2% methanol in chloroform) gave 1.1 g of the title compound.

EXAMPLE A-2

2-tert-Butyldimethylsilyoxy-5-nitro-benzo[de]isoquinoline-1,3-dione

O-(tert-Butyldimethyl-silyl)hydroxylamine (1.8 g, 12.3 mmol) was added to a solution of 3-nitro-1,8-naphthalic anhydride (2.0 g, 8.2 mmol) in 50 mL of pyridine. The solution was refluxed for 4 hours and concentrated in vacuo. Purification as described in Example A-1 gave 2.6 g of the title compound.

EXAMPLE B

5-Amino-2-tert-butyldimethylsilyoxy-5-nitro-benzo[de]isoquinoline-1,3-dione

The hydrogenation of 2-tert-butyldimethylsilyoxy-benzo[de]isoquinoline-1,3-dione (1.0 g, 2.7 mmol, from Example A-1 or A-2) at 40 psi in the presence of 10% Pd/C catalyst (1.0 g) in ethyl acetate (20 mL) afforded 0.8 g of the title compound.

EXAMPLE C

3-Amino-1,8-naphthalic anhydride

A solution of tin(II) chloride (10.0 g, 52.7 mmol) in concentrated hydrochloric acid (75 mL) was added to a suspension of 3-nitro-1,8-naphthalic anhydride (4.0 g, 16.5 mmol) in acetic acid (75 mL). The mixture was refluxed with stirring for 2 hours and cooled. The solids formed were filtered and dried to yield 3.1 g of the title compound.

EXAMPLE D

2-Benzyloxy-5-nitro-benzo[de]isoquinoline-1,3-dione

O-Benzyl hydroxylamine hydrochloride (0.8 g, 6.5 mmol) was added to a suspension of 3-nitro-1,8-naphthalic anhydride (1.0 g, 4.1 mmol) in pyridine (20 mL). The mixture was refluxed for 3 hours and concentrated in vacuo. The solid residue obtained was purified by column chromatography (silica gel using 2% methanol in chloroform). Fractions containing the target compound were combined, concentrated, and dried to give 1.3 g of the title compound. mp 239–241° C.;

$^1$H NMR (DMSO-$d_6$): δ9.5 (1H, d, J=2.3), 9.0 (1H, d, J=2.3), 8.8(1H, dd, J=8.0, 0.9), 8.7(1H, dd, J=7.4, 1.0), 8.1(1H, dd, J=8.0, 7.4), 7.7 (2H, m), 7.4 (3H, m), 5.2 (2H, s).

EXAMPLE E

5-Acetamido-N-2-acetoxy-benzo[de]isoquinoline-1,3-dione

Triethylamine (0.2 g, 2.0 mmol) and acetic anhydride (0.2 g, 2.0 mmol) were added to a solution of 5-amino-2-tert-butyldimethylsilyoxy-benzo[de]isoquinoline-1,3-dione (0.2 g, 0.6 mmol, from Example B) in dichloromethane (20 mL). The solution was stirred at room temperature for 1 hour and concentrated in vacuo to give a crude product which was purified by column chromatography (silica gel using 5% methanol in dichloromethane). Fractions containing the target compound were combined, concentrated, and dried to give 0.1 g of the title compound, mp 287–290° C.;

$^1$H NMR (DMSO-$d_6$): δ10.7 (1H, s), 8.9 (1H, d, J=2.0), 8.7 (1H, d, J=2.0), 8.5–8.4 (2H, m), 7.9 (1H, dd, J=8.0, 7.8), 2.5 (3H, s), 2.2 (3H, s).

EXAMPLE F

3-Trifluoromethanesulfonyloxy-1,8-naphthalic anhydride

Trifluoromethanesulfonic anhydride (1.7 g, 6.0 mmol) was added dropwise to a cold solution of 3-hydroxy-1,8-naphthalic anhydride (0.8 g, 3.6 mmol) in pyridine (40 mL) at 0° C. After the addition, the mixture was warmed to 80° C. and stirred for 2 hours. The solution was cooled and poured into ice water. The resulting precipitate was filtered, washed with water, and dried to give 0.9 g of the title compound.

EXAMPLE G

5-Dimethylthiocarbamoyloxy-2-benzyloxy-benzo[de]isoquinoline-1,3-dione

A solution of excess dimethylthiocarbamoyl chloride in DMF (20 mL) was added to a mixture of 2-benzyloxy-5- hydroxy-benzo[de]isoquinoline-1,3-dione (3.5 g, 11.0 mmol) and sodium hydroxide (0.9 g, 22 mmol) in water (50 mL) at 0° C. The mixture was stirred vigorously at room temperature for 2 hours. The solid formed was filtered, washed with water, and dried. The crude product (0.5 g) was purified by column chromatography (silica gel using 2% methanol in chloroform). Fractions containing the target compound were combined, concentrated, and recrystallized from chloroform:ether mixture to give 0.3 g of the title compound, mp 211–214° C.;

$^1$H NMR (CDCl$_3$): 8.6 (1H, dd, J=7.3, 1.0), 8.3 (1H, d, J=2.4), 8.1 (1H, dd, J=7.4, 1.0), 7.9 (1H, d, J=2.4 ), 7.7 (1H, dd, J=7.4, 7.3), 7.6 (2H, m), 7.4 (3H, m), 5.2 (2H, s), 3.5(3H, s), 3.4 (3H, s).

EXAMPLE H

3-Fluror-1,8-naphthalic anhydride

Pyridine:HF (10 mL) was added to 3-amino-1,8-naphthalic anhydride (0.5 g, 2.3 mmol) and sodium nitrite (0.3 g, 3.7 mmol) in a cooled steel vessel at −50° C. The vessel was closed tightly and heated to 140° C. for 2 hours, cooled to room temperature, and the solution was poured into ice water. The resulting precipitate was filtered, washed with water, and dried to give 0.3 g of the title compound.

EXAMPLE I

4-Fluror-1,8-naphthalic anhydride

4-Amino-1,8-naphthalic anhydride (0.8 g, 3.9 mmol) and sodium nitrite (0.4 g, 5.8 mmol) were reacted in pyridine:HF (10 mL) following the procedure of Example H. The product was precipitated with water, filtered, and was purified by column chromatography (silica gel using 50% chloroform in acetone) to give 0.2 g of the title compound.

EXAMPLE J

3Methoxy-1,8-naphthalic anhydride

Dimethylsulfate (2 mL) and potassium carbonate (4.0 g, 29.0 mmol) were added to a suspension of 3-hydroxy-1,8-naphthalic anhydride (1.0 g, 4.7 mmol) in acetone (75 mL). The mixture was refluxed for 8 hours and concentrated. The solid residue was dissolved in water and acidified with concentrated HCl to pH of about 4. The resulting solid was filtered, washed with water, and dried to give 0.9 g of the title compound.

EXAMPLE K

3-Ethoxy-1,8-naphthalic anhydride

3-Hydroxy-1,8-naphthalic anhydride (0.5 g, 2.4 mmol), potassium carbonate (1,3 g, 9.4 mmol), and ethyl bromide (0.8 mL, 10.7 mmol) were reacted in acetone (50 mL) at 40° C. following the procedure of Example J, to give 0.15 g of the title compound.

EXAMPLE L 4-(4-Methylpiperazinyl)-1,8-naphthalic anhydride

4-Methylpiperazine (0.6 g, 6.6 mmol) and DBU (1 mL) were added to 4-bromo-1,8-naphthalic anhydride (1.5 g, 5.4 mmol) in pyridine (10 mL). The solution was refluxed for 8 hours, concentrated in vacuo, and the residue was triturated with water. The separated solid was filtered and dried to give 0.8 g of the title compound.

EXAMPLE M

2-Benzyloxy-6-bromo-benzo[de]isoquinoline-1,3-dione

O-Benzyl hydroxylamine hydrochloride (2.0 g, 12.5 mmol) and 4-bromo-1,8-naphthalic anhydride (2.9 g, 10.5 mmol) were reacted in pyridine (50 mL) following the procedure of Example D to give 3.5 g of the title compound.

EXAMPLE N

3-Bromo-1,8-naphthalic anhydride

Bromine (8.2 g, 51.3 mmol) was added to a solution of 1,8-naphthalic anhydride (10.0 g, 50.5 mmol) in 70% nitric acid (200 mL) at 25° C. The mixture was stirred at 70° C. for 2 hours and cooled overnight. The solids that separated were filtered, washed with water, and dried to give 2.0 g of the title compound (Reference: *J. C. S.*, 1938:1764–1767).

EXAMPLE O

2Benzyloxy-5-bromo-benzo[de]isoquinoline-1,3-dione

O-Benzyl hydroxylamine hydrochloride (0.9 g, 5.6 mmol) and 3-bromo-1,8-naphthalic anhydride (1.3 g, 4.7 mmol, from Example N) were reacted in pyridine (30 mL) following the procedure of Example D to give 1.6 g of the title compound.

EXAMPLE P

2-Benzyloxy-5-methyl-benzo[de]isoquinoline-1,3-dione

Dimethylzinc (4 mL, 2 eq.) was added to a suspension of 2-benzyloxy-5-bromo-benzo[de]isoquinoline-1,3-dione (1.5 g, 3.9 mmol, from Example O) and Pd(PPh$_3$)$_2$Cl$_2$(0.14 g, 0.2 mmol) in dry THF (20 mL). The mixture was stirred under nitrogen at room temperature for 8 hours, filtered, and washed with dimethylacetamide. Concentration of the filtrate gave 1.1 g of the title compound in crude form which was used as is.

EXAMPLE Q

4-Amino-3-bromo-1,8-naphthalic anhydride

Bromine (0.5 g, 3.1 mmol) was added to a suspension of 4-amino-1,8-naphthalic anhydride (0.25 g, 1.2 mmol) in dichloromethane (10 mL). The mixture was stirred at room temperature for 12 hours. The solids were filtered and dried to give 0.32 g of the title compound (Reference: *Bioorganic & Medicinal Chemistry Letters*, 1993;13(4):555–556).

EXAMPLE R

4-Amino-3-chloro-1,8-naphthalic anhydride

Sulfuryl chloride (0.1 mL, 1.1 mmol) was added to suspension of 4-amino-1,8-naphthalic anhydride (0.14 g, 0.7 mmol) in toluene (5 mL). The solution was heated at 70° C. for 8 hours under stirring. The solid formed was filtered and dried to give 0.1 g of the title compound.

EXAMPLE S

4-Chloro-3-nitro-1,8-naphthalic anhydride

Mixture of concentrated sulfuric acid (2.7 mL) and concentrated nitric acid (2.0 mL) was added to a solution of 4-chloro-1,8-naphthalic anhydride (3.0 g, 12.8 mmol) in concentrated sulfuric acid (10.5 mL) at 0° C. The mixture was stirred at room temperature for 2 hours and poured into ice water (50 mL). The separated solid was filtered, washed with water, and dried to give 2.1 g of the title compound (Reference: *Tet.*, 1995;51(33):9127–9138).

EXAMPLE T

3-Amino-4-chloro-1,8-naphthalic anhydride

Hydrogenation of 4-chloro-3-nitro-1,8-naphthalic anhydride (2.0 g, 7.2 mmol, from Example S) in the presence of 10% Pd/C (1.2 g) in DMA (50 mL) afforded 0.6 g of the title compound.

EXAMPLE T-B

3-Amino-4-chloro-1,8-naphthalic anhydride. Procedure B.

Sulfuryl chloride (0.2 mL, 2.2 mmol) was added dropwise with stirring to a suspension of 3-amino-1,8-naphthalic anhydride (0.28 g, 1.4 mmol from Example C) in toluene (10 mL). The mixture was kept at 80° C. overnight. The solvent was removed under reduced pressure. The solid residue was dissolved in acetone (50 mL) and filtered. The filtrate was concentrated to dryness to give 255 mg of the title compound, which could be used for the next step without further purification.

EXAMPLE U

3-Hydroxy-4-nitro-1,8-naphthalic anhydride

A solution of 70% nitric acid (1 mL) and acetic anhydride (3 mL) was added to a suspension of 3-hydroxy-1,8-naphthalic anhydride (1.8 g, 8.4 mmol) in acetic anhydride (10 mL) at 0° C. The mixture was stirred at room temperature for 2 hours. The solution was poured into ice water, and the solids formed were filtered and dried to give 1.0 g of the title compound.

EXAMPLE V

2-Benzyloxy-5-hydroxy-6-nitro-benzo[de]isoquinoline-1,3-dione

3Hydroxy-4-nitro-1,8-naphthalic anhydride (0.9 g, 3.8 mmol, from Example U) and O-benzyl hydroxylamine hydrochloride (0.24 g, 5.0 mmol) were reacted in pyridine (10 mL) following the procedure of Example D. The crude product obtained was purified by column chromatography (silica gel using 5% methanol in dichloromethane) to give 1.0 g of the title compound.

EXAMPLE W

2-Benzyloxy-5-methoxy-6-nitro-benzo[de]isoquinoline-1,3-dione

Methylation of 2-benzyloxy-5-hydroxy-6-nitro-benzo[de]isoquinoline-1,3-dione (0.24 g, 0.7 mmol, from Example V) was accomplished following the procedure of Example J using potassium carbonate (0.3 g, 2.2 mmol), and dimethyl sulfate (0.3 g, 2.1 mmol) in acetone (40 mL) to give 0.2 g of the title compound.

EXAMPLE X

4-Bromo-3-hydroxy-1,8-naphthalic anhydride

Bromine (12.5 mL, 242 mmol) was added to suspension of 3-hydroxy-1,8-naphthalic anhydride (20.37 g, 93.0 mmol) in dioxane (500 mL) at room temperature. The mixture was refluxed for 2.5 hours, dioxane (300 mL) was evaporated in vacuo, and the residue was triturated with water (600 mL). The solids were filtered, washed with water, and dried to give 27.9 g of the title compound.

EXAMPLE Y

2-Benzyloxy-6-bromo-5-hydroxy-benzo[de]isoquinoline-1,3-dione

4-Bromo-3-hydroxy-1,8-naphthalic anhydride (3.41 g, 11.6 mmol, from Example X) and O-benzyl hydroxylamine hydrochloride (2.8 g, 17.5 mmol) were reacted in pyridine (50 mL) following the procedure of Example D to give 3.5 g of the title compound.

EXAMPLE Z

2-Benzyloxy-6-bromo-5-methoxy-benzo[de]isoquinoline-1,3-dione

2-Benzyloxy-6-bromo-5-hydroxy-benzo[de]isoquinoline-1,3-dione (2.0 g, 5.0 mmol, from Example Y), potassium carbonate (2.75 g, 20.0 mmol), and dimethyl sulfate (2.7 g, 21.0 mmol) were reacted in acetone (300 mL) following the procedure as described in Example J to give 1.9 g of the title compound.

EXAMPLE A1

4-(2-Chloroacetamide)-methyl-3-hydroxy-1,8-naphthalic anhydride

A mixture of 3-hydroxy-1,8-naphthalic anhydride (1.30 g, 6.1 mmol) and 2-chloro-N-hydroxymethyl acetamide (0.82 g, 6.6 mmol) in concentrated sulfuric acid (7 mL) was stirred at room temperature for 2 hours. The resulting mixture was poured into ice water. The precipitate was filtered, washed with water, and dried to give 0.8 g of the title compound.

EXAMPLE B 1

4-Aminomethyl-3-hydroxy-1,8-naphthalic anhydride, Hydrochloride

A solution of 30% HCl in ethanol (50 mL) was added to 4-(2-chloroacetamido)-methyl-3-hydroxy-1,8-naphthalic anhydride (0.2 g, 0.6 mmol, from Example A1). The mixture was refluxed for 4 hours and the precipitate formed was filtered and dried to give 0.14 g of the title compound.

EXAMPLE C1

4-Acetamidomethyl-3-hydroxy-1,8-naphthalic anhydride

3-Hydroxy-1,8-naphthalic anhydride (3.0 g, 14.0 mmol) was reacted with N-hydroxymethyl acetamide (1.6 g, 18.0 mmol) in concentrated sulfuric acid (14 mL) following the procedure of Example A1 to give 3.2 g of the title compound.

EXAMPLE D1

4-Acetamidomethyl-3-methoxy-1,8-naphthalic anhydride

N-hydroxymethylacetamide (0.14 g, 1.6 mmol) was reacted with 3-methoxy-1,8-naphthalic anhydride (0.33 g, 1.5 mmol, from Example J) in concentrated sulfuric acid (1.6 mL) following the procedure of Example A1 to give 0.36 g of the title compound.

EXAMPLE E1

4-(2-Chloroacetamido)-methyl-3-methoxy-1,8-naphthalic anhydride

3-Methoxy-1,8-naphthalic anhydride (1.1 g, 4.8 mmol, from Example J) was reacted with 2-chloro-N-hydroxymethylacetamide (0.6 g, 4.8 mmol) in concentrated sulfuric acid (5.2 mL) by following the procedure as described in Example A1 to give 1.5 of the title compound.

EXAMPLE F1

4-Aminomethyl-3-methoxy-1,8-naphthalic anhydride

The 4-(2-chloroacetamido)-methyl-3-methoxy-1,8-naphthalic anhydride (1.1 g, 3.3 mmol, from Example E1) was hydrolyzed in refluxing 30% HCl in ethanol (150 mL) for 8 hours following the procedure in Example E1 to give 0.8 g of the title compound.

EXAMPLE G1

3,6-Dinitro-1,8-naphthalic anhydride

A mixture of concentrated sulfuric acid (36.0 mL) and fuming nitric acid (8.0 mL) was added dropwise with stirring at 0° C. to a solution of 3-nitro-1,8-naphthalic anhydride (12.0 g, 50 mmol) in concentrated sulfuric acid (36.0 mL). After the complete addition, the reaction mixture was heated to 60° C. for 1 hour, cooled, and poured into ice water. The resulting solids were filtered and recrystallized from toluene to give 10.0 g of the title compound.

EXAMPLE H1

2-tert-Butyldimethyl-silyloxy-5,8-dinitro-benzo[d]isoquinoline-1,3-dione

O-(tert-Butyldimethyl-silyl)hydroxylamine (1.8 g, 12.2 mmol) was added to a suspension of 3,6-dinitro-1,8-naphthalic anhydride (2.4 g, 8.3 mmol) in toluene (100 mL). The reaction mixture was refluxed with stirring for 3 hours, and concentrated in vacuo. Crystallization from chloroform gave 1.87 g of the title compound.

EXAMPLE I1

2-tert-Butyldimethyl-silyloxy-5,8-diamino-benzo[de]isoquinoline-1,3-dione

Hydrogenation of 2-tert-butyldimethyl-silyloxy-5,8-dinitro-benzo[de]isoquinoline-1,3-dione from Example H1, following the procedure of Example B afforded 1.6 g of the title compound.

EXAMPLE J1

2-Acetoxy-5,8-diacetamido-benzo[de]isoquinoline-1,3-dione

Triethyl amine (0.5 g, 4.6 mmol) and acetic anhydride (0.5 g, 4.6 mmol) were added to a solution of 2-tert-butyldimethyl-silyloxy-5,8-diamino-benzo[de]isoquinoline-1,3-dione (0.5 g, 1.5 mmol, from Example I1) in dichloromethane (20 mL). The reaction mixture was heated at 60° C. with stirring for 2 hours and concentrated in vacuo. The solid residue was triturated with water, and the solids formed were filtered, washed with ether, and dried to give 0.6 g of the title compound.

EXAMPLE K1

11H-5,8,10-Trioxabenzo[de]anthracene-4,6-dione

Paraformaldehyde (16.0 g, 530.0 mmol) and concentrated sulfuric acid (80 mL) were added to a suspension of 3-hydroxy-1,8-naphthalic anhydride (10.24 g, 48.0 mmol) in dioxane (500 mL). The mixture was heated to 80° C. for 2 hours under stirring. After cooling, the reaction mixture was poured into ice water (1000 mL). The precipitate was filtered and dried to give 12.0 g of the title compound.

EXAMPLE L1

11H, 11-Methoxy-5,8,10-trioxabenzo[de]anthracene-4,6-dione

Bromine (0.3 mL, 5.8 mmol) was added to a suspension of 11H-5,8,10-trioxabenzo[de]anthracene-4,6-dione (0.3 g, 1.2 mmol, from Example K1) in chloroform (20 mL). The mixture was refluxed for 3 hours under nitrogen atmosphere. Methanol (10 mL) was added and the reaction mixture refluxed for additional 3 hours and concentrated in vacuo. The solids obtained were washed with methanol and dried to give 0.16 g of the title compound.

EXAMPLE M1

3-Methoxy-4-nitro-1,8-naphthalic anhydride

Concentrated sulfuric acid (0.05 mL) was added to a solution of 3-methoxy-1,8-naphthalic anhydride (2.25 g, 10.40 mmol, from Example J) in acetic anhydride (120 mL) and 70% nitric acid (5.0 mL). The mixture was stirred at 0° C. for 1 hour and poured into ice water. The precipitate was filtered, washed with water, and dried to give 2.20 g of the title compound.

EXAMPLE N1

4,5-Dinitro-1,8-naphthalic anhydride

A mixture of concentrated sulfuric acid (36 mL), concentrated nitric acid (28 mL), and 70% nitric acid (14.4 mL) was added dropwise to a solution of 4-nitro-1,8-naphthalic anhydride (12.0 g, 49.3 mmol) in concentrated sulfuric acid (36 mL) at 0° C. for 1 hour. After the complete addition, the mixture was heated at 60° C. for 1.5 hours, cooled, and poured into ice water (800 g). The resulting precipitate was filtered, dried, and recrystallized from acetic acid and toluene to give 7.0 g of the title compound.

EXAMPLE O1

3-Methoxy-acenaphthene-1,2-dione

A solution of 2-methoxynaphthalene (5 g, 31.6 mmol) and oxalyl chloride (11 mL, 126 mmol) in 150 mL of dichloromethane was cooled to −15° C. ($CO_2$/ethylene glycol) under nitrogen. Aluminum trichloride (10.5 g, 79 mmol) was added slowly over 30 minutes. After 3 hours, the mixture was poured onto 100 g of ice. The layers were separated, and the aqueous layer was washed with dichloromethane. The combined organic layers were washed with saturated sodium bicarbonate, water, brine and dried over magnesium sulfate. The solution was concentrated to afford 4.5 g of a solid. The solid was triturated with dichloromethane to give 1.24 g of the title compound as a solid, mp 218°–220° C.; $^1$H NMR (DMSO-d$_6$): δ8.38 (d, 1H), 8.25 (d, 1H), 7.90 (d, 1H), 7.63 (m, 2H), 4.07 (s, 3H).

EXAMPLE P1

2-Methoxy-1,8-naphthalic anhydride

Sodium dichromate (0.21 g, 0.71 mmol) was slowly added for a refluxing solution of 3-methoxy-acenaphthene-1,2-dione (0.1 g, 0.47 mmol, from Example O1) in 10 mL of acetic acid. After 2 hours, the solution was poured onto 30 g of ice and stirred until the ice melted. A solid was collected, washed with water and dried to afford 0.07 g of the title compound, mp >250° C.; $^1$H NMR (DMSO-d$_6$): δ8.51 (d, 1H), 8.42 (dd, 2H), 7.75 (s, 1H), 7.69 (t, 1H), 4.10 (s, 3H).

EXAMPLE Q1

2-Acetyl-1,8-naphthalic anhydride

Sodium dichromate (2 g, 6.7 mmol) was slowly added to a refluxing solution of 3-acetyl-acenaphthene (0.5 g, 2.5 mmol) in 20 mL of acetic acid. After 1.5 hours, the solution was cooled and poured onto 60 g of ice and stirred until the ice melted. A solid was collected, washed with water, and dried to afford 0.47 g of the title compound, mp >250° C.; $^1$H NMR (DMSO-d$_6$): δ8.81 (d, 1H), 8.53 (dd, 2H), 8.34 (d, 1H), 7.93 (t, 1H), 2.76 (s, 3H).

EXAMPLE R1-A,B

3-Bromo-4-nitro-1,8-naphthalic anhydride (A) and 3-Bromo-5-nitro-1,8-naphthalic anhydride (B)

A cooled solution of concentrated sulfuric (18 mL) in nitric acid (12 mL) was added dropwise to a solution of 3-bromo-1,8-naphthalic anhydride (25.9 g, 93.5 mmol, as described in *Chem. Abstr.*, 1962;57:5856) in concentrated sulfuric acid (220 mL) at 0° C. The reaction was stirred at 0° C. for 2 hours and added to ice. The precipitate was filtered, washed with water, and dried to give 23.0 g as a mixture of the title compounds.

EXAMPLE S1-A,B

2-Benzyloxy-5-bromo-6-nitro-benzo[de] isoquinoline-1,3-dione (A) and 2-Benzyloxy-5-bromo-7-nitro-benzo[de]isoquinoline-1,3-dione (B)

To a solution of O-benzylhydroxylamine hydrochloride (3.4 g, 22 mmol) in pyridine (250 mL) was added a mixture of 3-bromo-4-nitro-1,8-naphthalic anhydride and 3-bromo-5-nitro-1,8-naphthalic anhydride (6.3 g, 19.6 mmol, from Example R1-A,B). The mixture was refluxed for 3 hours, then concentrated under reduced pressure to give a solid residue. The product was purified by column chromatography on silica with chloroform/hexane (1:1) to give 4.2 g of the title compounds as a mixture. Crystallization of the mixture from chloroform gave 3.6 g of 2-benzyloxy-5-bromo-6-nitro-benzo[de]isoquinoline-1,3-dione (A).

EXAMPLE T1-A,B

2-Benzyloxy-5-bromo-6-(piperidin-1-yl)-benzo[de] isoquinoline-1,3-dione (A) and 2-Benzyloxy-5-bromo-7-(piperidin-1-yl)-benzo[de]isoquinoline-1,3-dione (B)

To a solution of piperidine (0.40 g, 4.7 mmol) in 5 mL of DMF was added a mixture of 2-benzyloxy-5-bromo-6-nitro-benzo[de]isoquinoline-1,3-dione (A) and 2-benzyloxy-5-bromo-7-nitro-benzo[de]isoquinoline-1,3-dione (B) (0.50 g, 1.2 mmol, from Example S1-A,B). The reaction was heated to 120° C. for 4 hours, cooled, and the solvent removed under vacuum. The residue was chromatographed using chloroform/ethyl acetate (10:1) to give a mixture of the title compounds which were separated by crystallization from chloroform/hexane/ethyl acetate (5:5:1) to give 0.27 g of 2-benzyloxy-5-bromo-6-(piperidin-1-yl)-benzo[de] isoquinoline-1,3-dione (A) and 0.10 g of 2-benzyloxy-5-bromo-7-(piperidin-1-yl)-benzo[de]isoquinoline-1,3-dione (B).

EXAMPLE U1

2-Benzyloxy-5-bromo-6-(3-methyl-piperidin-1-yl)-benzo[de]isoquinoline-1,3-dione

To a solution of 2-benzyloxy-5-bromo-6-nitro-benzo[de] isoquinoline-1,3-dione (0.50 g, 1.2 mmol, from Example S1-A) in DMF (5 mL) was added 3-methylpiperidine (0.47 g, 4.7 mmol). The reaction was reacted at 120° C. for 5 hours, cooled, and concentrated under vacuum. The resulting residue was purified by column chromatography on silica gel using hexane/ethyl acetate (5:1) to give 0.50 g of the title compound.

EXAMPLE V1

2-Benzyloxy-5-bromo-6-(4-methylpiperazin-1-yl)-benzo[de]isoquinoline-1,3-dione

Following the procedure of Example U1,2-benzyloxy-5-bromo-6-nitrobenzo[de]isoquinoline-1,3-dione (0.50 g, 1.2 mmol, from Example S1-A) and 1-methylpiperazine (0.46 g, 4.7 mmol) in DMF (5 mL) were reacted to give 0.22 g of the title compound.

EXAMPLE W1

2-Benzyloxy-5-bromo-6-(pyrrolidin-1-yl)-benzo[de] isoquinoline-1,3-dione

To a solution of 2-benzyloxy-5-bromo-6-nitro-benzo[de] isoquinoline-1,3-dione (0.25 g, 0.59 mmol, from Example S1-A) in DMF (5 mL) was added pyrrolidine (0.05 g, 0.70 mmol) and triethyl amine (0.18 g, 1.8 mmol). The reaction was reacted at 85° C. for 24 hours, cooled, and concentrated under vacuum. The residue was triturated with methanol to give 0.24 g of the title compound.

EXAMPLE X1

2-Benzyloxy-5-bromo-6-dimethylamino-benzo[de] isoquinoline-1,3-dione

A mixture of 2-benzyloxy-5-bromo-6-nitro-benzo[de] isoquinoline-1,3-dione (0.21 g, 0.48 mmol, from Example S1-A), dimethylamine (0.60 g, 13.0 mmol) and triethyl amine (0.11 g, 1.1 mmol) in DMF (20 mL) were reacted at 120° C. in a pressure reactor for 10 hours. The reaction mixture was cooled and concentrated under reduced pressure. The residue was filtered through silica gel using CHCl$_3$ to give 0.17 g of the title compound.

EXAMPLE Y1

(S)-[1-(2-Benzyloxy-5-bromo-1,3-dioxo-2,3-dihydro-1H-benzo[de]isoquinolin-6-yl)-pyrrolidin-3-yl]-carbamic acid, tert-butyl ester Following the procedure of Example W1, 2-benzyloxy-5-bromo-6-nitro-benzo[de]isoquinoline-1,3-dione (0.40 g, 0.94 mmol, from Example S1-A), (S)-pyrrolidin-3-yl-carbamic acid, tert-butyl ester (0.38 g, 2.1 mmol) and triethyl amine (0.18 g, 1.9 mmol) in DMF (5 mL) were reacted at 80° C. for 48 hours to give 0.43 g of the title compound.

EXAMPLE Z1

5-Amino-2-benzyloxy-6-chloro-benzo[de]isoquinoline-1,3-dione

Following the procedure of Example D, 3-amino-4-chloro-1,8-naphthalic anhydride (14.0 g, 60.1 mmol, from Example T), pyridine (500 mL), and O-benzylhydroxylamine hydrochloride (15.0 g, 60.1 mmol) were reacted to give 18.0 g of the title compound.

EXAMPLE A2

2-Benzyloxy-6-chloro-5-cyano-benzo[de]isoquinoline-1,3-dione

To a solution of 5-amino-2-benzyloxy-6-chloro-benzo[de]isoquinoline-1,3-dione (4.8 g, 13 mmol, from Example Z1) and $BF_3 \cdot OEt_2$ (18.0 g, 130 mmol) in THF (250 mL) at 0° C. was added dropwise tert-butyl nitrite (18.7 g, 18.2 mmol). The resulting precipitate was filtered, washed with THF, and dried to give 4.2 g of the diazonium tetrafluoroborate salt. This material was used in the next step without further purification.

To a rapidly stirred solution of CuCN (8.4 g, 94 mmol), NaCN (5.6 g, 120 mmol), and $NaHCO_3$ (2.4 g, 28 mmol) in water (500 mL) at 0° C. was added a suspension of the diazonium tetrafluoroborate salt (from above) in acetonitrile (150 mL). The reaction was stirred at 0° C. for 15 minutes, extracted with chloroform, dried, filtered, and the solvent removed under vacuum. Chromatography of the residue on silica using chloroform/hexane (5:1) gave 1.7 g of the title compound.

EXAMPLE B2

2-Benzyloxy-5-cyano-6-(pyrrolidin-1-yl)-benzo[de]isoquinoline-1,3-dione

To a solution of pyrrolidine (0.070 g, 0.98 mmol) and triethyl amine (0.11 g, 1.1 mmol) in acetonitrile (5 mL) at reflux was added 2-benzyloxy-6-chloro-5-cyano-benzo[de]isoquinoline-1,3-dione (0.20 g, 0.55 mmol, from Example A2). The reaction was heated at reflux for 20 minutes, then cooled to 0° C. The resulting precipitate was removed by filtration, washed with cold acetonitrile, and dried to give 0.15 g of the title compound.

EXAMPLE C2

2-Benzyloxy-5-cyano-6-(morpholin-1-yl)-benzo[de]isoquinoline-1,3-dione

Following the procedure of Example B2, 2-benzyloxy-6-chloro-5-cyano-benzo[de]isoquinoline-1,3-dione (0.20 g, 0.55 mmol, from Example A2), morpholine (0.096 g, 1.1 mmol), and triethyl amine (0.11 g, 1.1 mmol) in acetonitrile (5 mL) at 50° C. for 2 hours were reacted to give 0.15 g of the title compound.

EXAMPLE D2

2-Benzyloxy-5-cyano-6-(piperidin-1-yl)-benzo[de]isoquinoline-1,3-dione

Following the procedure of Example B2, 2-benzyloxy-6-chloro-5-cyano-benzo[de]isoquinoline-1,3-dione (0.20 g, 0.55 mmol, from Example A2), piperidine (0.11 g, 1.1 mmol), and triethyl amine (0.11 g, 1.1 mmol) were reacted at ambient temperature for 5 hours to give 0.17 g of the title compound.

EXAMPLE E2

(S)-[1-(2-Benzyloxy-5-cyano-1,3-dioxo-2,3-dihydro-1H-benzo[de]isoquinolin-6-yl)-pyrrolidin-3-yl]-carbamic acid, tert-butyl ester Following the procedure of Example B2, 2-benzyloxy-6-chloro-5-cyano-benzo[de]isoquinoline-1,3-dione (0.20 g, 0.55 mmol, from Example A2), (S)-pyrrolidin-3-yl-carbamic acid tert-butyl ester (0.11 g, 0.60 mmol), triethyl amine (0.11 g, 1.1 mmol) were reacted at ambient temperature for 5 hours. Column chromatography of the crude product on silica using chloroform/methanol (20:1) gave 0.18 g of the title compound.

EXAMPLE F2

3-Bromo-5-nitro-1,8-naphthalic anhydride

To a solution of 4-nitro-1,8-naphthalic anhydride (5.0 g, 20.6 mmol) in concentrated $H_2SO_4$ (50 mL) was added silver sulfate (6.4 g, 20.6 mmol) and bromine (3.3 g, 20.6 mmol). The mixture was stirred at 55° C. for 2 hours. The cooled reaction mixture was filtered. The filtrate added to ice and the resulting precipitate was collected by filtration, washed with water, and dried to give 6.7 g of the title compound.

EXAMPLE G2

2-Allyloxy-5-bromo-7-(pyrrolidin-1-yl)-benzo[de]isoquinoline-1,3-dione

To a solution of 3-bromo-5-nitro-1,8-naphthalic anhydride (1.0 g, 3.1 mmol, from Example F2) in pyridine (5 mL) was added O-allylhydroxylamine hydrochloride hydrate (0.38 g, 3.4 mmol). The mixture was reacted at 120° C. for 2 hours, the solvent removed under vacuum and the residue partitioned between chloroform and water. The organic layer was washed with water, dried, filtered, and evaporated under vacuum to give 2-allyloxy-5-bromo-7-nitro-benzo[de]isoquinoline-1,3-dione. This material was used in the next step without further purification.

Following the procedure of Example W1, a mixture of the 2-allyloxy-5-bromo-7-nitro-benzo[de] isoquinoline-1,3-dione from above, pyrrolidine (0.43 g, 6.0 mmol) and triethyl amine (1.2 g, 12 mmol) in DMF (10 mL) was reacted to give 0.91 g of the title compound.

EXAMPLE H2

3-Methyl-5-nitro-1,8-naphthalic anhydride

A mixture of 3-bromo-5-nitro-1,8-naphthalic anhydride (3.0 g, 9.3 mmol, from Example F2), $Pd(PPh_3)_4$ (0.43 g, 0.37 mmol), tetramethyl tin (2.48 g, 14.1 mmol) and LiCl (2.0 g, 48 mmol) in toluene (100 mL) was heated at 120° C. in a pressure reactor for 36 hours. The reaction mixture was cooled and partitioned between chloroform and water. The organic layer was washed with water, dried, filtered, and the solvent removed under vacuum. The product was crystallized from chloroform at 0° C. to give 1.6 g of the title compound.

EXAMPLE I2

2-Allyloxy-5-methyl-7-nitro-benzo[de]isoquinoline-1,3-dione

A mixture of 3-methyl-5-nitro-1,8-naphthalic anhydride (1.4 g, 5.4 mmol, from Example H2), O-allylhydroxylamine hydrochloride hydrate (0.78 g, 7.1 mmol) in pyridine (10 mL) was heated to 120° C. for 3 hours and cooled. The precipitate was filtered, washed with cold pyridine, ether, and dried to give 1.1 g of the title compound.

EXAMPLE J2

2-Allyloxy-5-methyl-7-(pyrrolidin-1-yl)-benzo[de]isoquinoline-1,3-dione

Following the procedure of Example W1, 2-allyloxy-5-methyl-7-nitro-benzo[de]isoquinoline-1,3-dione (0.52 g, 1.7 mmol, from Example I2), pyrrolidine (0.23 g, 3.2 mmol), triethyl amine (0.65 g, 6.4 mmol) in DMF (5 mL) were reacted to give 0.55 g of the title compound.

EXAMPLE K2

6-Bromo-2-tert-butyloxy-benzo[de]isoquinoline-1,3-dione

O-tert-Butylhydroxylamine hydrochloride (3.0 g, 23.9 mmol) was added to 4-bromo-1,8-naphthalic anhydride (5.0 g, 18.0 mmol) in pyridine (30.0 mL). the mixture was refluxed for 4 hours, concentrated, and the residue suspended in water. The solid was filtered and dried to give 5.9 g of the title compound.

EXAMPLE L2

[1-(2-tert-butyloxy-2,3-dihydro-1,3-dioxo-1H-benzo[de]isoquinolin-6-yl)-pyrrolidin-3-yl]-carbamic acid, tert-butyl ester A mixture of 6-bromo-2-tert-butyloxy-2,3-dihydro-1H-benzo[de]isoquinoline-1,3-dione (0.5 g, 1.4 mmol, from Example K2) and 3-Boc-aminopyrrolidine (0.8 g, 4.7 mmol) in DMA (4.0 mL) was heated at 120° C. overnight. The mixture was concentrated, and water was added to give a precipitate, which was filtered to yield 0.6 g of the title compound.

EXAMPLE M2

6-Bromo-2-tert-butyloxy-5-methoxy-benzo[de]isoquinoline-1,3-dione

Following the procedure from Example K2, 4-bromo-3-methoxy-1,8-naphthalic anhydride (1.0 g, 3.3 mmol) and O-tert-butylhydroxylamine hydrochloride (0.6 g, 4.8 mmol) were reacted in pyridine (5 mL) to give 1.2 g of the title compound.

EXAMPLE N2

[1-(2-tert-butyloxy-1,3-dioxo-2,3-dihydro-5-methoxy-1H-benzo[de]isoquinolin-6-yl)-pyrrolidin-3-yl]-carbamic acid, tert-butyl ester Following the procedure from Example L2, 6-bromo-5-methoxy-2-tert-butyloxy benzo[de]isoquinoline-1,3-dione (0.5 g, 1.3 mmol, from Example M2) and 3-Boc-aminopyrrolidine (0.5 g, 2.7 mmol) were reacted in pyridine/DBU solution (2:1 mL) to give a mixture of 40% starting material and 60% product. Purification by flash chromatography, eluting with dichloromethane gave 0.2 g of the title compound.

EXAMPLE O2

3-Acetamido-4-chloro-1,8-naphthalic anhydride

To a solution of 3-amino-4-chloro-1,8-naphthalic anhydride (3.0 g, 12.0 mmol, from Example T) in acetic anhydride (50 mL) was added p-toluene sulfonic acid (3.0 g, 15.8 mmol). The mixture was stirred at room temperature overnight. The resulting solid was filtered, washed several times with water, and dried to give 3.0 g of the title compound.

EXAMPLE P2

5-Acetamido-2-tert-butyloxy-6-chloro-benzo[de]isoquinoline-1,3-dione

Following the procedure from Example K2, 3-acetamido-4-chloro-1,8-naphthalic anhydride (2.8 g, 9.7 mmol, from Example O2) and O-tert-butylhydroxylamine hydrochloride (1.6 g, 12.7 mmol) were reacted in pyridine (20 mL) to give 3.0 g of the title compound.

EXAMPLE Q2

5-Acetamido-2-tert-butyloxy-6-(pyrrolidin-1-yl)-benzo[de]isoquinoline-1,3-dione

Pyrrolidine (0.85 g, 12.0 mmol) was added to 5-acetamido-2-tert-butyloxy-6-chloro benzo[de]isoquinoline-1,3-dione (0.30 g, 0.8 mmol, from Example P2). The solution was heated at 100° C. overnight followed by addition of water (10 mL). The precipitate was filtered to give 0.30 g of the title compound.

EXAMPLE R2

3-Nitro-4-(pyrrolidin-1-yl)-1,8-naphthalic anhydride

Pyrrolidine (3.0 mL) and 4-chloro-3-nitro-1,8-naphthalic anhydride (0.5 g, 1.8 mmol, from Example S) were refluxed in absolute ethanol (5.0 mL) for 4 hours. The orange suspension was cooled, filtered, and dried to give 0.56 g of the title compound.

EXAMPLE S2

2-tert-Butyloxy-5-chloro-6-[3-methoxypyrrolidin-1-yl]-benzo[de]isoquinoline-1,3-dione Following the procedure of Example Q2, 3-methoxypyrrolidine (0.2 g, 2.0 mmol) and 2-tert-butyloxy-5,6-dichloro-benzo[de]isoquinoline-1,3-dione (0.4 g, 1.2 mmol, from Example V2) were reacted in DMA (1.0 mL) at 120° C. overnight followed by addition of water (10 mL). The precipitate that formed was filtered to give 0.44 g of the title compound.

EXAMPLE T2

3-Amino-1,8-naphthalic anhydride

Palladium on activated carbon (wet, 10%), (1 g) was added to the solution of 3-nitro-1,8-naphthalic anhydride (10 g, 41 mmol) in N,N-dimethylacetamide (25 mL) in a 500 mL hydrogenation bottle. The resulting suspension was hydrogenated for 4 hours to give 7.9 g of the title compound.

EXAMPLE U2

3,4-Dichloro-1,8-naphthalic anhydride

Concentrated sulfuric acid (16 mL) was placed in a 500 mL three-necked flask and solid sodium nitrite (1.52 g, 22 mmol) was added over a period of 10 to 15 minutes with stirring. After the addition was completed, the temperature was raised to 70° C., and the mixture was stirred until all the sodium nitrite dissolved. The solution was cooled to 25° C., to 30° C. with an ice bath, and a solution of 3-amino-4-chloro-1,8-naphthalic anhydride (4.95 g, 20 mmol, from Example T-B) in 40 mL of hot glacial acetic acid was added slowly, with stirring, at such a rate that the temperature remained below 40° C. for 0.5 hour. A solution of cuprous chloride (4.4 g, 44 mmol) in concentrated hydrochloric acid (40 mL) was prepared and cooled in an ice bath, and the solution of diazonium salt was added in portions over a period of about 5 minutes, with stirring, at a rate which avoids the vigorous evolution of nitrogen gas. The mixture was cooled periodically in an ice bath to moderate the nitrogen evolution. When the addition was complete, the mixture was heated to 80° C. After about 20 minutes at that temperature, the evolution of nitrogen ceased. An equal volume of water was added, and the mixture was cooled in an ice bath. After several hours the yellow solid was collected, washed with water, and dried to give 4.8 g of the title compound. $^1$H NMR (DMSO-$d_6$): $\delta$8.72 (1H, d, J=8.1 Hz), 8.63 (1H, d, J=7.5 Hz), 8.61 (1H, s), 8.12 (1H, t, J=7.7 Hz).

EXAMPLE V2

2-tert-Butyloxy-5,6-dichloro-benzo[de]isoquinoline-1,3-dione

The mixture of 3,4-dichloro-1,8-naphthalic anhydride (3.5 g, 13.1 mmol, from Example U2) and O-(t-butyl) hydroxylamine hydrochloride (2.2 g, 17 mmol) in pyridine (30 mL) was warmed to 80° C. with stirring for 2 hours. The solvent was then removed under reduced pressure. The residue was dissolved in dichloromethane, and purified by a column chromatography with dichloromethane as eluent, to give 3.8 g of the title compound. $^1$H NMR (CDCl$_3$): $\delta$8.60 (1H, d, J=8.2 Hz), 8.53 (1H, d, J=7.8 Hz), 8.50 (1H, s), 7.86 (1H, dd, J=8.4, 7.6 Hz), 1.42 (9H), s).

EXAMPLE W2-A,B

4-Bromo-3-methyl-1,8-naphthalic anhydride (A) and 4,6-Dibromo-3-methyl-1,8-naphthalic anhydride (B)

To a suspension of 3-methyl-1,8-naphthalic anhydride (510 mg, 2.4 mmol) in 70% nitric acid (6 mL) was added 0.2 mL of bromine (3.8 mmol) with stirring. The mixture was heated to 70° C. for 2 hours, cooled to room temperature, and an equal volume of water was added to let the product precipitate. The solid was collected, and subjected to column chromatography with dichloromethane as eluent, to give 140 mg of 4-bromo-3-methyl-1,8-naphthalic anhydride (A). $^1$H NMR (CDCl$_3$): $\delta$8.73 (1H, d, J=8.1 Hz), 8.62 (1H, d, J=6.9 Hz), 8.51 (1H, s), 7.90 (1H, dd, J=7.5, 8.1 Hz), 2.76 (3H, s); and 50 mg of 4,6-dibromo-3-methyl-1,8-naphthalic anhydride (B). $^1$H NMR (CDCl$_3$): $\delta$8.87 (1H, d, J=2 Hz), 8.68 (1H, d, J=2 Hz), 8.48 (1H, s), 2.77 (3H, s).

EXAMPLE X2

4,5-Dinitro-3-methoxy-1,8-naphthalic anhydride

This compound was prepared according to the literature procedure of R. W. Middleton and J. Parrick, *J. Het. Chem.*, 1985;22:1567.

EXAMPLE Y2

4,5-Diamino-3-methoxy-1,8-naphthalic anhydride

The 4,5-dinitro-3-methoxy-1,8-naphthalic anhydride (1.5 g, 4.7 mmol, from Example X2) in 30 mL of DMA was reacted with hydrogen at 40 psi with 5% Pd/C as catalyst. After 24 hours, the mixture was filtered and concentrated to give 1.07 g of the title compound.

EXAMPLE Z2

3-Bromo-4-nitro-1,8-naphthalic anhydride

A cooled mixture of concentrated sulfuric acid (5 mL) and concentrated nitric acid (3.50 mL) was added slowly to a solution of 3-bromo-1,8-naphthalic anhydride (2.70 g, 9.74 mmol, from Example N) in concentrated sulfuric acid (10 mL) at 0° C. to 5° C. After complete addition (20 min.), the reaction mixture was stirred at 0° C. to 5° C. for 0.5 hour and poured into ice water (0.5 L). The solid was filtered, washed with water, and dried to give 3.0 g of the title compound.

EXAMPLE A3

3-Bromo-4,5-dinitro-1,8-naphthalic anhydride

A cooled mixture of concentrated sulfuric acid (1.2 mL), concentrated nitric acid (1.65 mL), and fuming nitric acid (0.77 mL) was added slowly to a solution of 3-bromo-4-nitro-1,8-naphthalic anhydride (1.5 g, 4.6 mmol, from Example Z2) in concentrated sulfuric acid (10 mL) at 0° C. to 5° C. After complete addition (5 min.), the reaction mixture was stirred at 0° C. to 5° C. for 0.5 hour, raised to room temperature overnight, and poured into ice water (0.5 L). The solid was filtered, washed with water, and dried to give a gummy solid which was recrystallized from methanol/acetone to give 0.5 g, of the title compound.

EXAMPLE B3-A,B

4-Chloro-3-nitro-1,8-naphthalic anhydride (A) and 5-chloro-3-nitro-1,8-naphthalic anhydride (B)

A cooled mixture of concentrated sulfuric acid (72 mL), concentrated nitric acid (56.0 mL), and fuming nitric acid (16 mL) was added slowly to a solution of 4-chloro-1,8-naphthalic anhydride (25.0 g, 0.107 mol) in concentrated sulfuric acid (72 mL) at 0° C. to 5° C. After complete addition (30 min.), the reaction mixture was stirred at 0° C. to 5° C. for 1 hour and poured into ice water (0.5 L). The solid was filtered, recrystallized two times from concentrated nitric acid, washed with water, acetone and dried to give 15 g of 4-chloro-3-nitro-1,8-naphthalic anhydride (A): mp 233°–234° C., and 6.0 g of the mixture. This was further recrystallized from acetone to give 0.4 g of 5-chloro-3-nitro-1,8-naphthalic anhydride (B).

EXAMPLE C3-A,B 2-tert-Butyloxy-6-chloro-5-nitro-benzo[de]isoquinoline-1,3-dione (A) and 2-tert-Butyloxy-7-chloro-5-nitro-benzo[de]isoquinoline-1,3-dione (B)

A mixture of 4-chloro-3-nitro-1,8-naphthalic anhydride and 5-chloro-3-nitro-1,8-naphthalic anhydride (3.22 g, 11.6 mmol, from Example B3-A,B) in a ratio 1:1, O-tert-butylhydroxylamine hydrochloride (1.74 g, 13.9 mmol) and sodium acetate (1.14 g, 13.9 mmol) in acetic acid (150 mL) was heated at 80° C. for 6 hours. The solvent was evaporated in vacuo to dryness. The residue was suspended in water, extracted with ethyl acetate, and dried (Na$_2$SO$_4$). The solvent was evaporated to dryness and the solid recrystallized from ether to give 4.0 g of 2-tert-butyloxy-6-chloro-5-nitro-benzo[de]isoquinoline-1,3-dione (A) and 2-tert-butyloxy-7-chloro-5-nitro-benzo[de]isoquinoline-1,3-dione (B) as a 1:1 mixture.

EXAMPLE D3-A,B 2-t-Butyloxy-5-nitro-6-(pyrrolidin-1-yl)-benzo[de]isoquinoline-1,3-dione (A) and 2-t-Butyloxy-8-nitro-6-(pyrrolidin-1-yl)-benzo[de]isoquinoline-1,3-dione (B)

Pyrrolidine (0.3 mL) was added to a mixture of 2-tert-butyloxy-6-chloro-5-nitro-benzo[de]isoquinoline-1,3-dione (A) and 2-tert-butyloxy-7-chloro-5-nitro-benzo[de]isoquinoline-1,3-dione (B) (0.30 g, 0.9 mmol, from Example C3-A,B) in ethanol (45 mL). The reaction mixture was stirred at room temperature for 2 days. The solid was filtered and washed with ether to give a 0.27 g of a 1:1 mixture, which was separated by column chromatography using ethyl acetate, then ethyl acetate/ethanol (8:2 v/v) to give 0.11 g of 2-t-butyloxy-5-nitro-6-(pyrrolidin-1-yl)-benzo[de]isoquinoline-1,3-dione (A) and 0.09 g of 2-t-butyloxy-5-nitro-7-(pyrrolidin-1-yl)-benzo[de]isoquinoline-1,3-dione (B).

EXAMPLE E3-A,B

4-Hydroxy-3,6-dinitro-1,8-naphthalic anhydride (A) and 4-chloro-3,6-dinitro-1,8-naphthalic anhydride (B)

A cooled mixture of concentrated sulfuric acid (18 mL) and fuming nitric acid (10 mL) was added slowly to a solution of 4-chloro-3-nitro-1,8-naphthalic anhydride (5.0 g, 0.01 mol, from Example S) in concentrated sulfuric acid (10 mL) at 0° C. to 5° C. After complete addition (30 min.), the reaction mixture was heated at 100° C. for 1.0 hour and poured into ice water (500 mL). The solid was filtered, washed with water, and dried to give 4.5 g of 4-hydroxy-3,6-dinitro-1,8-naphthalic anhydride (A) and of 4-chloro-3,6-dinitro-1,8-naphthalic anhydride (B) as a 1:1 mixture. The mixture was recrystallized from ethanol to give 1.8 g of 4-hydroxy-3,6-dinitro-1,8-naphthalic anhydride (A). The mother liquor was concentrated and further recrystallized from concentrated nitric acid and then acetone to give 1.5 g of 4-chloro-3,6-dinitro-1,8-naphthalic anhydride (B).

EXAMPLE F3

3,6-Dinitro-4-(pyrrolidin-1-yl)-1,8-naphthalic anhydride

A mixture of 4-chloro-3,6-dinitro-1,8-naphthalic anhydride (0.55 g, 1.70 mmol, from Example E3-B) and pyrrolidine (0.2 mL, 2.55 mmol) in ethanol (30 mL) was stirred at room temperature for 15 minutes and heated at 80° C. for 3 hours. The reaction mixture was cooled to room temperature. The solid was filtered and washed with ether to give 0.2 g of the title compound, mp 245°–246° C.

EXAMPLE G3

4-Acetylamino-1,8-naphthalic anhydride

A mixture of 4-amino-1,8-naphthalic anhydride (20.0 g, 0.09 mol, from Example J3) and p-toluenesulfonic acid monohydrate (21.4 g, 0.11 mol) in acetic anhydride (200 mL) was stirred at room temperature for 36 hours. The solid was filtered, and washed with acetone to give 21.0 g of the title compound, mp 289°–290° C.

EXAMPLE H3

4-Acetylamino-3-nitro-1,8-naphthalic anhydride

A mixture of precooled concentrated nitric acid (1.36 mL) in acetic anhydride (4 mL) was added to 4-acetylamino-1,8-naphthalic anhydride (5.0 g, 0.02 mol, from Example G3) at 0° C. to 5° C. for 30 minutes. At room temperature, concentrated sulfuric acid (0.2 mL) was added dropwise. The reaction mixture was stirred at room temperature for 1 hour and poured into ice water. The solid was filtered and washed with water to give 5.0 g of the title compound.

EXAMPLE I3

4-Acetylamino-3-amino-1,8-naphthalic anhydride

A mixture of 4-acetylamino-3-nitro-1,8-naphthalic anhydride (0.5 g, 1.7 mmol, from Example H3) and 5% Pd/C (0.25 g) in DMA was reduced under hydrogen at 40 psi for 5 hours. The mixture was filtered, and the filtrate was poured into ice water. The solid was filtered, washed with water and acetone to give 0.3 g of the title compound, mp >321° C.

EXAMPLE J3

4-Amino-1,8-naphthalic anhydride

Following the procedure from Example C, 8.0 g (33 mmol) of 4-nitro-1,8-naphthalic anhydride was converted to 6.8 g of the title compound.

EXAMPLE K3-A,B 3,4-Dichloro-6-nitro-1,8-naphthalic anhydride (A) and 3,4-dichloro-5-nitro-1,8-naphthalic anhydride (B)

Precooled concentrated nitric acid (1 mL) was added slowly to 3,4-dichloro-1,8-naphthalic anhydride (0.55 g, 1.9 mmol, from Example U2) in concentrated sulfuric acid (8 mL) at 0° C. to 5° C. for 2 hours and poured into ice water. The solid was filtered, washed with water, and dried to give 0.4 g of 3,4-dichloro-6-nitro-1,8-naphthalic anhydride (A) and 3,4-dichloro-5-nitro-1,8-naphthalic anhydride (B) as a 1:1 mixture.

EXAMPLE L3-A,B 2-tert-Butyloxy-5,6-dichloro-8-nitro-benzo[de]isoquinoline-1,3-dione (A) and 2-tert-Butyloxy-5,6-dichloro-7-nitro-benzo[de]isoquinoline-1,3-dione (B)

A 1:1 mixture of 3,4-dichloro-6-nitro-1,8-naphthalic anhydride and 3,4-dichloro-5-nitro-1,8-naphthalic anhydride (0.4 g, 1.28 mmol, from Example K3-A,B), O-tert-butylhydroxylamine hydrochloride (0.24 g, 1.92 mmol) and sodium acetate (0.157 g, 1.92 mmol) in acetic acid (20 mL) was heated at 80° C. for 6 hours and poured into ice water. The solid was filtered and dried to give 0.4 g of a 1:1 mixture of 2-tert-butyloxy-5,6-dichloro-8-nitro-benzo[de]isoquinoline-1,3-dione (A) and 2-tert-butyloxy-5,6-dichloro-7-nitro-benzo[de]isoquinoline-1,3-dione (B), which was separated by column chromatography using ethyl acetate/hexane (8:2 v/v) as eluent to give 0.1 g of 2-tert-butyloxy-5,6-dichloro-8-nitro-benzo[de]isoquinoline-1,3-dione (A).

EXAMPLE M3-A,B 2-tert-Butyloxy-5-chloro-8-nitro-6-(pyrrolidin-1-yl)-benzo[de]isoquinoline-1,3-dione (A) and 2-tert-Butyloxy-5,6-dichloro-7-(pyrrolidin-1-yl)-benzo[de]isoquinoline-1,3-dione (B)

Pyrrolidine (0.7 mL) was added to a 1:1 mixture of 2-tert-butyloxy-5,6-dichloro-8-nitro-benzo[de]isoquinoline- 1,3-dione (A) and 2-tert-butyloxy-5,6-dichloro-7-nitro-benzo[de]isoquinoline-1,3-dione (B) (1.0 g, 0.0026 mol, from Example L3-A,B) in ethanol (45 mL), and the reaction was heated to 80° C. for 30 minutes. The solvent was evaporated to dryness. The crude product was purified and separated by column chromatography using dichloromethane/hexane (1:1) as eluent to give 0.5 g of 2-tert-butyloxy-5-chloro-8-nitro-6-(pyrrolidin-1-yl)-benzo[de]isoquinoline-1,3-dione (A), mp 234°–235° C. and 0.5 g of 2-tert-butyloxy-5,6-dichloro-7-(pyrrolidin-1-yl)-benzo[de]isoquinoline-1,3-dione (B), mp 161°–162° C.

EXAMPLE N3

4-Formyl-3-hydroxy-1,8-naphthalic anhydride (3)

To a suspension of 2.0 g (7.8 mmol) 11H-5,8,10-trioxabenzo[de]anthracene-4,6-dione (from Example K1) in 125 mL dioxane was added 2.0 mL (38.8 mmol) of bromine. The reaction mixture was refluxed for 1.5 hours and poured into 500 mL water. The precipitate was isolated and dried to yield 1.89 g of the title compound.

EXAMPLE O3

3,4-Dihydroxy-1,8-naphthalic anhydride

To a solution of 1.10 g sodium hydroxide (27.5 mmol) in 27 mL water was added 1.33 g (5.5 mmol) of 4-formyl-3-hydroxy-1,8-naphthalic anhydride (from Example N3). After the starting material dissolved, the reaction mixture was cooled to 0° C. to 5° C. and reacted with 1.1 mL (8.7 mmol) of 30% aqueous hydrogen peroxide. It was stirred at 0° C. to 5° C. for 1 hour and quenched with precooled solution of 5.4 mL concentrated sulfuric acid in 20 mL water. The acidified suspension was stirred 18 hours at room temperature. The precipitate was isolated to yield 664 mg of the title compound.

EXAMPLE P3

3,4-Dimethoxy-1,8-naphthalic anhydride

To a solution of 250 mg (1.1 mmol) of 3,4-dihydroxy-1,8-naphthalic anhydride (from Example O3) and 0.74 mL (7.8 mmol) of dimethyl sulfate in 5 mL anhydrous DMF was added 580 mg (10 mmol) of potassium fluoride. The reaction was stirred for 20 hours at room temperature and quenched with 25 mL water. The precipitate was isolated and dried to yield 220 mg of the title compound.

EXAMPLE Q3

3,4-Methylenedioxy-1,8-naphthalic anhydride

To a solution of 365 mg (1.59 mmol) of 3,4-dihydroxy-1,8-naphthalic anhydride (from Example O3) and 0.3 mL (4.47 mmol) of bromochloromethane in 7 mL anhydrous DMF was added 570 mg (2.95 mmol) of cesium carbonate. The reaction was stirred for 24 hours at 80° C. to 90° C. and quenched with 25 mL 5% HCl. The precipitate was isolated, dried, and suspended in 7 mL refluxing acetone. After 4 days at 0° C. to 5° C., the precipitate was isolated and dried to yield 200 mg of the title compound.

EXAMPLE R3

9H,10H-5,8,11-Trioxabenzo[de]anthracene-4,6-dione

To a solution of 310 mg (1.35 mmol) of 3,4-dihydroxy-1,8-naphthalic anhydride (from Example O3) and 1.0 mL (12 mmol) of 1-bromo-2-chlorethane in 10 mL anhydrous DMF was added 440 mg (1.35 mmol) of cesium carbonate. The reaction was stirred for 2 hours at 90° C. to 95° C. and quenched with 25 mL 5% HCl. The precipitate was isolated, dried, and suspended in 10 mL refluxing acetone. After 4 days at 0° C. to 5° C., the precipitate was isolated and dried to yield 130 mg of the title compound.

EXAMPLE S3

4-Hydroxy-1,8-naphthalic anhydride

To a solution of 1.0 g (4.7 mmol) of 4-amino-1,8-naphthalic anhydride in 5 mL concentrated sulfuric acid at 0° C. to 5° C. was added 1.0 g (14.5 mmol) of sodium nitrite, and then 0.5 mL of water. The reaction was stirred for 30 minutes at 0° C. to 5° C., followed by addition of 5 mL (38 mmol) of 48% aqueous fluoroboric acid, with stirring for 30 minutes. The mixture was poured into ice water. The precipitate was isolated, suspended in a solution of 10 mL concentrated sulfuric acid in 50 mL water, refluxed in 3 hours, and again poured onto ice. The precipitate was isolated, washed with water, and dried to yield 620 mg of the title compound.

EXAMPLE T3

8H-5,9,11-Trioxabenzo[de]anthracene-4,6-dione

To a suspension of 620 mg (2.9 mmol) of 4-hydroxy-1,8-naphthalic anhydride (from Example S3) and 1.60 g (53.0 mmol) of paraformaldehyde in 20 mL dioxane was added 5.2 mL of concentrated sulfuric acid. The reaction mixture was refluxed for 1 hour and quenched with 100 mL water. The precipitate was isolated, dried, recrystallized from DMSO, washed with acetone, and dried again to yield 0.50 g of the title compound.

EXAMPLE U3

3-Formylamino-1,8-naphthalic anhydride

A suspension of 2.77 g (13.0 mmol) of 3-amino-1,8-naphthalic anhydride (from Example C) in 20 mL formic acid was refluxed for 40 minutes, cooled to room temperature, and filtered. A solid was washed with water and dried to yield 2.94 g of the title compound.

EXAMPLE V3-A,B

3-Amino-4-nitro-1,8-naphthalic anhydride (A) and 3-amino-4,5-dinitro-naphthalic anhydride (B)

To a solution of 33.67 g (140 mmol) of 3-formylamino-1,8-naphthalic anhydride (from Example U3) in 85 mL concentrated sulfuric acid at 0° C. to 5° C. was added a pre-cooled solution of 11.6 mL (165.3 mmol) of fuming nitric acid in 60 mL concentrated sulfuric acid. The reaction mixture was stirred 1 hour at 45° C. to 55° C., quenched with ice, and the precipitate was isolated, dried, suspended in 50 mL refluxing acetone, and kept at 0° C. to 5° C. for 24 hours. The solid was collected and again was suspended in 35 mL refluxing acetone and kept at 0° C. to 5° C. for 24 hours. The precipitate was isolated and dried to yield 10.64 g of a mixture of the title compounds 3-amino-4-nitro-1,8-naphthalic anhydride (A) and 3-amino-4,5-dinitro-naphthalic anhydride (B) in a 1:1 molar ratio.

EXAMPLE W3-A,B

3-Fluoro-4-hydroxy-1,8-naphthalic anhydride (A) 3-fluoro-4,5-dinitro-1,8-naphthalic anhydride (B)

To 1.4 g (~5 mmol) of a mixture of 3-amino-4-nitro-1,8-naphthalic anhydride (A) and 3-amino-4,5-dinitronaphthalic anhydride (B) (from Example V3-A,B) in 200 mL of pyridine-HF was added 1.4 g (21.7 mmol) of sodium nitrite. The reaction mixture was heated at 140° C. to 150° C. for 3 hours, cooled to room temperature, and quenched with ice. The precipitate was isolated, dried, and chromatographed twice to yield 152 mg of 3-fluoro-4-hydroxy-1,8-naphthalic anhydride (A) and 80 mg of 3-fluoro-4,5-dinitro-1,8-naphthalic anhydride (B).

EXAMPLE X3

3-Fluoro-4-methoxy-1,8-naphthali anhydride

To a solution of 122 mg (0.53 mmol) of 3-fluoro-4-hydroxy-1,8-naphthalic anhydride (from Example W3-A) and 0.15 mL (1.58 mmol) of dimethyl sulfate in 4 mL anhydrous DMF was added 150 mg (2.59 mmol) of potassium fluoride. The reaction mixture was stirred for 20 hours at room temperature and quenched with 25 mL brine. The precipitate was isolated, washed with water, and dried to yield 85 mg of the title compound.

EXAMPLE Y3

2-Benzyloxy-5-fluoro-6-methoxy-benzo[de]isoquinoline-1,3-dione

To a suspension of 85 mg (0.35 mmol) of 3-fluoro-4-methoxy-1,8-naphthalic anhydride (from Example X3) in 10 mL acetic acid was added 80 mg (0.48 mmol) of O-benzylhydroxyalamine hydrochloride and 80 mg (0.98 mmol) of sodium acetate. The reaction mixture was stirred for 2 hours at 100° C. and poured into 20 mL water. The precipitate was isolated, washed with water, and dried to yield 95 mg of the title compound.

EXAMPLE Z3

2-Benzyloxy-5-fluoro-6-(pyrrolidin-1-yl)-benzo[de]isoquinoline-1,3-dione.

A solution of 48 mg (0.14 mmol) of 2-benzyloxy-5-fluoro-6-methoxy-benzo[de]isoquinoline-1,3-dione (from Example Y3) in 1 mL of pyrrolidine was refluxed for 1 hour and poured into 15 mL of brine. The precipitate was isolated and washed with water until washings were colorless. The solid was dried to yield 32 mg of the title compound.

EXAMPLE A4

2-Methoxy-6-nitro-1,8-naphthalic anhydride

Nitric acid (2.5 ml, 28 mmol) was added to a solution of 2-methoxy-1,8-naphthalic anhydride (0.64 g, 2.8 mmol, from Example P1) in 25 mL of acetic anhydride at 0° C. After 30 minutes, a few drops of concentrated sulfuric acid was added and the mixture was stirred at 0° C. for 3 hours. The mixture was filtered, triturated with water, filtered, and dried to give 0.57 g of the title compound.

EXAMPLE B4

6-Amino-2-methoxy-1,8-naphthalic anhydride

Raney nickel (0.5 g) was added to a solution of 2-methoxy-6-nitro-1,8-naphthalic anhydride (0.34 g, 1.2 mmol, from Example A4) in 50 mL of methanol. The suspension was placed under 50 psi of hydrogen and shaken for 30 minutes. The mixture was filtered, and the catalyst was resuspended in DMF and refiltered. The combined filtrates were concentrated to give 0.3 g of the title compound.

EXAMPLE C4

3-Nitro-5,6-dichloronapthene

A suspension of 5,6-dichloroacenaphthene (17.6 g, 78.9 mmol, Ger. Offen. 2721640, C.A. 90:54735) in 400 mL of acetic anhydride was cooled to 10° C. and treated portionwise with cupric nitrate 2.5 $H_2O$ (19.8 g, 85 mmol). The reaction was stirred at 10° C. for 4 hours, then room temperature for 18 hours. The insoluble material was removed by filtration and partitioned between water and dichloromethane. The organic layer was dried, the solvent removed in vacuo, and the residue was triturated with dichloromethane. The solid was removed by filtration, washed with dichloromethane, and dried in vacuo to give 6.4 g of the title compound.

EXAMPLE D4

3-Amino-5,6-dichloroacenaphthene

A solution of 5,6-dichloro-3-nitroacenaphthene (3.7 g, 13.8 mmol, from Example C4) in 250 mL of tetrahydrofuran was treated with 1.0 g of Raney-nickel and shaken in a hydrogen atmosphere at 21° C. and a pressure of 52.8 psi for 14 hours. The catalyst was removed by filtration, and the solvent was removed in vacuo to give 3.3 g of the title compound.

EXAMPLE E4

3-Acetylamino-5,6-dichloroacenaphthene

A suspension of 3-amino-5,6-dichloroacenaphthene (3.3 g 13.8 mmol, from Example D4) in 10 mL of acetic acid was treated with 10 mL of acetic anhydride and heated on a steam bath for 1 hour. The reaction was cooled to 10° C., and the solid was removed by filtration, washed with petroleum ether, and dried in vacuo to give 3.5 g of the title compound.

EXAMPLE F4

2-Acetylamino-4,5-dichloronaphthalic anhydride

A suspension of sodium dichromate dihydrate (7.5 g, 25 mmol) in 50 mL of acetic acid was heated to reflux and treated with acetic anhydride (6.6 g, 65 mmol). The reaction was stirred at reflux and treated portionwise with 3-acetylamino-5,6-dichloroacenapthene (1.4 g, 5.0 mmol, from Example E4). The reaction was refluxed for 5 hours, cooled to room temperature and poured into a mixture of ice and water. The resulting precipitate was removed by filtration, washed with water and dried in vacuo to give 1.2 g of the title compound.

EXAMPLE G4

4-Acetylamino-2-allyloxy-6,7-dichlorobenzo[de]isoquinoline-1,3-dione

A suspension of 2-acetylamino-4,5-dichloronaphthalic anhydride (0.8 g 2.5 mmol, from Example F4), O-allylhydroxylamine hydrochloride hydrate (0.4 g, 3.5 mmol), sodium acetate (0.6 g, 7.0 mmol), and 30 mL of ethanol was stirred at reflux for 3 hours. The solid was removed by filtration, washed with ethanol, and dried to give 0.9 g of the title compound.

EXAMPLE H4

4-Acetylamino-2-allyloxy-7-chloro-6-(pyrrolidin-1-yl)benzo[de]isoquinoline-1,3 dione A near solution of 4-acetylamino-2-allyloxy-6,7-dichlorobenzo[de]isoquinoline-1,3-dione (0.3 g, 0.8 mmol, from Example G4), pyrrolidine (0.16 g, 2.2 mmol), and 15 mL of acetonitrile was heated from room temperature to reflux over 0.5 hour. The solvent was removed in vacuo and the residue partitioned between dichloromethane and water. The organic layer was washed with water, dried, and evaporated in vacuo to give 0.26 g of the title compound.

EXAMPLE I4

2-Allyloxy-4,6,7-trichlorobenzo[de]isoquinoline-1,3-dione

A solution of 2,4,5-trichloro-1,8-naphthalic anhydride (0.9 g, 3.0 mmol, Ger. Offen. 2653346, C.A. 89:108824) O-allylhydroxylamine hydrochloride hydrate (0.36 g, 3.3 mmol), sodium acetate (0.4 g, 5.0 mmol), and 30 mL of ethanol was heated at reflux for 4 hours. The reaction was cooled to room temperature, diluted with 50 mL of water, cooled to 5° C., and the precipitate removed by filtration. After washing with water, the solid was dried in vacuo to give 0.92 g of the title compound.

EXAMPLE J4

2-Allyloxy-4,7-dichloro-6-(pyrrolidin-1-yl)benzo[de]isoquinoline-1,3-dione

A suspension of 2-allyloxy-4,6,7-trichlorobenzo[de]isoquinoline-1,3-dione (0.5 g, 1.5 mmol, from Example I4), pyrrolidine (0.14 g, 2.0 mmol), triethylamine (0.3 g, 3.0 mmol), and 25 mL of acetonitrile was stirred at room temperature for 4 hours. The reaction was diluted with 100 mL of water, and the precipitate was removed by filtration, washed with water, and dried in vacuo to give 0.53 g of the title compound.

EXAMPLE K4

(S)-[1-(2-Allyloxy-4,7-dichloro-1,3-dioxo-2,3-dihydro-1H-benzo[de]isoquinolin 6-yl)pyrrolidine-3-yl]carbamic acid tert-butyl ester A suspension of 2-allyloxy-4,6,7-trichlorobenzo[de]isoquinoline-1,3-dione (0.44 g, 1.2 mmol, from Example I4), (S)-pyrrolidin-3-ylcarbamic acid tert-butyl ester (0.3 g, 1.5 mmol), triethylamine (0.2 g, 2.0 mmol), and 20 mL of acetonitrile was stirred at room temperature for 6 hours. The solvent was removed in vacuo and the residue partitioned between water and dichloromethane. The organic layer was dried and evaporated in vacuo. The residue was chromatographed on silica gel (ICN 230–400 mesh) eluting with dichloromethane/ethyl acetate (80:20) to give 0.35 g of the title compound, mp 123–125° C.

The following examples are illustrative of compounds useful in the synthesis of the final compounds of the invention.

EXAMPLE 1

2-Hydroxy-5-nitro-benzo[de]isoquinoline-1,3-dione

Hydroxylamine hydrochloride (0.9 g, 13.0 mmol) was added to a suspension of 3-nitro-1,8-naphthalic anhydride (2.0 g, 8.2 mmol) in pyridine (30 mL). The mixture was refluxed for 3 hours and concentrated in vacuo to give a brown solid. The solid was suspended in water, stirred, filtered, and dried to give 2.1 g of the title compound, mp 277–279° C.

EXAMPLE 2

2-Hydroxy-6-nitro-benzo[de]isoquinoline-1,3-dione

4-Nitro-1,8-naphthalic anhydride (2.61 g, 10.7 mmol) and hydroxylamine hydrochloride (1.5 g, 21.4 mmol) were reacted in pyridine (50 mL) following the procedure of Example 1. The crude product was recrystallized from ethanol to give 2.0 g of the title compound, mp 255–260° C.;

$^1$H NMR (DMSO-$d_6$): δ 11.0 (1H, s), 8.8–8.5 (4H, m), 8.1 (1H, dd, J=7.7, 7.5).

EXAMPLE 3

2,5-Dihydroxy-benzo[de]isoquinoline-1,3-dione

3-Hydroxy-1,8-naphthalic anhydride (1.4 g, 6.7 mmol) and hydroxylamine hydrochloride (0.9 g, 12.9 mmol) were reacted in pyridine (30 mL) following the procedure of Example 1 to give 2.0 g of the title compound, mp 285≧288/ C.;

$^1$H NMR (DMSO-$d_6$): δ 10.7 (1H, s), 10.6 (1H, s), 8.4 (2H, m), 8.0 (1H, d, J=2.4), 7.8 (1H, dd, J=7.4, 7.3), 8.7 (1H, d, J=2.4).

EXAMPLE 4

6-Bromo-2-hydroxy-benzo[de]isoquinoline-1,3-dione

4-Bromo-1,8-naphthalic anhydride (1.6 g, 5.8 mmol) and hydroxylamine hydrochloride (0.8 g, 11.5 mmol) were reacted in pyridine (30 mL) following the procedure of Example 1 to give 1.4 g of the title compound, mp 248–251° C.;

$^1$H NMR (DMSO-$d_6$): δ 10.9 (1H, s), 8.6 (2H, dd merge to t), 8.4 (1H, dd, J=7.2, 1.2), 8.2 (1H, dd, J=7.1, 1.2), 8.0 (1H, dd, J=7.2, 7.1).

EXAMPLE 5

Potassium 2-Hydroxy-1,3-dioxo-2,3-dihydro-1H-benzo[de]isoquinoline-6-sulfonate

4-Sulfo-1,8-naphthalic anhydride potassium salt (2.0 g, 6.2 mmol) and hydroxylamine hydrochloride (0.9 g, 12.4 mmol) were reacted in pyridine (50 mL) following the procedure of Example 1. The solids formed were filtered, washed with ethanol, and dried to give 2.1 g of the title compound, mp>380° C.;

$^1$H NMR (DMSO-$d_6$): δ 10.8 (1H, br s), 9.3 (1H, dd, J=7.1, 1.0), 8.5 (2H, m), 8.2 (1H, d, J=7.6), 7.9 (1H, dd, J=7.4, 7.1).

EXAMPLE 6

6-Chloro-2-hydroxy-benzo[de]isoquinoline-1,3-dione

4-Chloro-1,8-naphthalic anhydride (1.4 g, 6.0 mmol) and hydroxylamine hydrochloride (0.8 g, 11.5 mmol) were reacted in pyridine (50 mL) following the procedure of Example 1 to give 1.2 g of the title compound, mp 234–236° C.;

$^1$H NMR (DMSO-$d_6$): δ 10.9 (1H, s), 8.7 (2H, m), 8.6 (1H, d, J=7.5), 8.1–7.9 (2H, m).

EXAMPLE 7

6-Amino-2-hydroxy-benzo[de]isoquinoline-1,3-dione

4-Amino-1,8-naphthalic anhydride (0.2 g, 0.9 mmol) and hydroxylamine hydrochloride (0.1 g, 1.4 mmol) were reacted in pyridine (20 mL) following the procedure of Example 1 to give 0.2 g of the title compound, mp>360° C.;

¹H NMR (DMSO-d₆): δ 10.4. (1H, d, J=8.2), 8.5 (1H, d, J=7.0), 8.2 (1H, d, J=8.4), 7.7 (1H, dd, J=8.2, 7.0), 7.5 (2H, br s), 6.8 (1H, d, J=8.4).

EXAMPLE 8

5-Amino-2-hydroxy-benzo[de]isoquinoline-1,3-dione

A solution of compound 5-amino-2-tert-butyldimethylsilyoxy-1,3-dioxo-2,3-dihydro-1H-benzo[de] isoquinoline (0.8 g, 2.3 mmol, from Example B) in 2% HCl in ethanol (50 mL) was stirred at room temperature for 1 hour. The solid which formed was filtered and dried, to give 0.4 g of the title compound, mp 288–294° C. (dec).

EXAMPLE 8B

5-Amino-2-hydroxy-benzo[de]isoquinoline-1,3-dione

3-Amino-1,8-naphthalic anhydride (0.12 g, 0.6 mmol, from Example C) and hydroxylamine hydrochloride (0.1 g, 14.4 mmol) were reacted in pyridine (5 mL) following the procedure of Example 1, to give 0.1 g of the title compound, mp 292–296° C.;

¹H NMR (DMSO-d₆): δ 10.6 (1H, s), 8.1 (3H, dd, J=7.8, 6.5), 7.9 (1H, d, J=2.2), 7.6 (1H, dd, J=7.9, 7.5), 6.0 (2H, s).

EXAMPLE 9

5-Acetamido-N-2-hydroxy-benzo[de]isoquinoline-1,3-dione

Sodium hydroxide (0.03 g, 0.8 mmol) was added to a suspension of 5-acetamido-2-acetoxy-benzo[de] isoquinoline-1,3-dione (0.2 g, 0.6 mmol, from Example E) in methanol (15 mL). The mixture was stirred at room temperature for 1 hour, and the resulting solution was acidified with concentrated HCl to pH 4. The precipitate formed was filtered, washed with water, and dried to give 0.1 g of the title compound, mp 328–333° C.;

¹H NMR (DMSO-d₆): δ 10.8 (1H, s), 10.6 (1H, s), 8.8 (1H, d, J=1.9), 8.6 (1H, d, J=1.9), 8.2 (2H, d, J=7.5), 7.8 (1H, dd, J=7.5, 7.5), 2.2 (3H, s).

EXAMPLE 10

5-Trifluoromethanesulfonyloxy-2-hydroxy-benzo[de]isoquinoline-1,3-dione

A solution of hydroxylamine hydrochloride (0.1 g, 1.6 mmol) in water (5 mL) was added to a solution of 3-trifluoromethanesulfonyloxy-1,8-naphthalic anhydride (0.4 g, 1.1 mmol, from Example F) in ethanol (50 mL), and the resulting mixture was refluxed for 8 hours. The solid formed was filtered, washed with water, and dried to give 0.2 g of the title compound, mp 167–169° C.;

¹H NMR (DMSO-d₆): δ 10.9 (1H, s), 8.8 (1H, d, J=2.5), 8.6 (2H, m), 8.5 (1H, d, J=2.5), 8.0 (1H, dd, J=7.1, 7.0).

EXAMPLE 11

5-Fluoro-2-hydroxy-benzo[de]isoquinoline-1,3-dione

3-Fluoro-1,8-naphthalic anhydride (0.15 g, 0.7 mmol, from Example H) and hydroxylamine hydrochloride (0.1 g, 1.5 mmol) were reacted in pyridine (5 mL) following the procedure of Example 1 to give 0.1 g of the title compound, mp 244–247° C.;

¹H NMR (DMSO-d₆): δ 10.4 (1H, br s), 8.6–8.3 (4H, m), 8.0 (1H, dd, J=7.9, 7.6).

EXAMPLE 12

6-Fluoro-2-hydroxy-benzo[de]isoquinoline-1,3-dione

4-Fluoro-1,8-naphthalic anhydride (0.15 g, 0.7 mmol, from Example 1) and hydroxylamine hydrochloride (0.1 g, 1.5 mmol) were reacted in pyridine (5 mL) following the procedure of Example 1 to give 0.12 g of the title compound, mp 257–261° C.;

¹H NMR (DMSO-d₆): δ 10.8 (1H, s), 8.7–8.5 (3H, m), 8.0 (1H, dd, J=8.3, 7.5), 7.7 (1H, dd, J=10.3, 8.1).

EXAMPLE 13

2-Hydroxy-5-methoxy-benzo[de]isoquinoline-1,3-dione

3-Methoxy-1,8-naphthali anhydride (0.82 g, 3.6 mmol, from Example J) and hydroxylamine hydrochloride (0.38 g, 5.5 mmol) were reacted in pyridine (50 mL) following the procedure of Example 1 to give 0.5 g of the title compound (Ref. J. C. S. (C), 1966:523–527), mp 236–239° C.;

¹H NMR (DMSO-d₆): δ 10.8 (1H, s), 8.4 (2H, d, J=8.0), 8.0 (1H, d, J=2.5), 7.9 (1H, d, J=2.5), 7.8 (1H, dd, J=7.8, 7.7), 4.0 (3H, s).

EXAMPLE 14

5-Ethoxy-2-hydroxy-benzo[de]isoquinoline-1,3-dione

3-Ethoxy-1,8-naphthalic anhydride (0.15 g, 0.6 mmol, from Example K) and hydroxylamine hydrochloride (0.07 g, 1.0 mmol) were reacted in pyridine (10 mL) following the procedure of Example 1 to give 0.05 g of the title compound, mp 224–227° C.;

¹H NMR (DMSO-d₆): δ 10.7 (1H, s), 8.3 (2H, d, J=7.7), 8.0 (1H, d, J=2.5), 7.9 (1H, d, J=2.5), 7.8 (1H, dd, J=8.1, 7.5), 4.3 (2H, q, J=7.0), 1.5 (3H, t, J=7.0).

EXAMPLE 15

2-Hydroxy-6-(4-methyl-piperazin-1-yl)-benzo[de]isoquinoline-1,3-dione 4-(4-Methylpiperazinyl)-1,8-naphthalic anhydride (0.2 g, 0.7 mmol, from Example L) and hydroxylamine hydrochloride (0.08 g, 1.2 mmol) were reacted in pyridine (5 mL) following the procedure of Example 1 to give 0.12 g of the title compound, mp 326–329° C.;

¹H NMR (DMSO-d₆): δ11.0 (1H, br s), 10.7 (1H, s), 8.6–8.4 (3H, m), 7.9 (1H, dd, J=8.2, 7.4), 7.5 (1H, d, J=8.2), 3.8–3.2 (8H, m), 2.9 (3H, s).

EXAMPLE 16

2-Hydroxy-6-methylthio-benzo[de]isoquinoline-1,3-dione

Sodium thiomethoxide (0.9 g, 12.0 mmol) was added to a solution of 6-bromo-2-hydroxy-benzo[de]isoquinoline-1,3-dione (1.2 g, 4.0 mmol, from Example 4) in ethanol (200 mL). The mixture was refluxed for 48 hours and concentrated. The solid residue was dissolved in water and acidified with concentrated HCl to pH 4. The resulting precipitate was filtered, washed with water, and dried to give 0.8 g of the title compound, mp 301–206° C.

¹H NMR (DMSO-d₆): δ 10.7 (1H, s), 8.6 (1H, d, J=7.1), 8.5 (1H, d, J=8.6), 8.4 (1H, d, J=8.0), 7.8 (1H, dd, J=8.6, 7.1), 7.6 (1H, d, J=8.0), 2.7 (3H, s).

EXAMPLE 17

2-Hydroxy-6-methoxy-benzo[de]isoquinoline-1,3-dione

2-Benzyloxy-6-bromo-benzo[de]isoquinoline-1,3-dione (3.2 g, 8.4 mmol, from Example M) was added to a solution of sodium hydride (0.5 g, 12.5 mmol) in methanol (100 mL). The mixture was refluxed for 8 hours and concentrated in vacuo. The solid residue was dissolved in water and acidified with concentrated HCl to pH 4. The resulting precipitate was filtered, washed with water, and dried to give 0.8 g of 2-benzyloxy-6-methoxy-benzo[de]-isoquinoline-1,3-dione. The hydrogenation of 2-benzyloxy-6-methoxy-benzo[de] isoquinoline-1,3-dione (0.6 g) in the presence of Pd/C (10%) in DMA (20 mL) afforded 0.2 g of the title compound, mp 267–269° C.;

¹H NMR (DMSO-d₆): δ 10.6 (1H, s), 8.7–8.5 (3H, m), 7.9 (1H, dd, J=8.6, 7.2), 7.4 (1H, d, J=7.5), 4.2 (3H, s).

EXAMPLE 18

2-Hydroxy-6-(pyrrolidin-1-yl)-benzo[de]isoquinoline-1,3-dione

Pyrrolidine (3 mL) was added to 2-benzyloxy-6-bromo-benzo[de]isoquinoline-1,3-dione (0.8 g, 2.1 mmol, from Example M) in the presence of DBU (0.05 mL). The mixture was refluxed for 2 hours and poured into water (50 mL). The precipitate formed was filtered and dried to give 0.8 g of 2-benzyloxy-6-(pyrrolidin-1-yl)-benzo[de]isoquinoline-1,3-dione. The hydrogenation of 2-benzyloxy-6-(pyrrolidin-1-yl)-benzo[de]isoquinoline-1,3-dione (0.4 g, 1.1 mmol) in the presence of 10% Pd/C (0.2 g) in DMA (30 mL) gave 0.27 g of the title compound, mp 268–270° C.;

¹H NMR (DMSO-d₆): δ 10.7 (1H, s), 8.7 (1H, d, J=8.6), 8.4 (1H, d, J=7.1), 8.2 (1H, d, J=8,7), 7.6 (1H, dd, J=8.2, 7.8), 6.9 (1H, d, J=8.8), 3.8 (4H, br s), 2.0 (4H, br s).

EXAMPLE 19

2-Hydroxy-6-(morpholin-4-yl)-benzo[de]isoquinoline-1,3-dione

2-Benzyloxy-6-bromo-benzo[de]isoquinoline-1,3-dione (0.8 g, 2.1 mmol, from Example M) was reacted in morpholine (3.0 mL) in the presence of DBU (0.05 mL) following the procedure of Example 18 to give 0.6 g of 2-benzyloxy-6-(morpholin-4-yl)-benzo[de]isoquinoline-1,3-dione. Hydrogenation of 2-benzyloxy-6-(morpholin-4-yl)-benzo[de]isoquinoline-1,3-dione (0.4 g, 0.9 mmol) in the presence of 10% Pd/C (0.2 g) in DMA (30 mL) afforded 0.2 g of the title compound, mp 235–237° C.; ¹H NMR (DMSO-d₆): δ 10.6 (1H, s), 8.5–8.4 (3H, m), 7.8 (1H, t, J=7.9), 7.4 (1H, d, J=8.1), 3.9 (4H, m), 3.2 (4H, m).

EXAMPLE 20

2-Hydroxy-6-(piperidin-1-yl)-benzo[de]isoquinoline-1,3-dione

2-Benzyloxy-6-bromo-benzo[de]isoquinoline-1,3-dione (0.8 g, 2.1 mmol, from Example M) was reacted in piperidine (3.0 mL) in the presence of DBU (0.05 mL) following the procedure of Example 18 to give 0.8 g of 2-benzyloxy-6-(piperidin-1-yl)-benzo[de]isoquinoline-1,3-dione. Hydrogenation of 2-benzyloxy-6-(piperidin-1-yl)-benzo[de] isoquinoline-1,3-dione (0.4 g, 1.0 mmol) in the presence of 10% Pd/C (0.2 g) in DMA (30 mL) afforded 0.28 g of the title compound, mp 222–224° C.;

¹H NMR (DMSO-d₆): δ 10.6 (1H, s), 8.5–8.4 (3H, m), 7.8 (1H, dd, J=7.9, 7.8), 7.3 (1H, d, J=8.1), 3.2 (4H, br s), 1.8 (4H, br s), 1.7 (2H, br s).

EXAMPLE 21

2-Hydroxy-5-methyl-benzo[de]isoquinoline-1,3-dione

The hydrogenation of 2-benzyloxy-5-methyl-benzo[de] isoquinoline-1,3-dione (0.4 g, 1.3 mmol, from Example P) was performed in the presence of 10% Pd/C (0.1 g) in DMA (20 mL). Purification of crude product by column chromatography (silica gel using 10% methanol in dichloromethane) gave 0.1 g of the title compound, mp 251–253° C.;

¹H NMR (DMSO-d₆): δ 10.7 (1H, s), 8.5–8.4 (3H, m), 8.3 (1H, s), 7.8 (1H, dd, J=7.9, 7.5), 2.6 (3H, s).

EXAMPLE 22

5-(2-Dimethylamino-ethoxy)-2-hydroxy-benzo[de]isoquinoline-1,3-dione

2-Chloro-N,N-dimethylethylamine hydrochloride (0.5 g, 3.3 mmol), potassium iodide (0.4 g, 2.4 mmol), and potassium carbonate (1.4 g, 10.1 mmol) were added to a suspension of 2-benzyloxy-5-hydroxy-benzo[de]isoquinoline-1,3-dione (0.8 g, 2.5 mmol) in acetone (100 mL). The mixture was refluxed for 8 hours and concentrated in vacuo. The residue was dissolved in water and extracted with 30% methanol in chloroform. The organic layer was dried (Na₂SO₄), filtered, and concentrated to give 0.3 g of 2-benzyloxy-5-(2-dimethylamino-ethoxy)-benzo[de]isoquinoline-1,3-dione. The hydrogenation of 2-benzyloxy-5-(2-dimethylamino-ethoxy)-benzo[de]isoquinoline-1,3-dione (0.2 g) in the presence of 10% Pd/C (0.2 g) in DMA (20 mL) afforded 0.04 g of the title compound, mp 225–229° C.;

¹H NMR (DMSO-d₆): δ 10.9–10.5 (1H, br s), 8.4–8.3 (2H, br d), 8.1–7.9 (2H, br d), 7.8 (1H, dd, J=7.9, 7.5), 4.3 (2H, t, J=5.9), 2.8 (2H, t, J=5.9), 2.2 (6H, s).

EXAMPLE 23

2-Hydroxy-5-(2-acetoxy-ethoxy)-benzo[de]isoquinoline-1,3-dione

2-Benzyloxy-5-hydroxy-benzo[de]isoquinoline-1,3-dione (1.0 g, 3.1 mmol), and 2-bromoethyl acetate (1.5 g, 9.0 mmol) were reacted in acetone (50 mL) in presence of potassium carbonate (0.7 g, 5.1 mmol) following the procedure of Example 22 to give 1.2 g of 2-benzyloxy-5-(2-acetoxy-ethoxy)-benzo[de]isoquinoline-1,3-dione. The hydrogenation of 2-benzyloxy-5-(2-acetoxy-ethoxy)-benzo [de]isoquinoline-1,3-dione (1.2 g) in the presence of 10% Pd/C (0.8 g) in ethyl acetate afforded 0.5 g of the title compound, mp 232–235° C.;

¹H NMR (DMSO-d₆): δ 10.8 (1H, s), 8.4–8.3 (2H, m), 8.0 (1H, d, J=2.4), 7.9 (1H, d, J=2.5), 7.8 (1H, dd, J=8.0, 7.6), 4.4 (4H, s), 2.1 (3H, s).

EXAMPLE 24

2-Hydroxy-5-(2-hydroxy-ethoxy)-benzo[de]isoquinoline-1,3-dione

A mixture of potassium carbonate (0.4 g, 2.9 mmol) and 2-hydroxy-5-(2-acetoxy-ethoxy)-benzo[de]isoquinoline-1, 3-dione (0.3 g, 1.0 mmol, from Example 23) in methanol (20 mL) was stirred for 2 hours. The mixture was acidified with 1N HCl to pH 4. The precipitate formed was filtered, washed with water, and dried to give 0.2 g of the title compound, mp 242–244° C.;

$^1$H NMR (DMSO-d$_6$): δ 10.7 (1H, s), 8.3 (2H, d, J=7.5), 8.0 (1H, d, J=2.5), 7.9 (1H, d, J=2.5), 7.8 (1H, dd, J=8.0, 7.6), 5.0 (1H, t, J=5.5), 4.2 (2H, t, J=4.8), 3.8 (2H, dt, J=5.5, 4.8).

EXAMPLE 25

2-Hydroxy-5-(2-carboxy-ethoxy)-benzo[de]isoquinoline-1,3-dione

2-Benzyloxy-5-hydroxy-benzo[de]isoquinoline-1,3-dione (1.1 g, 3.5 mmol) and 2-bromopropionic acid (1.2 g, 7.8 mmol) were reacted in acetone (300 mL) in presence of potassium carbonate (2.3 g, 5.1 mmol) and potassium iodide (0.1 g, 0.6 mmol), following the procedure of Example 22 to give 1.1 g of 2-benzyloxy-5-(2-carboxy-ethoxy)-benzo[de]isoquinoline-1,3-dione. The hydrogenation of 2-benzyloxy-5-(2-carboxy-ethoxy)-benzo[de]isoquinoline-1,3-dione (1.1 g) in the presence of 10% Pd/C (0.5 g) in DMA (20 mL) afforded 0.3 g of the title compound, mp 236–239° C.;

$^1$H NMR (DMSO-d$_6$): δ 12.5 (1H, br s), 10.6 (1H, br s), 8.3 (2H, d, J=7.5), 8.0 (2H, m), 7.8 (1H, dd, J=7.8, 7.8), 4.4 (2H, t, J=6.0), 2.8 (2H, t, J=6.0).

EXAMPLE 26

6-Amino-5-bromo-2-hydroxy-benzo[de]isoquinoline-1,3-dione

4-Amino-3-bromo-1,8-naphthalic anhydride (0.11 g, 0.4 mmol, from Example Q) and hydroxylamine hydrochloride (0.1 g, 1.4 mmol) were reacted in pyridine (10 mL) following the procedure of Example 1 to give 0.1 g of the title compound, mp 318–324° C.;

$^1$H NMR (DMSO-d$_6$): δ 10.5 (1H, s), 8.8 (1H, d, J=8.4 ), 8.5 (1H, d, J=7.4), 8.4 (1H, s), 7.8 (1H, dd, J=8.4, 7.4), 7.5 (2H, br s).

EXAMPLE 27

6-Amino-5-chloro-2-hydroxy-benzo[de]isoquinoline-1,3-dione

4-Amino-3-chloro-1,8-naphthalic anhydride (0.1 g, 0.4 mmol, from Example R) and hydroxylamine hydrochloride (0.04 g, 0.5 mmol) were reacted in pyridine (10 mL) following the procedure of Example 1 to give 0.08 g of the title compound, mp 354–359° C.;

$^1$H NMR (DMSO-d$_6$) δ: 10.5 (1H, s), 8.8 (1H, d, J=8.3), 8.5 (1H, d, J=6.7), 8.2 (1H, s), 7.8 (1H, dd, J=8.3, 6.7), 7.6 (2H, br s).

EXAMPLE 28

5-Amino-6-chloro-2-hydroxy-benzo[de]isoquinoline-1,3-dione

3-Amino-4-chloro-1,8-naphthalic anhydride (0.2 g, 0.8 mmol, from Example T) and hydroxylamine hydrochloride (0.1 g, 1.4 mmol) were reacted in pyridine (10 mL) following the procedure of Example 1 to give 0.2 g of the title compound, mp 271–275° C.;

$^1$H NMR (DMSO-d$_6$): δ 10.7 (1H, br s), 8.4–8.1 (3H, m), 7.8 (1H, dd, J=8.4, 7.4), 6.4 (2H, br s).

EXAMPLE 29

2,5-Dihydroxy-6-nitro-benzo[de]isoquinoline-1,3-dione

A solution of hydroxylamine hydrochloride (0.1 g, 1.4 mmol) in water (5 mL) was added to a solution of 3-hydroxy-4-nitro-1,8-naphthalic anhydride (0.3 g, 1,1 mmol, from Example U) in ethanol (20 mL). The mixture was refluxed for 8 hours and concentrated in vacuo. The solid residue was washed with water and dried to give 0.2 g of the title compound, mp 267–270° C.;

$^1$H NMR (DMSO-d$_6$): δ 12.3 (1H, br s), 10.9 (1H, br s), 8.4 (1H, dd, J=6.9, 1.3), 8.2 (1H, s), 8.1–7.9 (2H, m).

EXAMPLE 30

6-Amino-2-hydroxy-5-methoxy-benzo[de]isoquinoline-1,3-dione

Hydrogenation of 2-benzyloxy-5-methoxy-6-nitro-benzo[de]isoquinoline-1,3-dione (0.2 g, from Example W) in the presence of 10% Pd/C (0.2 g) in DMA (20 mL) afforded 0.07 g of the title compound, mp 269–273° C.;

$^1$H NMR (DMSO-d$_6$): δ 10.4 (1H, s), 8.7 (1H, d, J=8.4), 8.4 (1H, d, J=7.1), 8.0 (1H, s), 7.6 (1H, dd, J=8.4, 7.1), 7.2 (2H, br s), 4.0 (3H, s).

EXAMPLE 31

5-Bromo-2-hydroxy-6-methoxy-benzo[de]isoquinoline-1,3-dione

A mixture of 2-hydroxy-6-methoxy-benzo[de]isoquinoline-1,3-dione (0.12 g, 0.5 mmol, from Example 17) and N-bromosuccinimide (0.13 g, 0.7 mmol) in acetic acid (20 mL) was sonicated at 60° C. for 24 hours. The mixture was transferred to a preheated oil bath at 100° C. with vigorous stirring for another 24 hours. The precipitate was filtered, washed with water, dried, and recrystallized from methanol to give 0.05 g of the title compound, mp 223–227° C.;

$^1$H NMR (DMSO-d$_6$): δ 10.8 (1H, br s), 8.6–8.5 (3H, m), 8.0 (1H, dd, J=8.3, 7.2), 4.1 (3H, s).

EXAMPLE 32

6-Bromo-2-hydroxy-5-methoxy-benzo[de]isoquinoline-1,3-dione

2-Hydroxy-5-methoxy-benzo[de]isoquinoline-1,3-dione (0.32 g, 1.3 mmol, from Example 13) and N-bromosuccinimide (0.33 g, 1.8 mmol) were reacted in acetic acid (10 mL) following the procedure of Example 31 to give 0.11 g of the title compound, mp 250–253° C.;

$^1$H NMR (DMSO-d$_6$): δ 10.9 (1H, s), 8.5 (1H, d, J=8.2), 8.4 (1H, d, J=6.9), 8.3 (1H, s), 8.0 (1H, dd, J=8.2, 6.9), 4.1 (3H, s).

EXAMPLE 33

2-Hydroxy-5-methoxy-6-(4-methyl-piperazin-1-yl)-benzo[de]isoquinoline-1,3-dione, Hydrochloride 2-Benzyloxy-6-bromo-5-methoxy-benzo[de]isoquinoline-1,3-dione (0.5 g, from Example Z) was reacted with N-methylpiperazine (30 mL) following the procedure of Example 18 to give 0.5 g of 2-benzyloxy-5-methoxy-6-(4-methyl-piperazin-1-yl)-benzo[de]isoquinoline-1,3-dione. Hydrogenation of 2-benzyloxy-5-methoxy-5-(4-methylpiperazin-1-yl)-benzo[de]isoquinoline-1,3-dione (0.3 g) at 40 psi in the presence of Pd/C (10%) in DMA (20 mL) afforded 0.2 g of the title compound as the free base. A solution of acetyl chloride (0.03 mL) in ethanol (1mL) was added to a solution of 2-hydroxy-5-methoxy-6-(4-methyl-piperazin-1-yl)-benzo[de]isoquinoline-1,3-dione (0.12 g, 0.4 mmol) in ethanol (5 mL). The solution was stirred for 30 minutes, and the precipitate was filtered, washed with ether, and dried to give 0.13 g of the title compound as the HCl salt, mp 296–300° C.;

$^1$H NMR (DMSO-d$_6$): δ 10.8 (1H, br s), 10.5 (1H, br s), 8.7 (1H, d, J=8.4), 8.4 (1H, d, J=6.8), 8.2 (1H, s), 7.9 (1H, dd, J=8.4, 6.8), 4.1 (3H, s), 3.6–3.0 (8H, br m), 2.9 (3H, br s).

EXAMPLE 34

2-Hydroxy-5-methoxy-6-(pyrrolidin-1-yl)-benzo[de]isoquinoline-1,3-dione

2-Benzyloxy-6-bromo-5-methoxy-benzo[de]isoquinoline-1,3-dione (0.5 g, 1.2 mmol, from Example Z) was reacted with pyrrolidine (3.0 mL) in the presence of DBU (0.05 mL) following the procedure of Example 18 to give 0.44 g of 2-benzyloxy-5-methoxy-6-(pyrrolidin-1-yl)-benzo[de]isoquinoline-1,3-dione. Hydrogenation of 2-benzyloxy-5-methoxy-6-(pyrrolidin-1-yl)-benzo[de]isoquinoline-1,3-dione (0.44 g, 1.08 mmol) in the presence of 10% Pd/C (0.2 g) in DMA (30 mL) afforded 0.2 g of the title compound, mp 177–179° C.;

$^1$H NMR (DMSO-d$_6$): δ 10.7 (1H, s), 8.5 (1H, d, J=7.7), 8.3 (1H, d, J=7.3), 8.2 (1H, s), 7.7 (1H, dd, J=8.4, 7.7), 4.0 (3H, s), 3.5–3.4 (4H, m), 2.0–1.9 (4H, m).

EXAMPLE 35

2-Hydroxy-5-methoxy-6-(piperidin-1-yl)-benzo[de]isoquinoline-1,3-dione

2-Benzyloxy-5-methoxy-6-bromo-benzo[de]isoquinoline-1,3-dione (0.5 g, 1.2 mmol, from Example Z) was reacted in piperidine (3 mL) in the presence of DBU (0.05 mL) following the procedure of Example 18 to give 0.3 g of 2-benzyloxy-5-methoxy-6-(piperidin-1-yl)-benzo[de]isoquinoline-1,3-dione. The hydrogenation of 2-benzyloxy-5-methoxy-6-(piperidin-1-yl)-benzo[de]isoquinoline-1,3-dione (0.3 g, 0.7 mmol) was performed as described in Example 18 to give 0.17 g of the title compound, mp 204–205° C.;

$^1$H NMR (DMSO-d$_6$): δ 10.7 (1H, s), 8.6 (1H, d, J=7.9), 8.4 (1H, d, J=6.6), 8.2 (1H, s), 7.8 (1H, dd, J=8.3, 7.4), 4.0 (3H, s), 3.2 (4H, br s), 1.7 (6H, br s).

EXAMPLE 36

2-Hydroxy-5-methoxy-6-(morpholin-4-yl)-benzo[de]isoquinoline-1,3-dione

2-Benzyloxy-5-methoxy-6-bromo-benzo[de]isoquinoline-1,3-dione (0.5 g, 1.2 mmol, from Example Z) was reacted with morpholine (3 mL) in the presence of DBU (0.05 mL) following the procedure of Example 18 to give 0.25 g of 2-benzyloxy-5-methoxy-6-(morpholin-4-yl)-benzo[de]isoquinoline-1,3-dione. Hydrogenation of 2-benzyloxy-5-methoxy-6-(morpholin-4-yl)-benzo[de]isoquinoline-1,3-dione (0.25 g, 0.6 mmol) was performed as described in Example 18, to give 0.17 g of the title compound, mp 329–241° C. (dec.);

$^1$H NMR (DMSO-d$_6$): δ 10.7 (1H, s), 8.7 (1H, d, J=7.9), 8.4 (1H, J=6.5), 8.3 (1H, s), 7.8 ( 1H, dd, J=7.4, 7.4), 4.0 (3H, s), 3.8 (4H, m), 3.2 (4H, br s).

EXAMPLE 37

6-(2-Chloroacetamido)-methyl-2,5-dihydroxy-benzo[de]isoquinoline-1,3-dione

A solution of hydroxylamine hydrochloride (0.1 g, 1.4 mmol) in water (10 mL) was added to a solution of 4-(2-chloroacetamido)-methyl-3-hydroxy-1,8-naphthalic anhydride (0.2 g, 0.6 mmol, from Example A1) in ethanol (20 mL). After addition, the solution was refluxed for 6 hours, and the precipitate formed was filtered and dried to give 0.1 g of the title compound, mp 243–245° C.;

$^1$ H NMR (DMSO-d$_6$): δ 10.9 (1H, s), 10.8 (1H, s), 8.6 (1H, t, J=5.1), 8.5 (1H, d, J=8.4), 8.4 (1H, d, J=7.1), 8.2 (1H, s), 7.8 (1H, dd, J=8.4, 7.1), 4.8 (2H, d, J=5.1), 4.0 (2H, s).

EXAMPLE 38

6-Aminomethyl-2,5-dihydroxy-benzo[de]isoquinoline-1,3-dione, Hydrochloride

4-Aminomethyl-3-hydroxy-1,8-napththalic anhydride (0.13 g, 0.5 mmol, from Example B1) and hydroxylamine hydrochloride were reacted in pyridine (10 mL) following the procedure of Example 1 to give 0.08 g of the title compound, mp 265–269° C.;

$^1$H NMR (DMSO-d$_6$): δ 11.5 (1H, br s), 10.8 (1H, br s), 8.6 (1H, d, J=8.2), 8.4–8.1 (5H, br m), 7.9 (1H, dd, J=8.2, 7.1), 4.5 (2H, br s).

EXAMPLE 39

6-Acetamidomethyl-2,5-dihydroxy-benzo[de]isoquinoline-1,3-dione

4-Acetamidomethyl-3-hydroxy-1,8-napththalic anhydride (0.2 g, 0.7 mmol, from Example C1) was reacted with hydroxylamine (0.1 g, 1.4 mmol) in pyridine (10 mL) following the procedure of Example 1 to give 0.1 g of the title compound, mp 268–272° C.;

$^1$H NMR (DMSO-d$_6$): δ 11.0–10.6 (2H, br s), 8.5–8.4 (2H, m), 8.3 (1H, d, J=7.1), 8.1 (1H, s), 7.8 (1H, dd, J=8.2, 7.1), 4.8 (2H, d, J=5.1), 1.8 (3H, s).

EXAMPLE 40

6-Acetamidomethyl-2-hydroxy-5-methoxy-benzo[de]isoquinoline-1,3-dione

4-Acetamidomethyl-3-methoxy-1,8-napththalic anhydride (0.26 g, 0.9 mmol, from Example D1) was reacted with hydroxylamine (0.1 g, 1.4 mmol) in pyridine (10 mL) following the procedure of Example 1 to give 0.24 g of the title compound, mp 237–239° C.;

$^1$H NMR (DMSO-d$_6$): δ 10.3 (1H, br s), 8.5 (1H, d, J=8.5), 8.4 (1H, d, J=6.9), 8.3 (1H, s), 8.2 (1H, t, J=5.1), 7.9 (1H, dd, J=8.5, 6.9), 4.8 (2H, d, J=5.1), 4.1 (3H, s), 1.8 (3H, s).

EXAMPLE 41

6-Aminomethyl-2-hydroxy-5-methoxy-benzo[de]isoquinoline-1,3-dione

4-Aminomethyl-3-methoxy-1,8-napththalic anhydride (0.2 g, 0.8 mmol, from Example F1) and hydroxylamine (0.1 g, 1.4 mmol) were reacted in pyridine (10 mL) following the procedure of Example 1 to give 0.2 g of the title compound, mp 276–279° C.;

$^1$H NMR (DMSO-d$_6$): δ 11.0–10.5 (1H, br s), 8.7 (1H, d, J=8.5), 8.6–8.2 (4H, br m), 7.9 (1H, dd, J=8.5, 7.4), 4.6 (2H, s), 4.1 (3H, s).

EXAMPLE 42

2-Hydroxy-5,8-dinitro-benzo[de]isoquinoline-1,3-dione 3,6-Dinitro-1,8-naphthalic anhydride (0.7 g, 3.0 mmol, from Example G1) and hydroxylamine hydrochloride (0.3 g, 7.0 mmol) were reacted in pyridine (10 mL) following the general procedure of Example 1 to give 0.6 g of the title compound, mp 317–320° C.;
$^1$H NMR (DMSO-d$_6$): δ 11.2 (1H, s), 9.8 (2H, d, J=2.1), 9.1 (2H, d, J=2.1).

EXAMPLE 43

5,8-Diamino-2-hydroxy-benzo[de]isoquinoline-1,3-dione

A solution of 1% HCl in ethanol (100 mL) was added to 2-tert-butyldimethyl-silyloxy-5,8-diamino-benzo[de]isoquinoline-1,3-dione (0.4 g, 1.0 mmol, from Example I1) with stirring at room temperature. After 1 hour, the solids formed were filtered, washed with ether, and dried to give 0.2 g of the title compound, mp 329–336° C.;
$^1$H NMR (DMSO-d$_6$): δ 10.5 (1H, s), 7.6 (2H, d, J=2.1), 6.9 (2H, d, J=2.1), 5.8 (4H, br s).

EXAMPLE 44

5,8-Diacetamido-2-hydroxy-benzo[de]isoquinoline-1,3-dione

Treatment of 2-acetoxy-5,8-diacetamido-benzo[de]isoquinoline-1,3-dione (0.6 g, 1.6 mmol, from Example J1) with sodium hydroxide (0.07 g, 1.7 mmol) in methanol (30 mL) at room temperature for 2 hours, and acidification with 1N HCl gave a precipitate which was filtered, washed with water, and dried to give 0.2 g of the title compound, mp>350° C.;
$^1$H NMR (DMSO-d$_6$): δ 10.7 (1H, br s), 10.5 (2H, s), 8.6 (2H, d, J=1.7), 8.5 (2H, d, J=1.7), 2.1 (6H, s).

EXAMPLE 45

5-Hydroxy-11H-8,10-dioxa-5-aza-benzo[de]anthracene-4,6-dione 11H-5,8,10-Trioxabenzo[de]anthracene-4,6-dione (0.14 g, 0.5 mmol, from Example K1) and hydroxylamine hydrochloride (0.06 g, 0.9 mmol) were reacted in pyridine (4.0 mL) following the procedure of Example 1 to give 0.15 g of the title compound, mp>350° C.;
$^1$H NMR (DMSO-d$_6$): δ 10.8 (1H, s), 8.4 (1H, dd, J=7.0), 8.1 (1H, d, J=7.6), 8.0 (1H, s), 7.8 (1H, dd, J=7.5, 7.4), 5.5 (2H, s), 5.4 (2H, s).

EXAMPLE 46

5-Hydroxy-11-methoxy-11H-8,10-dioxa-5-aza-benzo[de]anthracene-4,6-dione 11H-11-Methoxy-5,8,10-trioxabenzo[de]anthracene-4,6-dione (0.16 g, 0.5 mmol, from Example L1) and hydroxylamine hydrochloride (0.05 g, 0.7 mmol) were reacted in pyridine (4 mL) following the procedure of Example 1 to give 0.1 g of the title compound, mp 249–251° C.;
$^1$H NMR (DMSO-d$_6$): δ 10.8 (1H, s), 8.4 (1H, d, J=7.2), 8.3 (1H, d, J=8.4), 8.0 (1H, s), 7.9 (1H, dd, J=8.2, 7.7), 6.2 (1H, s), 5.5 (1H, d, J=5.8), 5.4 (1H, d, J=5.8), 3.7 (3H, s).

EXAMPLE 47

2-Hydroxy-5-methoxy-6-nitro-benzo[de]isoquinoline-1,3-dione

3-Methoxy-4-nitro-1,8-naphthalic anhydride (0.3 g, 1.2 mmol, from Example M1) and a solution of hydroxylamine hydrochloride (0.1 g, 1.4 mmol) in water (2 mL) were reacted in ethanol (25 mL) following the procedure of Example 10 to give 0.1 g of the title compound, mp 264–265° C.;
$^1$H NMR (DMSO-d$_6$): δ 11.0 (1H, s), 8.4 (2H, m), 8.0 (2H, m), 4.2 (3H, s).

EXAMPLE 48

2-Hydroxy-6,7-dinitro-benzo[de]isoquinoline-1,3-dione 4,5-Dinitro-1,8-naphthalic anhydride (1.0 g, 3.5 mmol, from Example N1) and a solution of hydroxylamine hydrochloride (0.3 g, 4.5 mmol) in water (2 mL) were reacted in ethanol (25 mL) following the procedure of Example 10 to give 0.15 g of the title compound, mp 290–291° C.;
$^1$H NMR (DMSO-d$_6$): δ 11.2 (1H, s), 8.7 (2H, d, J=7.0), 8.6 (2H, d, J=7.0).

EXAMPLE 49

5-Bromo-2-hydroxy-6-(piperidine-1-yl)-benzo[de]isoquinoline-1,3-dione

To a solution of 2-benzyloxy-5-bromo-6-(piperidin-1-yl)-benzo[de]isoquinoline-1,3-dione (0.27 g, 0.58 mmol, from Example T1-A) in TFA (5 mL) at 0° C. was added a 1.0 M solution of boron tris(trifluoroacetate) in TFA (3 mL). The reaction was stirred at 0° C. for 2 hours. Ethyl ether was added forming a precipitate which was collected by filtration. The solid was taken up in chloroform, the organic layer washed with water, dried, filtered, and evaporated under reduced pressure to give 0.060 g of the title compound as the TFA salt, mp>250° C.

EXAMPLE 50

5-Bromo-2-hydroxy-6-(4-methylpiperazin-1-yl)-benzo[de]isoquinoline-1,3-dione

Following the procedure of Example 49, 2-benzyloxy-5-bromo-6-(4-methylpiperazin-1-yl)-1,3-dioxo-benzo[de]isoquinoline-1,3-dione (0.20 g, 0.45 mmol, from Example V1) was reacted to give 0.10 g of the title compound, mp 184–186° C.

EXAMPLE 51

5-Bromo-2-hydroxy-6-(3-methylpiperidin-1-yl)-benzo[de]isoquinoline-1,3-dione

To a solution of 2-benzyloxy-5-bromo-6-(3-methylpiperidin-1-yl)-benzo[de]isoquinoline-1,3-dione (0.24 g, 0.50 mmol, from Example U1) in TFA (8.0 mL) at 0° C. was added a 1.0 M solution of boron tris(trifluoroacetate) in TFA (5 mL). The reaction was stirred at 0° C. for 2 hours, then poured into a solution of water/methanol (1:1), and extracted with chloroform. The organic layer was dried over MgSO$_4$, filtered, and the solvent removed under vacuum to give 0.19 g of the title compound as the TFA salt, mp>250° C.

EXAMPLE 52

5-Bromo-2-hydroxy-6-(pyrrolidin-1-yl)-benzo[de]isoquinoline-1,3-dione

To a solution of 2-benzyloxy-5-bromo-6-(pyrrolidin-1-yl)-benzo[de]isoquinoline-1,3-dione (0.23 g, 0.51 mmol, from Example W1) in TFA (5 mL) at 0° C. was added a 1.0

EXAMPLE 53

5-Bromo-6-dimethylamino-2-hydroxy-benzo[de]
isoquinoline-1,3-dione

Following the procedure of Example 52, 2-benzyloxy-5-bromo-6-dimethylamino-benzo[de]isoquinoline-1,3-dione (0.17 g, 0.39 mmol, from Example X1) in TFA and a 1.0 M solution of boron tris(trifluoroacetate) in TFA (2 mL) were reacted to give 0.12 g of the title compound, mp 185–187° C.

EXAMPLE 54

(S)-6-(3-Amino-pyrrolidin-1-yl)-5-bromo-2-hydroxy-1H-benzo[de]isoquinoline-1,3-dione, Hydrochloride Following the procedure of Example 52, (S)-[1-(2-benzyloxy-5-bromo-1,3-dioxo-2,3-dihydro-1H-benzo[de]isoquinoline-6-yl)-pyrrolidin-3-yl]-carbamic acid, tert-butyl ester (0.43 g, 0.76 mmol, from Example Y1) and a 1.0 M solution boron tris(trifluoroacetate) in TFA (3 mL) were reacted to give 0.073 g of (S)-6-(3-amino-pyrrolidin-1-yl)-5-bromo-2-hydroxy-1,3-dioxo-2,3-dihydro-benzo[de]isoquinoline-1,3-dione, which was converted to the hydrochloride salt by dissolving in HCl and freeze drying to give 0.053 g of the title compound, mp>250° C.

EXAMPLE 55

5-Cyano-2-hydroxy-6-(piperidin-1-yl)-benzo[de]
isoquinoline-1,3-dione

A mixture of 2-benzyloxy-5-cyano-6-(piperidin-1-yl)-benzo[de]isoquinoline-1,3-dione (0.16 g, 0.40 mmol, from Example D2) and 5% Pd/BaSO$_4$ (0.05 g) in THF (75 mL) was shaken in an atmosphere of hydrogen at 50 psi at ambient temperature for 86 hours with an additional 0.05 g of 5% Pd/BaSO$_4$ being added after 70 hours. The catalyst was removed by filtration and the filtrate evaporated under reduced pressure. The residue was chromatographed on silica using chloroform/methanol (10:1) to give 0.059 g of the title compound, mp>250° C.

EXAMPLE 56

5-Cyano-2-hydroxy-6-(morpholin-1-yl)-benzo[de]
isoquinoline-1,3-dione

Following the procedure of Example 55, 2-benzyloxy-5-cyano-6-(morpholin)-1-yl)-benzo[de]isoquinoline-1,3-dione (0.15 g, 0.36 mmol, from Example 2) and 5% Pd/BaSO$_4$ (0.025 g) in THF was reacted for 5 days with an additional 0.030 g of 5% Pd/BaSO$_4$ in methanol being added after 100 hours to give 0.050 g of the title compound, mp>250° C.

EXAMPLE 57

5-Cyano-2-hydroxy-6-(pyrrolidin-1-yl)-benzo[de]
isoquinoline-1,3-dione

Following the procedure of Example 52, 2-benzyloxy-5-cyano-6-(pyrrolidin)-1-yl)-benzo[de]isoquinoline-1,3-dione (0.15 g, 0.33 mmol, from Example B2) and a 1.0 M solution of boron tris(trifluoroacetate) in TFA (2 mL) was reacted to give 0.070 g of the title compound, mp 247–248° C.

EXAMPLE 58

(S)-6-(3-Amino-pyrrolidin-1-yl)-5-cyano-2-hydroxy-benzo[de]isoquinoline-1,3-dione, Hydrochloride Following the procedure of Example 55, (S)-[1-(2-benzyloxy-5-cyano-1,3-dioxo-2,3-dihydro-1H-benzo[de]isoquinoline-6-yl)-pyrrolidin-3-yl]-carbamic acid, tert-butyl ester (0.17 g, 0.31 mmol, from Example E2) and a 5% Pd/BaSO$_4$ (0.50 g) were reacted, with an additional 0.045 g and 0.030 g of 5% Pd/BaSO$_4$ in methanol (50 mL) being added after 100 hours and 120 hours, respectively, to give 0.056 g of (S)-[1-(5-cyano-2-hydroxy-1,3-dioxo-2,3-dihydro-1H-benzo[de]isoquinoline-6-yl)-pyrrolidin-3-yl]-carbamic acid, tert-butyl ester. This material was used in the next step without further purification.

The (S)-[1-(5-cyano-2-hydroxy-1,3-dioxo-2,3-dihydro-1H-benzo[de]isoquinoline-6-yl)-pyrrolidin-3-yl]-carbamic acid, tert-butyl ester from above was dissolved in EtOH and reacted with a stream of HCl gas forming a precipitate which was collected by filtration and dried to give 0.021 g of the title compound, mp>250° C.

EXAMPLE 59

5-Bromo-2-hydroxy-7-(pyrrolidin-1-yl)-benzo[de]
isoquinoline-1,3-dione

To a 0° C. solution of 2-allyloxy-5-bromo-7-(pyrrolidin-1-yl)-benzo[de]isoquinoline-1,3-dione (0.81 g, 2.0 mmol, from Example G2) in CH$_2$Cl$_2$ (40 mL) was added phenysilane (0.32 g, 3.0 mmol) and Pd(PPh$_3$)$_4$ (0.050 g, 0.043 mmol). The reaction was stirred for 15 minutes, and the resulting precipitate removed by filtration, washed with CH$_2$Cl$_2$, and dried to give 0.60 g of the title compound, mp 234–235° C.

EXAMPLE 60

2-Hydroxy-5-methyl-7-(pyrrolidin-1-yl)-benzo[de]
isoquinoline-1,3-dione

Following the procedure of Example 59, 2-allyloxy-5-methyl-7-(pyrrolidin-1-yl)-benzo[de]isoquinoline-1,3-dione (0.55 g, 1.8 mmol, from Example J2), phenylsiliane (0.29 g, 2.6 mmol), Pd(PPh$_3$)$_4$ (0.81 g, 0.070 mmol) in CH$_2$Cl$_2$ (40 mL) were reacted to give 0.35 g of the title compound, mp 236–237° C.

EXAMPLE 61

5-Bromo-2-hydroxy-7-(piperidin-1-yl)-benzo[de]
isoquinoline-1,3-dione

Following the procedure of Example 52, 2-benzyloxy-5-bromo-7-(piperidin-1-yl)-benzo[de]isoquinoline-1,3-dione (0.090 g, 0.19 mmol, from Example T1-B), and a 1.0 M solution of boron tris(trifluoroacetate) in TFA (2 mL) were reacted to give 0.020 g of the title compound as the trifluoroacetate salt, mp 134–136° C.

EXAMPLE 62

6-(3-Amino-pyrrolidin-1-yl)-2-hydroxy-benzo[de]
isoquinoline-1,3-dione

To [1-(2-tert-butyloxy-2,3-dihydro-1,3-dioxo-1H-benzo[de]isoquinolin-6-yl)-pyrrolidinyl-3-yl]-carbamic acid, tert- (Top of column 55:)
M solution of boron tris(trifluoroacetate) in TFA (3 mL). The reaction was stirred at 0° C. for 2 hours and poured into a water/ethanol solution (1:1). The solution was neutralized with saturated Na$_2$CO$_3$, the resulting precipitate removed by filtration, and chromatographed using chloroform/hexane (10:1) to give 0.10 g of the title compound, mp 170–172° C.

butyl ester (0.9 g, 2.0 mmol, from Example L2) was added 2.0 mL of TFA, and the mixture was stirred at room temperature for 3 hours. It was concentrated and the solid recrystalillized from ethanol/ether to give 0.5 g of the title compound, mp 238–242° C.

EXAMPLE 63

6-(3-Aminopyrrolidin-1-yl)-2-hydroxy-5-methoxy-benzo[de]isoquinoline-1,3-dione

Following the procedure from Example 62, TFA (1.0 mL) and [1-(2-tert-butyloxy-1,3-dioxo-2,3-dihydro-5-methoxy-1H-benzo[de]isoquinolin-6-yl)-pyrrolidin-3-yl]-carbamic acid, tert-butyl ester (0.2 g, 0.4 mmol, from Example N2) was stirred at room temperature overnight, concentrated, and the solid recrystalillized from ethanol/ether to give 0.02 g of the title compound, mp 217–222° C.

EXAMPLE 64 GENERAL PROCEDURE

5-Acetamido-2-hydroxy-6-(pyrrolidin-1-yl)-benzo[de]isoquinoline-1,3-dione

Following the procedure of Example 62, TFA (1.0 mL) and 5-acetamido-2-tert-butyloxy-6-(pyrrolidin-1-yl)-benzo[de]isoquinoline-1,3)-dione (0.2 g, 0.5 mmol, from Example Q2) was stirred at room temperature overnight. It was concentrated, and the solid recrystallized from ethanol/ether to give 0.02 g of the title compound, mp 280–284° C.

The following compounds were synthesized following the procedures described in Examples Q2 and 62. Pyridine and/or a few drops of DBU were used in some cases as co-bases or solvents (e.g., for solid amines or amine HCl salts).

| Example # | $R_6$ | mp ° C. |
|---|---|---|
| 65 | 1-piperidinyl | 252–255 |
| 66 | 1-morpholinyl | 289–292 |
| 67 | 1-thiomorpholinyl | 292–295 |
| 68 | 4-methyl-1-piperazinyl, TFA salt | 208–211 |
| 69 | 1-piperazinyl, TFA salt | 240–243 |

EXAMPLE 70 GENERAL PROCEDURE

5-Amino-2-hydroxy-6-(pyrrolidin-1-yl)-benzo[de]isoquinoline-1,3-dione

To 5-acetamido-2-hydroxy-6-(pyrrolidin-1-yl)-benzo[de]isoquinoline-1,3)-dione (200 mg, 0.59 mmol, from Example 64) was added 40% HCl in EtOH (5.0 mL) at 60° C. overnight, followed by cooling, concentrating, and recrystallization of the residue from ethanol/water solution to give the title compound, mp 253–256° C.

The following compounds were prepared using the procedure from Example 70.

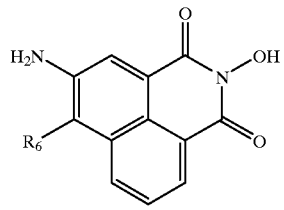

| Example # | $R_6$ | mp ° C. |
|---|---|---|
| 71 | piperidin-1-yl | 244–248 |
| 72 | 3-aminopyrrolidin-1-yl, HCl salt | 248–252 |
| 73 | thiomorpholin-1-yl | 270–274 |
| 74 | 4-methylpiperazin-1-yl, HCl salt | 342–344 |
| 75 | piperazin-1-yl, HCl salt | 236–244 |

EXAMPLE 76 GENERAL METHOD

2-Hydroxy-5-nitro-6-(pyrrolidin-1-yl)-benzo[de]isoquinoline-1,3-dione

Hydroxylamine hydrochloride (0.2 g, 2.9 mmol) and 3-nitro-4-(pyrrolidin-1-yl)-1,8-naphthalic anhydride (0.3 g, 1.0 mmol from Example R2) were refluxed in ethanol and water solution (10:1), or acetic acid (3.0 mL), for 6 hours. The solid was filtered and dried to give 0.30 g of the title compound, mp 249–252° C.

The following compounds were prepared using the procedures of Examples R2 and 76. When diamines such as 3-aminopyrrolidine were employed, the nitrogen was protected with the tert-butyloxycarbonyl group. This is cleaved in the final step with TFA. Compounds could be purified by crystallization from ethanol/ether.

| Example # | $R_6$ | mp ° C. |
|---|---|---|
| 77 | piperidin-1-yl | 252–254 |
| 78 | thiomorpholin-1-yl | 280–283 |
| 79 | piperazin-1-yl | 300–302 |
| 80 | 4-methylpiperazin-1-yl | 320–322 |
| 81 | morpholin-1-yl | 272–274 |
| 82 | 3-aminopyrrolidin-1-y1 | 259–263 |

EXAMPLE 83 GENERAL METHOD

5-Chloro-2-hydroxy-6-[3-methoxypyrrolidin-1-yl]-benzo[de]isoquinoline-1,3-dione

Following the procedure from Example 62, TFA (1.0 mL) and 2-tert-butyloxy-5-chloro-6-[3-methoxypyrrolidin-1-yl]-benzo[de]isoquinoline-1,3-dione (0.2 g, 0.5 mmol from Example S2) was stirred at room temperature overnight, concentrated, and the solid recrystallized from ethanol/ether solution to give 0.02 g of the title compound, mp 136–142° C.

The following compounds were prepared following the procedures of Examples S2 and 83. When diamines were used, the nitrogen was protected with the tert-butyloxycarbonyl group. These were cleaved in the final step with TFA to form TFA salts. If desired, addition of a solution of acetyl chloride (1.0 mL) in ethanol (5.0 mL) was used to form the HCl salts which were recrystallized from ethanol/ether solution to give the final product. When coupled products did not precipitate from water, they were extracted into dichloromethane, and concentrated.

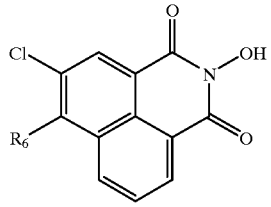

| Example # | R$_6$ | mp ° C. |
|---|---|---|
| 84 | (S)-3-hydroxypyrrolidin-1-yl | 197–201 |
| 85 | 3-(aminomethyl)pyrrolidin-1-yl, HCl salt | 229–232 |
| 86 | 3-(isopropylaminomethyl)pyrrolidin-1-yl, TFA salt | 218–220 |
| 87 | 3-[(3,3,3-trifluoroethyl)aminomethyl]-pyrrolidin-1-yl, TFA salt | 202–208 |
| 88 | 3-(ethylaminomethyl)pyrrolidin-1-yl, TFA salt | 190–195 |
| 89 | 3-methyl-3-(aminomethyl)pyrrolidin-1-yl, TFA salt | 160–166 |
| 90 | 3-(diethylaminomethyl)pyrrolidin-1-yl, HCl salt | 211–216 |
| 91 | (S)-3-aminopyrrolidin-1-yl, HCl salt | 309–313 |
| 92 | (R)-3-aminopyrrolidin-1-yl, HCl salt | 295–300 |

The preparation of 6-amino substituted-5-chloro-2-hydroxy-benzo[d,e]isoquinoline-1,3-diones using automated synthesis.

A mixture of 250 mg of 2-tert-butyloxy-5,6-dichloro-benzo[de]isoquinoline-1,3-dione (from Example V2) and 1 mL of the appropriate amine were prepared in 16×150 mm culture tubes. The tubes were sealed with teflon-lined screw-caps and heated to 90° C. for 4 to 8 hours, and then cooled to room temperature. Water (8 mL) was added to each of the tubes, which were then put into a freezer to let the product precipitate thoroughly. The solid was collected through filtration, washed with water and dried. The dried compounds were then reacted with 1 mL of trifluoroacetic acid in each tube with stirring for 1 hour. Absolute ethanol (1.0 mL) was added to each of the test tubes, followed by 8 mL of ether to precipitate the products. The solid was collected through filtration to give the titled compounds. When solid amines were employed, the reactions were run with 2 equivalents of each amine dissolved in 1 mL of pyridine. The following compounds were prepared in this manner.

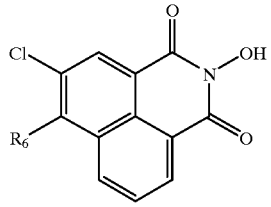

| Example # | R$_6$ | mp ° C. |
|---|---|---|
| 93 | morpholin-1-yl | 247–248 |
| 94 | piperidin-1-yl | 228–229 |
| 95 | thiomorpholin-1-yl | 240–242 |
| 96 | pyrrolidin-1-yl | 227–228 |
| 97 | piperazin-1-yl, TFA salt | >250 |
| 98 | 4-methylpiperizin-1-yl, TFA salt | >250 |
| 99 | 3-aminopyrrolidin-1-yl, TFA salt | >250 |

Preparation of 5-substituted ureido-2-hydroxy-benzo[de]isoquinoline-1,3-dione. General Procedure.

To a suspension of 3-amino-1,8-naphthalic anhydride (0.28 g, 1.4 mmol) in pyridine (50 mL) was added a substituted isocyanate (4 eq.) with stirring. The reaction mixture was warmed to 80° C. for 6 hours. The solvent was removed under reduced pressure. The residue was dissolved in acetone, then filtered. The filtrate was concentrated to 90% the original volume. Water was added to let the product precipitate thoroughly. The solid was collected through filtration, washed with water, ether, then dried under vacuo to give the 3-substituted uriedo-1,8-naphthalic anhydrides in 75% to 86% yield, which were used in the next step.

To a solution of 3-substituted uriedo-1,8-naphthalic anhydride (150 mg, 0.56 mmol, as prepared above) in pyridine (10 mL) was added hydroxylamine hydrochloride (120 mg, 3 eq.). The mixture was refluxed for 2 hours, poured into water (30 mL), and stirred for another 20 minutes. The precipitate was collected, washed with water, ether, and dried at 90° C. in vacuo to give the title compounds in 57% to 73% yields. The following compounds were prepared in this manner.

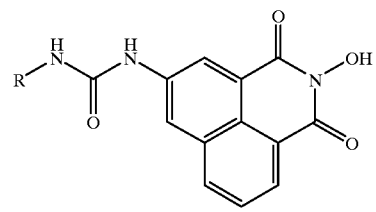

| Example # | R | mp ° C. |
|---|---|---|
| 100 | n-butyl | >250 |
| 101 | methyl | >250 |
| 102 | n-propyl | >250 |

EXAMPLE 103

5,6-Dichloro-2-hydroxy-benzo[de]isoquinoline-1,3-dione

A mixture of 3,4-dichloro-1,8-naphthalic anhydride (267 mg, 1.00 mmol, from Example U2) and hydroxylamine hydrochloride (276 mg, 2.00 mmol) in 10 mL of acetic acid was warmed to 80° C. with stirring overnight. Upon cooling, the precipitate was collected, washed with water and ether, and was dried to give 180 mg of the title compound, mp 267–269° C.

EXAMPLE 104

6-Bromo-5-methyl-2-hydroxy-benzo[de] isoquinoline-1,3-dione

To 4-bromo-3-methyl-1,8-naphthalic anhydride (140 mg, 0.48 mmol, from Example W2-A) was added hydroxylamine hydrochloride (140 mg, 1.0 mmol) in pyridine (5 mL), and the reaction was heated to 80° C. overnight, then cooled to room temperature. Water was added to precipitate the product. The solid was collected, washed with water and ether, dried, and recrystallized from DMA/H$_2$O, to give 102 mg of the title compound, mp 255–257° C.

EXAMPLE 105

6,8-Dibromo-2-hydroxy-5-methyl-benzo[de]- isoquinoline-1,3-dione

To 4,6-dibromo-3-methyl-1,8-naphthalic anhydride (50 mg, 0.14 mmol, from Example W2-B) was added hydroxylamine hydrochloride (100 mg, in excess) in pyridine (5 mL), and the reaction was heated to 80° C. overnight, then cooled to room temperature. Water was added to precipitate the product. The solid was collected, washed with water and ether, dried, and recrystallized from DMA/H$_2$O, to give 42 mg of the title compound, mp 320–323° C.

EXAMPLE 106

2-Hydroxy-6,7-dinitro-5-methoxy-benzo[de] isoquinoline-1,3-dione

A mixture of 4,5-dinitro-3-methoxy-1,8-naphthalic anhydride (0.3 g, 0.9 mmol, from Example X2) and hydroxylamine hydrochloride (0.079 g, 1.3 mmol) in acetic acid (15 mL) was heated at 100° C. for 12 hours. The solid was filtered and washed with ether to give 0.16 g, of the title compound, mp 272–273° C.

EXAMPLE 107

6,7-Diamino-2-hydroxy-5-methoxy-benzo[de] isoquinoline-1,3-dione

A mixture of 4,5-diamino-3-methoxy-1,8-naphthalic anhydride (0.2 g, 1.16 mmol, from Example Y2) and hydroxylamine hydrochloride (0.21, 3.48 mmol) in pyridine (10 mL) was heated at 80° C. for 4 hours and poured into ice water. The solid was filtered, washed with ether, dried, and recrystallized from acetic acid to give 0.2 g of the title compound, mp 317–318° C.

EXAMPLE 108

5-Bromo-2-hydroxy-6-nitro-benzo[de]isoquinoline- 1,3-dione

A mixture of 3-bromo-4-nitro-1,8-naphthalic anhydride (0.21 g, 0.65 mmol, from Example Z2) and hydroxylamine hydrochloride (0.12 g, 1.9 mmol) in acetic acid (8 mL) was heated at 80° C. for 12 hours and poured into ice water. The solid was filtered, washed with ether, and recrystallized from methanol to give 0.15 g of the title compound, mp 232–233° C.

EXAMPLE 109

5-Bromo-6,7-dinitro-2-hydroxy-benzo[de] isoquinoline-1,3-dione

A mixture of 3-bromo-4,5-nitro-1,8-naphthalic anhydride (0.3 g, 0.81 mmol, from Example A3) and hydroxylamine hydrochloride (0.148 g, 2.45 mmol) in acetic acid (15 mL) was heated at 80° C. for 5 hours. The reaction mixture was cooled to room temperature. The solid was filtered, washed with water and ether, and dried to give 0.15 g of the title compound, mp 233–234° C.

EXAMPLE 110

2-Hydroxy-5-nitro-7-(pyrrolidin-1-yl)-benzo[de] isoquinoline-1,3-dione

A mixture of 2-t-butyloxy-5-nitro-7-(pyrrolidin-1-yl)- benzo[de]isoquinoline-1,3-dione (0.09 g, 0.23 mmol, from Example D3-B) and TFA was stirred at room temperature for 4 hours and poured into water. The solid was filtered and washed with acetone to give (0.06 g, 80%) of the title compound, mp 290–291° C.

EXAMPLE 111

2-Hydroxy-5,8-dinitro-6-(pyrrolidin-1-yl)-benzo[de] isoquinoline-1,3-dione

A mixture of 3,6-dinitro-4-(pyrrolidin-1-yl)-1,8- napthalic anhydride (0.20 g, 0.56 mmol), from Example F3), hydroxylamine hydrochloride (0.10 g, 1.4 mmol), and sodium acetate (1.39 g, 16.8 mmol) in acetic acid (10 mL) was heated at 80° C. for 20 hours and poured into ice water. The solid was filtered, washed with water and ether, and dried to give 0.28 g of the title compound, mp 249–250° C.

EXAMPLE 112

5-Hydroxy-9-methyl-10H-5,8,10-triaza-cyclopenta [a]phenalene-4,6-dione

A mixture of 4-acetylamino-3-amino-1,8-naphthalic anhydride (0.10 g, 0.37 mmol, from Example I3) and hydroxylamine hydrochloride (0.10 g, 1.4 mmol) in pyridine (3 mL) was heated at 80° C. for 5 hours and poured into ice water. The solid was filtered, washed with ether, and recrystallized from ethanol to give 0.09 g of the title compound, mp>330° C.

EXAMPLE 113

5-Chloro-2-hydroxy-8-nitro-6-(pyrrolidin-1-yl)- benzo[de]isoquinoline-1,3-dione

A mixture of 2-tert-butyloxy-5-chloro-8-nitro-6- (pyrrolidin-1-yl)-benzo[de]isoquinoline-1,3-dione (0.2 g, 0.47 mmol, from Example M3-A) and TFA (1.6 mL) was stirred at room temperature for 2 hours and poured into ice water. The solid was collected, washed with water and ether, and dried to give 0.12 g of the title compound, mp 209–210° C.

EXAMPLE 114

5,6-Dichloro-2-hydroxy-7-(pyrrolidin-1-yl)-benzo [de]-isoquinoline-1,3-dione

A mixture of 2-tert-butyloxy-5,6-dichloro-7-(pyrrolidin- 1-yl)-benzo[de]isoquinoline-1,3-dione (50.0 mg, 0.12 mmol, from Example M3-B) and TFA (1.0 mL) was stirred at room temperature for 2 hours and poured into ice water. The solid was washed with water and ether, and dried to give 26 mg of the title compound, mp 200–201° C.

Using the procedures of Examples M3-A and B, 111, and 112, the following compounds were prepared.

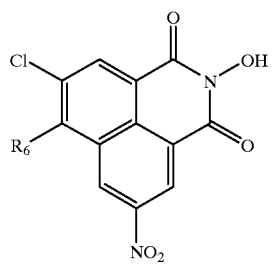

| Example # | R₆ | mp ° C. |
|---|---|---|
| 115 | 3-aminopyrrolidin-1-yl, TFA salt | 267–268 |
| 116 | morpholin-1-yl | 239–240 |

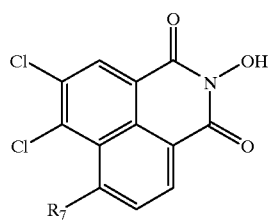

| Example # | R₇ | mp ° C. |
|---|---|---|
| 117 | 3-aminopyrrolidin-1-yl, TFA salt | 227–228 |
| 118 | morpholin-1-yl | 255–256 |

EXAMPLE 119

2,5-Dihydroxy-1,3-dioxo-2,3-dihydro-1H-benzo[de]isoquinoline-6-carboxaldehyde

To a suspension of 360 mg (1.33 mmol) of 5-hydroxy-11H-8,10-dioxa-5-aza-benzo[de]anthracene-4,6-dione (from Example 45) in 20 mL dioxane was added 0.36 mL (6.98 mmol) of bromine. The reaction mixture was refluxed for 1 hour and poured into 150 mL water. The precipitate was isolated and dried to yield 290 mg of the title compound, mp 237–253° C. (dec.)

EXAMPLE 120

6-Hydroximino-2,5-dihydroxy-methyl-benzo[de]isoquinoline-1,3-dione

To a solution of 300 mg (1.24 mmol) of 4-formyl-3-hydroxy-1,8-naphthalic anhydride (from Example N3) in 4 mL pyridine was added 230 mg (3.31 mmol) of hydroxylamine hydrochloride, and the reaction mixture was refluxed for 2 hours, and poured into 20 mL water while hot. The precipitate was isolated, dried, suspended in 5 mL MeOH, refluxed for 3 minutes, filtered, and dried to yield 256 mg of the title compound, mp 302–304° C.

EXAMPLE 121

2-Hydroxy-5,6-dimethoxy-benzo[de]isoquinoline-1,3-dione

To a solution of 100 mg (0.39 mmol) of 3,4-dimethoxy-1,8-naphthalic anhydride (from Example P3) in 3 mL pyridine was added 60 mg (0.86 mmol) of hydroxylamine hydrochloride and the reaction mixture refluxed for 2 hours, poured into 20 mL water while hot and acidified with 3 mL concentrated HCl. The precipitate was isolated, washed with water, and dried to yield 75 mg of the title compound, mp 226–228° C.

EXAMPLE 122

2-Hydroxy-5,6-methylenedioxy-benzo[de]isoquinoline-1,3-dione

To a solution of 200 mg (0.83 mmol) of 3,4-methylenedioxy-1,8-naphthalic anhydride (from Example Q3) in 2 mL pyridine was added 90 mg (1.29 mmol) of hydroxylamine hydrochloride and the reaction mixture refluxed for 1.5 hours and poured into 20 mL water while hot. The precipitate was isolated, filtered, washed with water, 1% HCl, water, and dried to yield 60 mg of the title compound, mp 303–304° C.

EXAMPLE 123

5-Hydroxy-9H,10H-8,11-dioxa-5-aza-benzo[de]anthracene-4,6-dione

To a solution of 70 mg (0.27 mmol) of 9H,10H-5,8,11-trioxabenzo[de]anthracene-4,6-dione (from Example R3) in 4 mL pyridine was added 80 mg (1.16 mmol) of hydroxylamine hydrochloride and the reaction mixture refluxed for 1.5 hours and poured into 20 mL water while hot. The precipitate was isolated after 24 hours, washed with water, 1% HCl, water, and dried to yield 71 mg of the title compound, mp 344–347° C.

EXAMPLE 124

5-Hydroxy-8H-9,11-dioxa-5-aza-benzo[de]anthracene-4,6-dione

To a solution of 310 mg (1.21 mmol) of 8H-5,9,11-trioxabenzo[de]anthracene-4,6-dione (from Example T3) in 4 mL pyridine was added 260 mg (3.74 mmol) of hydroxylamine hydrochloride and the reaction mixture refluxed for 2 hours and poured into 50 mL water while hot. The precipitate was isolated, washed with water, and dried to yield 190 mg of the title compound, mp 314–315° C.

EXAMPLE 125

2,5-Dihydroxy-6-bromo-benzo[de]isoquinoline-1,3-dione

To a solution of 980 mg (3.34 mmol) of 4-bromo-3-hydroxy-1,8-naphthalic anhydride (from Example X) in 4 mL pyridine was added 300 mg (4.32 mmol) of hydroxylamine hydrochloride. The reaction mixture was refluxed for 2 hours and poured into 150 mL water while hot. The precipitate was isolated, washed with water and dried to yield 990 mg of the title compound.

EXAMPLE 126

5-Hydroxy-10-methyl-9,10-dihydro-8-oxa-5,10-diaza-cyclopenta[a]phenalene-4,6-dione To a suspension of 175 mg (0.57 mmol) of 2,5-dihydroxy-6-bromo-benzo[de]isoquinoline-1,3-dione (from Example 125) in 4 mL dioxane was added 0.6 mL (22 mmol) of 37% aqueous formaldehyde, 0.2 mL (2.32 mmol) of 40% aqueous methylamine, and 0.078 mL (0.57 mmol) of triethyl amine. The reaction mixture was stirred at room temperature for 220 hours and quenched with 20 mL water. The precipitate was isolated, washed with water, and dried to yield 50 mg of the title compound, mp 263–265° C.

General procedure for the preparation of 10-substituted-5-hydroxy-11-H-8-oxa-5,10-diaza-benzo[de]anthracene-4,6-diones To a suspension of 180 mg (0.79 mmol) of 2,5-dihydroxy-benzo[de]isoquinoline-1,3-dione (from Example 3) in 6 mL dioxane was added 0.6 mL (8 mmol) of 37% aqueous formaldehyde, and then 0.8 to 2.9 mmol of the appropriate amine. The reaction mixture was stirred at room temperature 120 to 280 hours and quenched with 25 mL water. Precipitates formed were isolated, washed with water, and dried to yield, title compounds which are listed below.

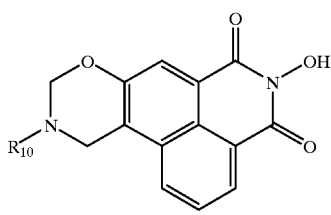

| Example # | R$_{10}$ | mp ° C. |
|---|---|---|
| 127 | —CH$_3$ | 247–249 |
| 128 | —CH$_2$CH$_2$OCH$_3$ | 211–213 |
| 129 | -n-Pentyl | 194–196 |
| 130 | —CH$_2$Ph | 220–221 |
| 131 | -c-Propyl | 215–216 |
| 132 | —CH$_2$-2-Pyridine | 221–222 |

EXAMPLE 133

2,5-Dihydroxy-6-(piperidin-1-yl)-methyl-benzo[de]isoquinoline-1,3-dione

To a suspension of 150 mg (0.66 mmol) of 2,5-dihydroxy-benzo[de]isoquinoline-1,3-dione (from Example 3) in 4 mL dioxane was added 0.6 mL (7.4 mmol) of 37% aqueous formaldehyde, and then 168 mg (2.0 mmol) of piperidine. The reaction mixture was stirred at room temperature 40 hours and quenched with 25 mL water. The precipitate was isolated, washed with water, and dried to yield 145 mg of the title compounds, mp 224–225° C.

EXAMPLE 134

5-Fluoro-2-hydroxy-6-(pyrrolidin-1-yl)-benzo[de]isoquinoline-1,3-dione

A solution of 28 mg (0.72 mmol) of 2-benzyloxy-5-fluoro-6-(pyrrolidin-1-yl)-benzo[de]isoquinoline-1,3-dione (from Example Z3) was hydrogenated over 15 mg of 10% Pd/C at room temperature and atmospheric pressure for 2 hours. Pd/C was removed by filtration, and the filtrate was evaporated to yield 10 mg of the title compound, mp 224–226° C.

EXAMPLE 135

2-Hydroxy-4-methoxy-benzo[de]isoquinoline-1,3-dione

Hydroxylamine hydrochloride (0.09 g, 1.3 mmol) was added to a solution of 2-methoxy-1,8-naphthalic anhydride (0.25 g, 1.1 mmol, from Example P1) in 15 mL of pyridine. The solution was heated to reflux for 4 hours, cooled, and poured onto 30 g of ice. The solution was concentrated to a solid, triturated with ether, triturated with 1N HCl, washed with water and dried to give 0.24 g of a solid. This solid was recrystallized from ethanol, filtered, and dried to give 0.14 g of the title compound as a solid, mp 205–206° C.

EXAMPLE 136

8-Amino-2-hydroxy-4-methoxy-benzo[de]isoquinoline-1,3-dione

Hydroxylamine hydrochloride (0.1 g, 1.34 mmol) was added to a solution of 6-Amine-2-methoxy-1,8-naphthalic anhydride (0.28 g, 1.2 mmol, from Example B4) in 25 mL of pyridine. The solution was heated to reflux for 18 hours, cooled and concentrated to a solid, washed with water and dried to give 0.16 g of the title compound, mp >250° C.

EXAMPLE 137

8-Bromo-5-chloro-6-(pyrrolidin-1-yl)-benzo[de]isoquinoline-1,3-dione

A mixture of 5-bromo-2-hydroxy-7-(pyrrolidin-1-yl)-benzo[de]isoquinoline-1,3-dione (0.15 g, 0.42 mmol, from Example 59) and NCS (0.072 g, 0.54 mmol) in acetic acid (12 mL) was reacted at 100° C. for 3 hours. The reaction mixture was cooled and poured into water. The resulting precipitate was collected by filtration, washed with water, and dried to give 0.072 g of the title compound.

EXAMPLE 138

4-Acetylamino-7-chloro-2-hydroxy-6-(pyrrolidin-1yl)benzo[de]isoquinoline-1,3 dione A solution of 4-acetylamino-2-allyloxy-7-chloro-6-(pyrrolidin-1-yl)benzo[de]isoquinoline-1,3-dione (0.24 g, 0.6 mmol, from Example H4) and phenylsilane (0.13 g, 1.2 mmol) in 15 mL of dichloromethane was cooled to 15° C. and treated with tetrakis(triphenylphosphine)palladium (27 mg, 0.02 mmol). The reaction was stirred for 1 hour and the solvent removed in vacuo. The residue was dissolved in methanol, filtered, and evaporated in vacuo. The residue was stirred with ether to give a fine precipitate which was filtered, washed with ether, and dried in vacuo to give 0.1 of the title compound, mp 152–154° C.

EXAMPLE 139

4-Amino-7-chloro-2-hydroxy-6-(pyrrolidin-1-yl)benzo[de]isoquinoline-1,3-dione

A suspension of 4-acetylamino-7-chloro-2-hydroxy-6-(pyrrolidin-1yl)benzo[de]isoquinoline-1,3-dione (0.08 g, 0.2 mmol, from Example 138), 0.5N sodium hydroxide (5 mL) and ethanol (5 mL) was heated to solution and then stirred to room temperature over 1 hour. The ethanol was evaporated in vacuo, the aqueous diluted to 15 mL with water, and acidified with acetic acid. The mixture was extracted with dichloromethane, dried, filtered, and evaporated in vacuo. The residue was triturated with ether/petroleum ether to give 0.035 g of the title compound, mp 211–213° C.

EXAMPLE 40

4,7-Dichloro-2-hydroxy-6-(pyrrolidin-1-yl)benzo[de]isoquinoline-1,3-dione

A solution of 2-allyloxy-4,7-dichloro-6-(pyrrolidin-1-yl)benzo[de]isoquinoline-1,3-dione (0.5 g, 1.3 mmol, from Example J4) in trifluoroacetic acid (10 mL) was treated with boron tristrifluoroacetate (6 mL, 6.0 mmol, 1.0 M in trifluoroacetic acid). The reaction mixture was stirred at room temperature for 4 hours and evaporated in vacuo. The residue was chased with dichloro methane and redissolved in methanol which was also evaporated. The residue was partitioned between dichloromethane/water, separated, the organic layer dried, and evaporated in vacuo. The residue was triturated with petroleum ether, the solid removed by filtration, and dried in vacuo to give 0.2 g of the title compound, mp 243–245° C.

EXAMPLE 141

(S)-6-(3-Aminopyrrolidin-1-yl)-4,7-dichloro-2-hydroxy-1H-benzo[de]isoquinoline-1,3-dione hydrochloride A solution of (S)-[1-(2-allyloxy-4,7-dichloro-1,3-dioxo-2,3-dihydro-1H-benzo[de]isoquinolin-6-yl)pyrrolidin-3-yl] carbamic acid tert-butyl ester (0.3 g, 0.6 mmol, from Example K4) in 10 mL of trifluoroacetic acid was treated with boron tristrifluoroacetate (4 mL, 4.0 mmol, 1.0 M in trifluoroacetic acid). The reaction was stirred at room temperature for 2 hours and the solvent evaporated in vacuo. The residue was chased with dichloromethane and redissolved in methanol which was also evaporated. The residue was triturated with ether, the solid removed by filtration and dried in vacuo to give 0.27 g, mp 210–212° C.

The compounds of the current invention were evaluated to demonstrate their desired antibacterial activities and inhibition of bacterial enzymes versus the undesired cell cytotoxicity and intercalation/binding to DNA. Control compounds were employed in the biological testing. These compounds include amonafide, mitonafide, and the 5,8-dinitro-2-(2-dimethylaminoethyl)-benzo[de]isoquinoline-1,3-dione (Reference Example 1). All three of these agents were prepared according to the procedure of Cheng, et al., *J. Med. Chem.*, 1985;28:1216.

Antibacterial assay: The compounds of the present invention were tested against an assortment of gram negative and gram positive organisms using standard microtitration techniques (Cohen, et al., *Antimicrob. Agents Chemother.*, 1985;28:766; Heifetz, et al. *Antimicrob. Agents Chemother.*, 1974;6:124). The results of the evaluation are shown in Table 1.

TABLE 1

Antibacterial Activity

Minimum Inhibitory Concentrations μg/mL

| | Gram Negatives | | | Gram Positives | | |
|---|---|---|---|---|---|---|
| Example # | E. coli MC4100 | E. coli B90 | E. coli Tol C | B. subtilis RB1 | S. aureus 29213 | S. pyogenes C203 |
| Amonafide | 64 | 16 | — | 64 | 128 | 4.0 |
| Mitonafide | 32 | 8.0 | — | 16 | 32 | 4.0 |
| Ref #1 | 8.0 | 2.0 | — | 2.0 | 4.0 | 2.0 |
| 1 | 4.0 | 2.0 | — | 8.0 | 8.0 | 32 |
| 2 | 8.0 | 4.0 | — | 4.0 | 2.0 | 4.0 |
| 4 | >64 | 8.0 | — | 8.0 | 16 | >64 |
| 7 | 4.0 | 4.0 | 4.0 | 16 | 8.0 | >64 |
| 8 | 8.0 | 4.0 | — | 8.0 | 32 | >64 |
| 11 | 8.0 | 2.0 | — | 8.0 | 64 | >64 |
| 13 | 0.5 | 0.13 | — | 1.0 | 8.0 | >64 |
| 14 | 2.0 | 0.25 | 0.13 | 1.0 | 8.0 | >64 |
| 16 | >64 | 1.0 | 1.0 | 2.0 | 8.0 | 64 |
| 18 | >64 | 4.0 | 1.0 | 2.0 | 1.0 | 4.0 |
| 21 | 8.0 | 2.0 | 1.0 | 4.0 | 16 | 64 |
| 23 | 16 | 2.0 | 1.0 | 4.0 | >64 | >64 |
| 26 | 0.5 | 0.25 | — | 0.5 | 2.0 | >64 |
| 28 | 16 | 1.0 | 1.0 | 4.0 | 4.0 | >64 |
| 30 | 8.0 | 4.0 | 2.0 | 4.0 | 4.0 | 64 |
| 32 | >64 | 8.0 | 4.0 | 4.0 | 8.0 | >64 |
| 35 | >64 | 64 | 64 | 2.0 | 1.0 | 4.0 |
| 42 | 4.0 | 1.0 | — | 16 | 8.0 | 32 |
| 45 | 0.5 | 0.13 | 0.13 | 0.25 | 1.0 | 8.0 |
| 48 | 16 | 4.0 | 4.0 | 8.0 | 2.0 | 1.0 |
| 49 | 64 | 4.0 | 8.0 | 1.0 | 2.0 | 64 |
| 50 | 32 | 2.0 | 2.0 | 4.0 | 8.0 | 8.0 |
| 53 | 64 | 2.0 | 1.0 | 2.0 | 4.0 | 32 |
| 54 | 2.0 | 0.5 | 0.5 | 2.0 | 8.0 | 4.0 |
| 57 | 32 | 0.5 | 0.5 | 1.0 | 4.0 | 32 |
| 59 | 2.0 | 0.06 | 0.06 | 0.5 | 1.0 | >64 |
| 62 | >64 | 32 | 8.0 | 64 | >64 | 4.0 |
| 64 | >64 | 32 | 16 | 64 | >64 | >64 |
| 71 | >64 | 4.0 | 4.0 | 2.0 | 2.0 | 16 |
| 81 | >64 | 8.0 | 8.0 | 8.0 | 32 | >64 |
| 85 | 1.0 | 0.5 | 0.25 | 1.0 | 4.0 | 4.0 |
| 86 | 8.0 | 0.5 | 0.5 | 2.0 | 4.0 | 4.0 |
| 89 | 4.0 | 1.0 | 0.5 | 1.0 | 1.0 | 2.0 |
| 98 | 32 | 4.0 | 4.0 | 8.0 | 16 | 8.0 |
| 99 | 2.0 | 1.0 | 0.5 | 1.0 | 8.0 | 4.0 |
| 102 | >64 | 32 | 16 | 16 | >64 | >64 |
| 103 | 16 | 0.5 | 0.5 | 1.0 | 16 | >64 |

TABLE 1-continued

Antibacterial Activity

Minimum Inhibitory Concentrations µg/mL

| | Gram Negatives | | | Gram Positives | | |
|---|---|---|---|---|---|---|
| Example # | E. coli MC4100 | E. coli B90 | E. coli Tol C | B. subtilis RB1 | S. aureus 29213 | S. pyogenes C203 |
| 104 | >64 | 0.25 | 0.25 | 0.5 | 4.0 | >64 |
| 108 | 8.0 | 0.25 | 0.5 | 2.0 | 4.0 | 16 |
| 111 | >64 | 2.0 | 4.0 | 32 | 8.0 | >64 |
| 115 | 8.0 | 0.5 | 0.5 | 2.0 | >64 | 4.0 |
| 117 | 2.0 | 0.5 | 0.25 | 2.0 | 8.0 | 8.0 |
| 120 | >64 | 2.0 | 1.0 | >64 | 16 | 64 |
| 122 | 2.0 | 0.5 | 0.5 | 2.0 | 8.0 | >64 |
| 131 | 32 | 8.0 | 8.0 | 32 | >64 | >64 |
| 134 | >64 | 0.5 | 0.5 | 1.0 | 1.0 | 8.0 |

DNA gyrase assay: The effects of test agents on the activity of DNA gyrase was determined by the supercoiling inhibition assay, following reaction conditions recommended by the enzyme supplier (Lucent, Ltd., Leicester, UK), as follows. Reactions were performed in buffer G (35 mM Tris-HCL (pH 7.5), 24 mM KCl, 4 mM $MgCl_2$, 2 mM DTT, 1.8 mM spermidine, 1 mM ATP, 0.1 mg/mL bovine serum albumin). 0.25 µg of relaxed plasmid pBR322 (Lucent, Ltd., Leicester, UK) was reacted with 1 U E. coli gyrase (Lucent, Ltd., Leicester, UK), in the absence or presence of drugs, for 30 minutes at 37° C. Reactions were stopped by the addition of SDS and proteinase K to respective final concentrations of 1% and 0.5 mg/mL. After an additional 30 minutes at 37° C., one-tenth volume of 10× loading buffer (0.3% bromophenol blue, 16% Ficoll, 10 mM $Na_2HPO_4$) was added, and reactions were loaded onto agarose gels and electrophoresed as described above for intercalation assays. The concentration of drug inhibiting 50% of the supercoiling activity of DNA gyrase is given as an $IC_{50}$ and recorded in Table 2.

Topoisomerase IV assay: Topoisomerase IV was purified from E. coli overexpressing strains and the compounds were assayed according to literature conditions (Journal of Biological Chemistry, 1993;268(32):24481). The k-DNA decatenation assay was used. Briefly, reactions were performed in buffer R (40 mM Tris-HCl (pH 7.5), 6 mM $MgCl_2$, 10 mM DTT, 100 mM potassium glutamate, 40 µM ATP, 50 µg/mL bovine serum albumin, 10 mM NaCl). 0.2 µg of kinetoplast DNA (k-DNA; TopoGen, Columbus, Ohio) was incubated with 5 ng of E. coli topoisomerase IV in the presence or absence of test compounds for 10 minutes at 37° C. Subsequently, one-tenth volume of 10× gel loading buffer (0.3% bromophenol blue, 16% Ficoll, 10 mM $Na_2HPO_4$) was added, and samples were loaded onto horizontal 0.8% agarose gels prepared with TBE buffer and containing 0.05 µg/mL of ethidium bromide. Electrophoresis was at 70 V for 2 to 4 hours. Gels were then examined by exposure to UV light. The concentration of drug inhibiting 50% of the decantenating activity of Topoisomerase IV is given as an $IC_{50}$ and recorded in Table 2.

TABLE 2

Inhibitory Activities vs DNA Gyrase and Topoismerase IV

| Example # | DNA Gyrase $IC_{50}$ (µM) | Top IV $IC_{50}$ (µM) |
|---|---|---|
| 8 | 7 | 65 |
| 13 | 11 | 29 |
| 26 | 7 | 10 |
| 28 | 20 | 7 |
| 42 | 20 | 20 |
| 50 | 31 | 97 |
| 59 | 2.6 | 101 |
| 62 | 18 | 101 |
| 81 | 19 | 101 |
| 85 | 2.1 | — |
| 89 | 5.5 | — |
| 98 | 15.8 | 3.0 |
| 103 | 4.9 | 19 |
| 115 | 0.7 | 9 |
| 117 | 10 | 4 |
| 120 | 30 | 25 |
| 122 | 19 | 101 |

Mammalian Cell Cytotoxicity: Compounds were also evaluated in the mammalian cell cytotoxicity assay following the procedures of Suto, et al., (J. Med. Chem., 1992;35:4745) and Ciaravino, et al., (Mutation Res., 1993;298:227). The cytotoxicity was determined in Chinese hamster V79 cells. The cells were grown overnight and treated with drug for 3 hours at 37° C., at which time the compound containing media was replaced with fresh media. The cells were then incubated for 5 days and examined for colony formation. The concentration of the drug inhibiting colony formation by 50% is represented by the $IC_{50}$ and is recorded in Table 3.

TABLE 3

Cytotoxicity to Mammalian Cells

| Example # | 50% Cytotoxic Conc. in CHO cells (µM) |
|---|---|
| Ref #1 | <8 |
| 4 | >250 |
| 8 | >500 |
| 13 | >250 |
| 16 | >250 |
| 28 | >250 |
| 32 | >250 |

TABLE 3-continued

Cytotoxicity to Mammalian Cells

| Example # | 50% Cytotoxic Conc. in CHO cells ($\mu$M) |
|---|---|
| 42 | 160 |
| 50 | 88 |
| 62 | 177 |

Intercalation assay: The compounds of the present invention were evaluated for their ability to intercalate/bind to DNA, using the procedure described in *Nucleic Acids Research*, 1987;15(16):6713. Specifically, 0.2 $\mu$g of relaxed plasmid pBR322 (Lucent, Ltd., Leicester, UK) was treated with 2 U of calf thymus topoisomerase I (Gibco/BRL, Gaithersburg, MD) in buffer I (10 mM Tris-HCl (Ph 7.5), 50 mM KCl, 5 mM MgCl$_2$, 1 mM Na$_2$EDTA, 15 $\mu$g/mL bovine serum albumin) in the presence or absence of test compounds. Reaction was incubated for 30 minutes at 37° C.; volumes were typically 30 $\mu$L. Reactions were terminated by the addition of sodium dodecylsulfate (SDS) to 1% and proteinase K to 0.5 mg/mL final concentrations. After an additional 30 minutes at 37° C., one-tenth volume of 10× concentrated loading buffer (0.3% bromophenol blue, 16% Ficoll, 10 mM Na$_2$HPO$_4$) was added, and samples were loaded onto horizontal 0.8% agarose gels prepared in TAE buffer. Electrophoresis was at 22 V for 14 hours. Gels were then stained by soaking for 1.5 hours in deionized water containing 0.2 $\mu$g/mL of ethidium bromide, followed by destaining in deionized water for an additional 1.5 hours. Gels were examined and photographed following exposure to UV light. The concentration of the drug which induced a 50% change in the DNA by intercalation is represented by an intercalation IC$_{50}$ and is recorded in Table 4.

TABLE 4

DNA Intercalation/Binding Assay

| Example # | Drug Concentration causing 50% intercalation of DNA ($\mu$M) |
|---|---|
| Amonafide | <10 |
| Mitonafide | — |
| Ref #1 | <10 |
| 1 | >100 |
| 2 | >100 |
| 7 | >100 |
| 8 | >100 |
| 11 | >100 |
| 13 | >100 |
| 16 | >100 |
| 26 | >100 |
| 28 | >100 |
| 30 | >100 |
| 32 | >100 |
| 42 | >100 |
| 59 | >100 |
| 81 | 94 |
| 98 | 19 |
| 103 | 26 |
| 122 | >100 |

What is claimed is:
1. A compound of Formula I

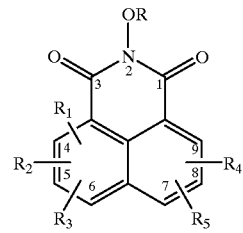

or a pharmaceutically acceptable salt thereof
wherein:
R is hydrogen;
$R_1$–$R_5$ are each independently chosen from H, Cl, Br, F, a heterocycle or bridged heterocycle of 4–9 atoms containing 1–3 heteroatoms, NO$_2$, OCH$_3$, CH$_3$, and any two of $R_1$–$R_5$ may form a substituted or unsubstituted ring of 5–7 total atoms having 0–2 heteroatoms and at least one or $R_1$–$R_5$ is a heterocycle;
n is an integer of from 0 to 5;
m is an integer of from 0 to 3;
$R_6$ and $R_7$ are independently hydrogen, a straight or branched alkyl of 1–6 carbons, a cycloalkyl of 3–6 carbons, a heterocycle of 5–6 atoms with 1–3 heteroatoms, or Ph, all of which may be optionally substituted;
$R_8$ is a cycloalkyl of 3–7 carbons or a heterocycle of 4–9 atoms with 1–4 heteroatoms;
R' is $R_6$, F, Br, Cl, OR$_6$, N(R$_6$)$_2$, and any two R's may form a ring of 3–6 total atoms with 0–2 heteroatoms;
wherein the alkyls, cycloalkyls, heterocycles, and Ph may be optionally substituted; and
wherein the substituents are selected from a straight or branched alkyl of 1–4 carbons, Br, F, Cl, —(CR'$_2$)$_n$OR$_6$, —(CR'$_2$)$_n$N(R$_6$)$_2$, —(CR'$_2$)$_n$NR$_6$COR$_7$, —(CR'$_2$)$_n$NR$_6$SO$_2$OR$_7$, —(CR'$_2$)$_n$NR$_6$SO$_2$N(R$_6$)$_2$, —(CR'$_2$)$_n$OSO$_2$N(R$_6$)$_2$, —(CR'$_2$)$_n$CN, —(CR'$_2$)$_n$C(NOR$_6$)R$_7$, NO$_2$, CF$_3$, —(CR'$_2$)$_n$SO$_m$R$_7$, —(CR'$_2$)$_n$CO$_2$R$_6$, —(CR'$_2$)$_n$R$_8$, —(CR'$_2$)$_n$CON(R$_6$)$_2$, and Ph.

2. A compound according to claim 1 wherein
R is hydrogen;
$R_1$, $R_2$, $R_3$, $R_4$, and $R_6$ are each independently selected from
hydrogen,
chlorine,
bromine,
fluorine,
heterocycle of from 4–8 atoms having from 1–3 heteroatoms,
—NO$_2$,
OCH$_3$, CH$_3$;
wherein
N is an integer from 0 to 5;
m is an integer of from 0 to 3; and
$R_6$ and $R_7$ are each independently selected from
hydrogen,
straight or branched alkyl of from 1–6 carbons,
cycloalkyl of from 3–6 carbons,
heterocycle of from 5–6 atoms having from 1–3 heteroatoms, or
phenyl;

$R_8$ is a heterocycle of 5 or 6 atoms with 1 or 2 heteroatoms;

R' is
hydrogen,
fluorine,
chlorine,
bromine,
$OR_6$, or
$N(R_6)_2$ wherein $R_6$ is alkyl; and each of alkyl, cycloalkyl, heterocycle, and phenyl above is each independently unsubstituted or substituted with from 1–3 substituents selected from:
methyl, ethyl, propyl, isopropyl, butyl, sec-butyl, t-butyl, F, Cl, Br, $CF_3$, CN, $COCH_3$, $CO_3H$, $CONH_2$, $C(R'_2)_nN(R_6)_2$, $C(R'_2)_nOR_6$, $NO_2$, $NR_6COR_6$, $CO_2R_6$, or $OCOR_6$.

3. A compound according to claim 1 wherein any two of $R_1$–$R_5$ may form a substituted or unsubstituted ring of from 5 to 7 atoms having from 0 to 2 heteroatoms selected from oxygen, sulfur, and nitrogen selected from:
1,3-benzodioxole,
2,3-dihydrobenzoxazole,
2,3-dihydrobenzofuran,
2,3-dihydro-1H-isoindole,
1,3-dihydroisofuran,
1,3-benzoxathiole,
2,3-dihydro-1H-indole,
2,3-dihydro-1,4-benzodioxin,
3,4-dihydro-2H-1,4-benzoxazine,
3,4-dihydro-2H-1,3-benzoxazine,
4H-1,3-benzodioxin,
3,4-dihydro-2H-1-benzopyran,
3,4-dihydro-1H-2-benzopyran,
1,2,3,4-tetrahydroquinoxaline,
1,2,4,4-tetrahydroisoquinoline,
2,3-dihydro-1,4-benzoxathinindane, and
1,2,3,4-tetrahydronaphthalene.

4. A compound according to claim 1 wherein
R is H; and any of $R_1$–$R_5$ may be piperidine, morpholine, piperazine, pyrrolidine, or thiomorpholine.

5. A compound according to claim 1 wherein:
R is H;
$R_1$–$R_5$ is H, Cl, Br, F, $OCH_3$, $NO_3$, or $CH_3$ and at least one $R_1$–$R_5$ is a heterocycle.

6. A compound according to claim 1 wherein:
R is H;
$R_1$–$R_5$ is H, Cl, Br, F, $OCH_3$, $NO_2$, or $CH_3$ and at least one $R_1$–$R_5$ is 3- or 4-amino-piperidin-1-yl, 3- or 4-aminomethyl-piperidin-1-yl, 3-amino or 3-aminomethyl-pyrrolidin-1-yl, 3-amino or 3-aminomethyl-azetidin-1-yl, [S-(R*,S*)]-3-(1-aminoethyl)-pyrrolidin-1-yl, trans-3-amino-4-methyl-pyrrolidin-1-yl, 6-amino-3-azo-bicyclo[3.1.0]hex-3-yl, and octahydro-1H-pyrrolo[3,4-b]pyridine-6-yl.

7. A compound according to claim 1 wherein:
R is H;
$R_2$ is halogen at the five position;
$R_3$ is heterocycle at the six position which heterocycle is selected from an unsubstituted or substituted piperazinyl, morpholinyl, pyrrolidinyl, azetidinyl, bicyclo[3.1.0]hex-1-yl, 2-azabicyclo[4.3.0]nonane-2-yl, and piperidinyl;

which substituents are one or more selected from $-(CR'_2)_nOR_6$, $-(CH'_2)_nN(RT_6)_2$, $-(CR'_2)_n NR_6COR_7$, $-(CR'_2)_nNR_6(SO_2OR_7)$, $-(CH'_2)_n NR_6SO_2N(R_6)_2$, $-(CR'_2)_nOSO_2N(R_6)_2$, $-(CR'_2)_n CN$, $-(CR'_2)_nC(NOR_6)R_7$, $NO_2$, $-(CR'_2)_nSO_mR_7$, $-(CR'_2)_nCO_2R_6$, $-(CR'_2)_nCON(R_6)_2$, Ph, and F, Cl, and Br; and $R_4$ and $R_5$ are each hydrogen.

8. A compound according to claim 1 wherein any two R's can form a ring having from 3–6 atoms having from 0–2 heteroatoms.

9. A compound according to claim 1 and selected from:
5-Hydroxy-10-(pyridin-2-ylmethyl)-11H-8-oxa-5,10-diaza-benzo[de]anthracene-4,6-dione;
2-Hydroxy-6-(4-methyl-piperazin-1-yl)-benzo[de]isoquinoline-1,3-dione;
2-Hydroxy-6-(pyrrolidin-1-yl)-benzo[de]isoquinoline-1,3-dione;
2-Hydroxy-6-(morpholin-4-yl)-benzo[de]isoquinoline-1,3-dione;
2-Hydroxy-6-(piperidin-1-yl)-benzo[de]isoquinoline-1,3-dione;
2-Hydroxy-5-methoxy-6-(4-methyl-piperazin-1-yl)-benzo[de]isoquinoline-1,3-dione, hydrochloride;
2-Hydroxy-5-methoxy-6-(pyrrolidin-1-yl)-benzo[de]isoquinoline, 1,3-dione;
2-Hydroxy-5-methoxy-6-(piperidin-1-yl)-benzo[de]isoquinoline-1,3-dione;
2-Hydroxy-5-methoxy-6-(morpholin-4-yl)-benzo[de]isoquinoline-1,3-dione;
5-Bromo-2-hydroxy-6-(piperidine-1-yl)-benzo[de]isoquinoline-1,3-dione;
5-Bromo-2-hydroxy-6-(4-methylpiperazin-1-yl)-benzo[de]isoquinoline-1,3-dione;
5-Bromo-2-hydroxy-6-(3-methylpiperidin-1-yl)-benzo[de]isoquinoline-1,3-dione;
5-Bromo-2-hydroxy-6-(pyrrolidin-1-yl)-benzo[de]isoquinoline-1,3-dione;
(S)-6-(3-Amino-pyrrolidin-1-yl)-5-bromo-2-hydroxy-benzo[de]isoquinoline-1,3-dione, hydrochloride;
5-Cyano-2-hydroxy-6-(piperidin-1-yl)-benzo[de]isoquinoline-1,3-dione;
5-Cyano-2-hydroxy-6-(morpholin-1-yl)-benzo[de]isoquinoline-1,3-dione;
5-Cyano-2-hydroxy-6-(pyrrolidin-1-yl)-benzo[de]isoquinoline-1,3-dione;
(S)-6-(3-Amino-pyrrolidin-1-yl)-5-cyano-2-hydroxy-benzo[de]isoquinoline-1,3-dione, hydrochloride;
5-Bromo-2-hydroxy-7-(pyrrolidin-1-yl)-benzo[de]isoquinoline-1,3-dione;
2-Hydroxy-5-methoxy-7-(pyrrolidin-1-yl)-benzo[de]isoquinoline-1,3-dione;
5-Bromo-2-hydroxy-7-(piperidin-1-yl)-benzo[de]isoquinoline-1,3-dione;
6(3-Amino-pyrrolidin-1-yl)-2-hydroxy-benzo[de]isoquinoline-1,3-dione;
6-(3-Aminopyrrolidin-1-yl)-2-hydroxy-5-methoxy-benzo[de]isoquinoline-1,3-dione;
5-Acetamido-2-hydroxy-6-(pyrrolidin-1-yl)-benzo[de]isoquinoline-1,3-dione;
5-Amino-2-hydroxy-6-(pyrrolidin-1-yl)-benzo[de]isoquinoline-1,3-dione;

2-Hydroxy-5-nitro-6-(pyrrolidin-1-yl)-benzo[de]
isoquinoline-1,3-dione;

5-Chloro-2-hydroxy-6-[3-methoxypyrrolidin-1-yl]-benzo
[de]isoquinoline-1,3-dione;

2-Hydroxy-8-nitro-6-(pyrrolidin-1-yl)-benzo[de]
isoquinoline-1,3-dione;

2-Hydroxy-5,8-dinitro-6-(pyrrolidin-1-yl)-benzo[de]
isoquinoline-1,3-dione;

5-Chloro-2-hydroxy-8-nitro-6-(pyrrolidin-1-yl)-benzo
[de]isoquinoline-1,3-dione;

5,6-Dichloro-2-hydroxy-7-(pyrrolidin-1-yl)-benzo[de]
isoquinoline-1,3-dione;

2,5-Dihydroxy-6-(piperidin-1-yl)-methyl-benzo[de]
isoquinoline-1,3-dione;

2-Hydroxy-6-(piperidin-1-yl)-benzo[de]isoquinoline-1,3-
dione;

5-Fluoro-2-hydroxy-6-(pyrrolidin-1-yl)-benzo[de]
isoquinoline-1,3-dione;

8-Bromo-5-chloro-2-hydroxy-6-(pyrrolidin-1-yl)-benzo
[de]isoquinoline-1,3-dione.

10. A process for the preparation of a compound of Formula I according to claim 1 comprising a) reacting a nitrogen-containing heterocycle with a compound of the formula

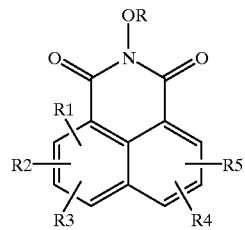

wherein

R is hydrogen; and $R_1$–$R_5$ are according to claim 1, and one of $R_1$–$R_5$ is a leaving group selected from halogen, OMe, $NO_2$, and triflate, which leaving group is displaced by said nitrogen heterocycle, and b) converting the product of step a), if desired, to a pharmaceutically acceptable salt thereof.

11. A process for the preparation of a compound of Formula I of claim 1 comprising a) reacting a nitrogen-containing heterocycle with a compound of formula

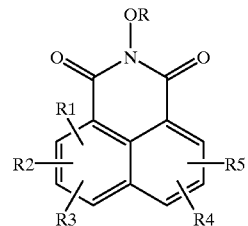

wherein

R is a protecting group typically used in the art for protecting alcohols: benzyl, 4-methoxybenzyl, methyl, acetyl, benzoyl, 2,2,2-trichloroethyl, t-butyldimethylsilyl, t-butyl, and allyl; and and $R_1$–$R_5$ are according to claim 1, and one of $R_1$–$R_5$ is a leaving group selected from halogen, OMe, $NO_2$, and triflate, which leaving group is displaced by said nitrogen heterocycle, and b) deprotecting the produce of step a), and c) converting the product of step b), if desired, to a pharmaceutically acceptable salt thereof.

* * * * *